United States Patent
Arends

(10) Patent No.: US 12,176,086 B1
(45) Date of Patent: *Dec. 24, 2024

(54) SYSTEMS, METHODS, AND APPARATUSES FOR GENERATING PHARMACY PRESCRIPTION RECORDS INCLUDING EXCEPTION CASES

(71) Applicant: WALGREEN CO., Deerfield, IL (US)

(72) Inventor: Jon J. Arends, Chicago, IL (US)

(73) Assignee: WALGREEN CO., Deerfield, IL (US)

( * ) Notice: Subject to any disclaimer, the term of this patent is extended or adjusted under 35 U.S.C. 154(b) by 230 days.

This patent is subject to a terminal disclaimer.

(21) Appl. No.: 16/710,580

(22) Filed: Dec. 11, 2019

(51) Int. Cl.
G06Q 50/00 (2024.01)
G06F 16/25 (2019.01)
G16H 10/60 (2018.01)
G16H 20/10 (2018.01)

(52) U.S. Cl.
CPC .......... *G16H 20/10* (2018.01); *G06F 16/252* (2019.01); *G16H 10/60* (2018.01)

(58) Field of Classification Search
CPC .............................. G16H 10/60; G16H 20/10
See application file for complete search history.

(56) References Cited

U.S. PATENT DOCUMENTS

| | | | | |
|---|---|---|---|---|
| 11,676,692 B1 * | 6/2023 | Arends | ................... | G06F 9/542 705/3 |
| 2003/0139945 A1 * | 7/2003 | Brown | ................... | G16H 20/10 600/300 |
| 2003/0195774 A1 * | 10/2003 | Abbo | ..................... | G16H 40/20 705/3 |
| 2004/0010511 A1 * | 1/2004 | Gogolak | ................ | G16H 70/40 |
| 2004/0138921 A1 * | 7/2004 | Broussard | .............. | G16H 20/13 705/2 |
| 2006/0111948 A1 * | 5/2006 | Kivatinetz | ............. | G06Q 10/10 705/4 |
| 2007/0214009 A1 * | 9/2007 | Epstein | ................... | G16Z 99/00 600/300 |
| 2008/0058773 A1 * | 3/2008 | John | .................. | A61N 1/37235 604/891.1 |
| 2008/0061961 A1 * | 3/2008 | John | .................. | A61N 1/37258 600/300 |
| 2008/0288023 A1 * | 11/2008 | John | ...................... | G16H 20/40 607/59 |

(Continued)

FOREIGN PATENT DOCUMENTS

KR 100366817 B1 * 1/2003

*Primary Examiner* — Rajesh Khattar
(74) *Attorney, Agent, or Firm* — MARSHALL, GERSTEIN & BORUN LLP; Randall G. Rueth

(57) ABSTRACT

A method and system may provide an automated pharmacy processing system which may automatically processes an electronic prescription by converting the electronic prescription into a pharmacy prescription record that may include exception cases. In this way, an electronic prescription for a medication that is not within a formulary of a patient may be filled by a pharmacist without manual data entry. The system receives an electronic prescription and compares data from the electronic prescription with entries in one or more drug utilization rules. When there is a match between the electronic prescription data and an entry in the one or more drug utilization rules, the system may perform a drug utilization review with an alternate prescription.

12 Claims, 34 Drawing Sheets

(56) References Cited

U.S. PATENT DOCUMENTS

| | | | |
|---|---|---|---|
| 2013/0173277 A1* | 7/2013 | Eller | G16H 40/67 |
| | | | 705/2 |
| 2014/0074492 A1* | 3/2014 | Momita | G16H 20/10 |
| | | | 705/2 |
| 2014/0088981 A1* | 3/2014 | Momita | G16H 70/40 |
| | | | 705/2 |
| 2015/0220690 A1* | 8/2015 | Kahlon | G06Q 40/08 |
| | | | 705/2 |
| 2016/0085938 A1* | 3/2016 | Hans | G06Q 10/10 |
| | | | 705/2 |
| 2019/0095582 A1* | 3/2019 | Waits | G16H 10/60 |

* cited by examiner

300

Medication: Prozac-capsules

Hx  Current: 12/10/2013 Prozac 10mg ▼ —328

Date: 12/10/2013 ▼   30 ▲▼ Days

324 — Facility:   Prescriber: John Doe —316
DEA#: AA55555555 —318
License#: 111111111 —320
Phone: —322

302 — Name: Chris Bryant [...]   Age: 21 —304

Address: 555 N.MichiganAve, Chicago, IL —308

Date: 12/10/2013

310 — Prozac-capsules 10mg —330
312 — SIG: Ingest 4 10 mg capsules, once a day

Electronic Prescription

314 — DISP: 120 ▲▼ Days

This Prescription will Be Filled Generically Unless DAW is Yes

326 — DAW  No ▲▼

| Write | Print | Renew | Transmit |

Save    Cancel

| 405 | 410 | 415 |
|---|---|---|
| ACCUTANE 40MG CAPSULES | This is a Pregnancy Category X drug and is contraindicated for use if pregnant or planning to become pregnant. If patient is FEMALE - Counsel about PREGNANCY CONTRAINDICATION. | TAKE, USE, INJECT APPLY, INSERT, SPRAY, DIRECTED, TK, U, APP, ¡ |
| ACTIVELLA 0.5MG/0.1MG TAB | "Check STRENGTH" Do NOT confuse with Activella 1.0mg/0.5mg. | DAILY, QD, QAM, QHS, PER DAY |
| ACTONEL 35MG TABLETS (PAC | Stop! RISEDRONATE is dosed once weekly. Clarify directions with prescriber. | TAKE, ONE, 1, TABLET, TOME, UNA, TABLETA. |
| ACTONEL 35MG W/CALCIUM TA | Actonel is for Osteoporosis - DO NOT CONFUSE WITH ACTOS (for diabetes) ! Please CHECK the SCRIPT carefully. | TAKE, ONE, 1, TABLET, TOME, UNA, TABLETA. |
| ACTOS 15MG TABLETS | Actos is for diabetes - DO NOT CONFUSE WITH ACTONEL (for osteoporosis) ! Please CHECK the SCRIPT carefully. | TK, TAKE, TABLET, INJECT, NOSTRIL NOSE |
| ADVAIR DISKUS 500/50MCG ( | Advair is an orally inhaled medication. Please check route of administration and instructions. | USE, ONE, INHALATION, PO, BID, BY MOUTH, TWICE DAILY |
| ADVAIR DISKUS 500/50MCG 2 | CAUTION!!! - Do NOT confuse with ADVICOR 500MG/20MG TABLETS. Double check prescription. | INJECT, NASAL UNDER, SKN |
| AFREZZA ORAL INH POW 5U # | Afrezza is an ORALLY INHALED insulin. Check route of administration. | TAKE |
| AGENERASE 50MG CAPSULES | The normal dose of Agenerase is 1200 mg twice daily. | DROP, DROPS |
| AK-TROL | Invalid measure or incorrect drug. The dosage form OINTMENT cannot be measured in DROP(S), please clarify. | |
| ALBUTEROL INHALER (200 PU | Albuterol inhalers using CFCs can not be made, distributed, carried or SOLD, under any circumstances, in the U.S. after Dec. 31, 2008. CALL MD now to switch to use of a Albuterol HFA inhaler LIKE Pro-AIR. | SPRAY, INHALE, PUFF, 1, ONE, EVERY, HOURS, TIMES |
| ALCORTIN GEL 48GM | Alcortin Gel (NDC# 68134-702-13) has BEEN DISCONTINUED and REPLACED BY ALCORTIN-A Gel (NDC # 68040-705-13). | U, USE, EXTERNALLY, APP, APPLY, AREA |
| ALENDRONATE 70MG TABLETS | Stop! Alendronate is dosed once weekly. Clarify directions with prescriber. | DAILY, QD, QAM, QHS, PER DAY, D |
| AMBIEN CR 6.25MG TABLETS | Zolpidem is a sleeping aid and should only be taken at bedtime. | MORNING, MAÑANA, AM QAM |
| AMHORIGE 5MG TABLETS | BE CAREFUL !! Double Check Drug. Do NOT confuse with Amlodipine (generic for Norvasc). | TAKE, TK, 1, ONE, T, TABLET, TABLETS, BY MOUTH, PO |
| ANCHIDDERM 5MG TRANSDERMAL | IMPORTANT CHECK PROFILE This is a Pregnancy Category X drug and is contraindicated for use if pregnant or planning to become pregnant. If patient is FEMALE - Counsel about PREGNANCY CONTRAINDICATION IMPORTANT | TAKE, USE, INJECT APPLY, INSERT, SPRAY, DIRECTED, TK, U, APP, ¡ |
| ANTIBIOTIC EAR SOLUTION | Cortisporin Otic Drops cannot be used in the eye! Check route of administration. | EYE, EYES |
| ASTELIN 137MCG NASAL SPR( | This is a nasal inhaler and should not be used by mouth. Double check directions. | PO, ORALLY, ORAL, MOUTH, ORALES |
| BUDEPRION SR 150MG TABLET | STOP! Double check drug prescribed. This dosage form is generic for WELLBUTRIN SR, it is NOT equivalent to generic Wellbutrin XL or Zyban. | TK, TAKE, 1, ONE, I, TABLET, PO, BY MOUTH, BID, TWICE DAILY |
| BUPRENORPHINE 2MG SL TABL | Doctors using this drug for opioid addiction need special "data waiver #" that begins with X and is in GFA # format. If given for other use- X number is not required. See Buprenorphine Policy & Procedures on StoreNet>Drug Info>Specialty Drugs. | TK, 1, I, TABLET, TS, TABLETS, ONE, TAKE, 2 TWO |
| BYETTA 5MCG PEN (250MCG/M | Byetta is dosed and displayed in MCG only. Prescriber clarification is required when directions are written in ML. | ML, MLS, MILLILITERS, CC |
| CARBAMAZEPIN 200MG TABLET | Your state may require Contact and Documentation to prescriber if there is a substitution, change in manufacturer or therapy. Patient MUST be notified before interchange is done and documented. | TK, TAKE, ONE, 1, T, TABLET, PO, BY MOUTH, D, DAILY |
| MORPHINE SUL 100MG/5ML120 | The drug should be dosed in mls not teaspoonfuls. Please calculate the correct number of mls and re-enter the directions. Dispense the appropriate measuring device to the patient. BE CAREFUL - HIGHLY CONCENTRATED SOLUTION !!! | MILLILITERS, MLS, ML, TK, TAKE, CUCHARADITA, CUCHARADITAS, |
| MORPHINE SUL 100MG/5ML(20 | CAUTION! This drug can be fatal if dosed incorrectly. Review dosing calculations for this highly concentrated solution. | XYZ |

Drug ID: OFLOXACIN 0.3% OTIC SOLN 10ML (EAR)
Directions:
AC/HC:

| Type | Severity | Rx # | Rx Date | Overridden |
|---|---|---|---|---|
| ROUTE OF ADMIN CONTRAINDICATED | MAJOR | | | |

DUR Summary:
ABSOLUTE CONTRAINDICATION! Ear Drops CANNOT be used in the eye. Clarify directions with prescriber.

Drug ID: BUPROPION XL 300MG TABLETS

Directions: TAKE 3 TABLETS BY MOUTH EVERY MORNING   AC/HC:

| Type | Severity | Rx # | Rx Date | Overridden |
|---|---|---|---|---|
| DUPLICATE THERAPY - BUPROPION XL 150MG TABLETS (24 H | MAJOR | | | |
| DRUG DOSAGE CONDITION ENCOUNTERED | MAJOR | | | |
| DRUG / HLTH COND - ELDERLY | | | | |

DUR Summary:
PEDIATRICS 0-3 YEARS INDICATES USING CAUTION WITH HYDROCODONE/ACETAMINOPHEN 7.5-325 T

This dosage exceeds the maximum recommended daily dosage for this patient population. Confirm dosage with prescriber.

Drug ID: CYCLOBENZAPRINE 5MG TABLETS

Directions:

AC/HC:

| Type | Severity | Rx # | Rx Date | Overridden |
|---|---|---|---|---|
| DRUG / HLTH COND - ELDERLY | MAJOR | | | Y |
| ADDITIVE TOXICITY/DRUG COCKTAIL | | | | |
| DRUG / HLTH COND - ELDERLY | | | | |

DUR Summary:
ELDERLY IS A POTENTIAL CONTRAINDICATION FOR CYCLOBENZAPRINE 5MG TABLETS CAUTION HIGH ABUSE POTENTIAL! These medications are sometimes combined to create drug cocktails. Concurrent use of opioids, skeletal muscle relaxers and benzodiazepines can cause respiratory depression and excessive sedation.

2500d, 2505d, 2510d, 2515d

| Drug ID: | GLIMEPIRIDE 4MG TABLETS | | | | |
|---|---|---|---|---|---|
| Directions: | | | ACIHC: | | |

| Type | Severity | Rx # | Rx Date | Overridden |
|---|---|---|---|---|
| PERFORM MANUAL DUR - RAMIPRIL 5MG CAPSULES | | | | Y |
| STATIN THERAPY RECOMMENDED | INTERVENTION REQUIRED | | | |
| NO BLOOD GLUCOSE MONITOR | INTERVENTION REQUIRED | | | |
| PERFORM MANUAL DUR ON | | | | |

Statin therapy is recommended as first line therapy for ALL diabetic patients. Please call prescriber to recommend therapy.
All diabetic patients should monitor their blood glucose. Please contact patient for consultation and contact prescriber for prescription.

SYSTEMS, METHODS, AND APPARATUSES FOR GENERATING PHARMACY PRESCRIPTION RECORDS INCLUDING EXCEPTION CASES

TECHNICAL FIELD

The present disclosure relates to systems, methods, and apparatuses for generating pharmacy prescription records. More particularly, the present disclosure relates to systems, methods, and apparatuses for generating pharmacy prescription records including exception cases.

BACKGROUND

Healthcare patients may be prescribed medication by a prescriber (e.g., a medical doctor, a dentist, etc.) to address certain ailments the patient may be suffering. In order to obtain the medication prescribed by the prescriber, the patient must generally have the prescription filled through a pharmacy, either at a medical facility or a retail location. Therefore, the process generally followed by a healthcare patient to fill a prescription includes the patient receiving a prescription from a prescriber, the patient presenting the prescription to a pharmacy, and the pharmacy filling the prescription by identifying the medication described in the prescription and dispensing the medication to the patient. In addition, the pharmacy must provide directions to the patient for taking the medication contents described in the prescription. Rx is an abbreviation for the Latin word meaning "recipe." As an alternative to a patient receiving a printed copy of a prescription, an electronic prescription, for example, may be transmitted directly to a pharmacy. The acronym "eRx" may be, for example, used in conjunction with an electronic prescription.

The food and drug administration (FDA) publishes a list of all drugs that are approved in the United States as safe and effective. The FDA publication is entitled, Approved Drug Products with Therapeutic Equivalence Evaluations (i.e., commonly known as the orange book). In addition to listing all approved drugs, the orange book is also the authoritative source of information on therapeutic equivalence of drug products. In the middle of the past century, many states enacted laws banning substitution of drugs in an attempt to prevent the spread of inferior or counterfeit products. By the 1970s, however, economic pressures had led to the repeal of these anti-substitution laws, and states, beginning with New York, began looking to the federal government for guidance in creating formularies to regulate substitution. In response to such requests, the FDA announced its intention to create a list of approved drugs and therapeutic equivalence determinations. The first edition appeared in October 1980. A new edition is published each year and cumulative supplements are made available on a monthly basis.

Therapeutic equivalency (TE) codes, in the orange book, signify pharmaceutical equivalents that are bioequivalent. Pharmaceutical equivalents are drug products which contain the same active ingredients in the same strength and dosage form delivered by the same route of administration. Bioequivalent drug products are those which have shown comparable bioavailability when studied under similar conditions (e.g., the rate and extent of absorption of a test drug does not significantly differ from that of the reference drug). TE codes are divided into two categories, A-rated drugs and B-rated drugs. A-rated drugs are those drugs which the FDA considers to be therapeutically equivalent and, therefore, substitutable where permitted by the prescriber. B-rated drugs are those drugs which the FDA considers not to be therapeutically equivalent due to actual or potential bioequivalence problems which have not been resolved. Only drug products which are therapeutic equivalents (i.e., "A" rated) may be legally substituted for FDA approved drugs in orange book states, such as New York, without explicit authorization from an associated prescriber.

A Medicare Part D drug list (e.g., a formulary) is a list of drugs covered by a plan. Various formularies are developed to meet the needs of most members based on the most commonly prescribed drugs, including certain prescription drugs that Medicare requires to be covered. Most Medicare drug plans have their own list of covered drugs (i.e., a formulary). A given plan may cover both generic and brand-name prescription drugs. The formulary may include at least two drugs in the most commonly prescribed categories and classes. This helps make sure that people with different medical conditions can get the prescription drugs they need. All Medicare drug plans generally must cover at least two drugs per drug category, but plans can choose which specific drugs they cover. A formulary might not include a specific drug. However, in most cases, a similar drug should be available. If a prescriber (e.g., a doctor or other healthcare provider who is legally allowed to write prescriptions) believes none of the drugs on a plan's formulary will work for an associated patient condition, the patient/prescriber can ask for an exception. The process to obtain this exception may be referred to as a coverage determination that requires prior authorization before payment is approved. A Medicare drug plan can make some changes to its drug list during the year if it follows guidelines set by Medicare. A particular plan may change its drug list during the year because, for example, drug therapies change, new drugs are released, or new medical information becomes available. Plans may immediately remove drugs from their formularies after the Food and Drug Administration (FDA) considers them unsafe or if their manufacturer removes them from the market. Plans meeting certain requirements also can immediately remove brand name drugs from their formularies and replace them with new generic drugs, or they can change the cost or coverage rules for brand name drugs when adding new generic drugs. Many prescription insurance plans include similar formularies.

Electronic medical records (EMRs) are becoming increasingly common in healthcare settings. In addition to storing data related to patient specific history, EMRs are often utilized by a prescriber to generate electronic prescription (eRx) records. EMRs have the potential to reduce instances of medication errors and improve communication between pharmacists and prescribers. However, electronic prescriptions from a physician are often organized in a different format than the pharmacy prescription data necessary for a pharmacist to fill a prescription. Additionally, there are many variations of electronic prescriptions which have different data fields, some providing more detail than others and also which are organized in a variety of ways. The systems currently in place require a technician to read an electronic prescription and manually enter data from the electronic prescription into pharmacy prescription data fields. Once the technician has entered the data from the electronic prescription, a pharmacist can fill the prescription. This manual process can be time consuming, leads to additional work for the technician, and increases the likelihood of errors in the pharmacy prescription data.

Pharmacists are in a unique position among healthcare professionals; pharmacists alone are charged with the responsibility of choosing an appropriate drug product with which to fill a practitioner's prescription. As the drug experts, it is rightfully the pharmacists' duty to perform this task. Pharmacists have been well served in executing this duty by the existence of the FDA orange book. Without the appearance of this resource in 1980, it would have rapidly become impossible for a community pharmacist to keep track of the expanding generic drug market, and impossible to ensure that only therapeutic equivalents would be dispensed to their patients.

Drug utilization reviews are needed that may assist pharmacists in compliance with choosing an appropriate drug product with which to fill a prescription. Drug utilization engines are also needed that may implement the drug utilization reviews.

SUMMARY

A drug utilization engine may include an electronic prescription data receiving module, stored on a memory, that when executed by a processor, may cause the processor to receive electronic prescription data. The electronic prescription data may be representative of prescriber information associated with a prescription for a healthcare patient. The drug utilization engine may also include a payer data receiving module, stored on a memory, that when executed by a processor, may cause the processor to receive payer data. The payer data may be representative of medication formulary information associated with the healthcare patient. The drug utilization engine may further include a prescription comparison module, stored on a memory, that when executed by a processor, may cause the processor to compare the electronic prescription data with the payer data. The drug utilization engine may yet further include a prescription verification module, stored on a memory, that when executed by a processor, may cause the processor to verify that the medication for the healthcare patient is included within the medication formulary based on the comparison of the electronic prescription data with the payer data.

In another embodiment, a computer-readable medium storing a set of computer-readable instructions that, when executed by a processor, may cause the processor to implement a drug utilization review. The computer-readable instructions may include an electronic prescription data receiving module that, when executed by a processor, may cause the processor to receive electronic prescription data. The electronic prescription data may be representative of prescriber information associated with a prescription for a healthcare patient. The computer-readable instructions may also include a payer data receiving module that, when executed by a processor, may cause the processor to receive payer data. The payer data may be representative of medication formulary information associated with the healthcare patient. The computer-readable instructions may further include a prescription comparison module, stored on a memory, that when executed by a processor, may cause the processor to compare the electronic prescription data with the payer data. The computer-readable instructions may yet further include a prescription verification module that, when executed by a processor, may cause the processor to verify that the medication for the healthcare patient is included within the medication formulary based on the comparison of the electronic prescription data with the payer data.

In a further embodiment, a computer-implemented method to implement a drug utilization review may include receiving electronic prescription data at a processor of a computing device in response to the processor executing an electronic prescription data receiving module. The electronic prescription data may be representative of prescriber information associated with a prescription for a healthcare patient. The method may also include receiving payer data at a processor of a computing device in response to the processor executing a payer data receiving module. The payer data may be representative of medication formulary information associated with the healthcare patient. The method may further include comparing, using a processor of a computing device, the electronic prescription data with the payer data in response to the processor executing a prescription comparison module. The method may yet further include verifying that the medication for the healthcare patient is included within the medication formulary based on the comparison of the electronic prescription data with the payer data based on the comparison of the electronic prescription data with the payer data in response to the processor executing a prescription verification module.

BRIEF DESCRIPTION OF THE DRAWINGS

The figures described below depict various aspects of the system and methods disclosed therein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

FIG. 3 depicts an exemplary electronic prescription (eRx);

FIG. 4 depicts a drug utilization rules data including a plurality of medications;

FIGS. 22A and B depict an example drug utilization review for pediatric contraindicated health condition and/or an invalid measurement;

FIGS. 23A and B depict an example drug utilization review to identify an inappropriate dose;

FIGS. 24A and B depict an example drug utilization review to identify a therapeutic duplication;

FIGS. 25A-D depict an example drug utilization review 2500*a-d* may identify a medication therapy to improve a patient outcome;

FIG. 26 depicts an example drug utilization rule 2600 may identify improved patient outcomes; and FIG. 27 depicts an example drug related comments user interface for data review.

DETAILED DESCRIPTION

Figure 1:
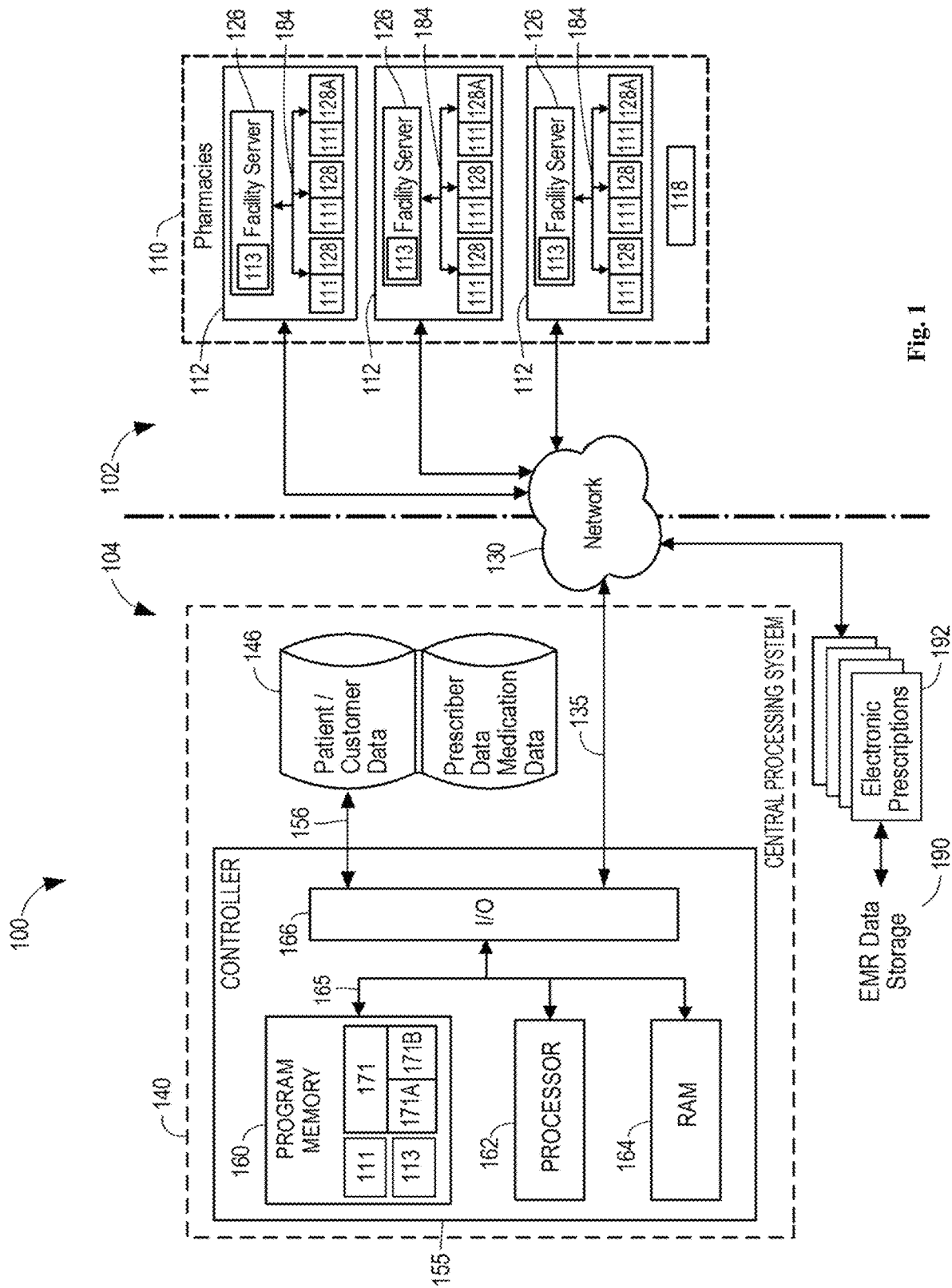
FIG. 1 depicts a block diagram of an exemplary computer system architecture for implementing a prescription processing system.

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

A "health care organization," as used herein, refers to a health care related enterprise or health care provider. The health care organization may be for profit or not-for-profit. The health care organization may provide health care diagnostic, therapeutic, rehabilitation, and other services to patients. For example, the health care organization may provide physician care, therapy, imaging, counseling, or the like. The health care organization may provide inpatient and/or outpatient services, may include one or more physical locations or facilities. Additionally or alternatively, the health care organization may provide other health-care related services, such as providing billing management, providing health care insurance, maintaining electronic medical records, etc. Examples of health care organizations may include a hospital group, a medical practice group, an insurance group, a stand-alone imaging facility, a home-health service provider, and others. In some embodiments, a health care organization may include a pharmacy enterprise.

As used herein, the term "customer" indicates someone purchasing a retail product but may additionally be, by way of example, a patient (i.e., the person named on the prescription), a guardian (e.g., the parent of a child named on the prescription), a care-giver (i.e., anyone who takes care of a patient or picks up the medication on the patient's behalf), etc. Moreover, the term "customer" is not limited to a single person, but may instead be any person or persons having a reason or desire to purchase one or more retail products or to perform one or more functions relating to prescription medications, whether the prescriptions are related to a single patient or multiple patients. For example, a customer could be a caregiver responsible for patients with a specific disease that progresses in a known manner. The caregiver customer might greatly benefit from gaining information related to various medications and health products to assist in his or her caregiver responsibilities. In any event, while the term "customer" may be used interchangeably with the term "patient," in this specification the term "patient" is used primarily so as to avoid confusion.

Generally speaking, an automated pharmacy processing system (also referred to herein as "the system") receives an electronic prescription from a health care organization using electronic medical records (EMRs), electronic health records (EHRs), or standalone e-Prescribing systems. The system automatically converts the information from the electronic prescription into a pharmacy prescription record, which can be filled by a pharmacist at a selected pharmacy location, without requiring a technician to manually enter data from the electronic prescription into the pharmacy processing system. The automated pharmacy processing system may convert patient identification information, prescribing physician (also referred to herein as a "prescriber") identification information, medication information, drug quantity, drug days' supply, prescriber instructions and directions for use (Sig) from an electronic prescription format into the pharmacy prescription record. In addition, the automated pharmacy processing system may determine whether generic substitution of a brand name medication is allowed and substitutes the generic for the brand name medication on the electronic prescription.

Although the automated pharmacy processing system receives the electronic prescriptions via a digital network, the format in which the information or data is stored in an electronic prescription is different from the format in which pharmacy prescription data or records are stored. Therefore, it may be necessary to convert the data in an electronic prescription into a pharmacy prescription record format.

Turning to FIG. 1, a block diagram of an exemplary computer system architecture for implementing a prescription processing system 100 may include both hardware and software applications, as well as various data communications channels for communicating data between the various hardware and software components. The automated pharmacy processing system 100 may be roughly divided into front-end components 102 and back-end components 104. The front-end components 102 are primarily disposed within a retail network 110 including one or more pharmacies 112. The pharmacies 112 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 112 throughout the retail network 110 and executing various pharmacy management-related applications. Pharmacists, technicians, and other pharmacy personnel, referred to collectively herein simply as "pharmacists" (not shown), use the pharmacy workstations 128 to access customer information, enter new prescriptions, access insurance and payment information and so forth. Each of the pharmacies 112 may be, for example, an in-store retail pharmacy, an on-line pharmacy, a mail-order pharmacy, a long-term care pharmacy, a workplace/on-site pharmacy, or a specialty pharmacy. The retail network 110 may also include one or more warehouses or central-filling facilities 118. The warehouses or central-filling facilities 118 may distribute medications or retail products to the various retail pharmacies 112 in the retail network 110, or may distribute medications or retail products directly to customers.

Those of ordinary skill in the art will recognize that the front-end components 102 could also comprise a plurality of facility servers 126 disposed at the plurality of pharmacies 112 instead of, or in addition to, a plurality of pharmacy workstations 128. Each of the pharmacies 112 may include one or more facility servers 126 that may facilitate communications between the workstations 128 of the pharmacies 112 via a digital network 130, and may store information for a plurality of customers/employees/accounts/etc. associated with each facility. Of course, a local digital network 184 may also operatively connect each of the workstations 128 to the facility server 126. Unless otherwise indicated, any discussion of the workstations 128 also refers to the facility servers 126, and vice versa. Moreover, environments other than the pharmacies 112 may employ the workstations 128 and the servers 126. As used herein, the term "pharmacy" refers to any of these environments (e.g., call centers, kiosks, Internet interface terminals, etc.) in addition to the retail pharmacies 112, etc. described above.

The front-end components 102 communicate with the back-end components 104 via the digital network 130. One or more of the front-end components 102 may be excluded from communication with the back-end components 104 by configuration or by limiting access due to security concerns. In some embodiments, the pharmacies 112 may communicate with the back-end components via the digital network 130. In other embodiments, the pharmacies 112 may communicate with the back-end components 104 via the same digital network 130.

Additionally, electronic prescriptions 192 may be transmitted in the form of electronic data files from an EMR data storage entity 190 to the automated pharmacy processing system 100 via the digital network 130. Alternatively, electronic prescriptions 192 may be transmitted from an EHR data storage entity (not shown) or a standalone e-Prescribing data storage entity (not shown). An electronic prescription 192 corresponding to a particular patient may be an electronic data file and may be used in lieu of or in addition to standard paper prescriptions. Information or data stored in an electronic prescription 192 may include, for example, the patient name, the patient address, the patient birth date, the prescriber name, the prescriber license number, the medication name, the quantity, a days' supply, directions for use, specific instructions from the prescriber, etc. Privacy of patients' EMRs may be privacy protected according to local and/or federal government laws and regulations. The EMR data storage entity 190 may include one or more data storage devices of any known non-transitory, tangible, computer-readable storage media technology (e.g., disks, solid state devices, data banks, servers, cloud storage, etc.). The central processing system 140 or the facility servers 126 may receive the electronic prescriptions 192 via the digital network 130.

The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol. The back-end components 104 include the central processing system 140 within a central processing facility, such as, for example, the central processing facility described in U.S. Pat. No. 8,175,891 entitled "DISTRIBUTED PHARMACY PRESCRIPTION PROCESSING SYSTEM" the entire disclosure of which is incorporated by reference herein. Of course, the pharmacies 112 may be communicatively connected to different back-end components 104 having one or more functions or capabilities that are similar to the central processing system 140. The central processing system 140 may include one or more computer processors 162 adapted and configured to execute various software applications and components of the new prescription order system 100, in addition to other software applications.

The central processing system 140 further includes a database 146. The database 146 is adapted to store data related to the operation of the automated pharmacy processing system 100 (e.g., patient profile data, physician profile data as well as medication data, etc.). In some embodiments, the database 146 may include the pharmacy patient database 200, the pharmacy prescriber database 146 and the pharmacy medication database. The central processing system 140 may access data stored in the database 146 when executing various functions and tasks associated with the operation of the new prescription order system 100. For simplicity, FIG. 1 illustrates the database 146 as only one instance of a database. However, the database 146 according to some implementations includes a group of one or more databases, each storing different information. For example, one database may store patient profile data while another may store physician profile data. For the purposes of this discussion, the term "database" 146 may refer to an individual database or to a group of two or more databases.

Although FIG. 1 depicts the automated pharmacy processing system 100 as including the central processing system 140 in communication with three pharmacies 112, it should be understood that different numbers of processing systems and pharmacies may be utilized. For example, the digital network 130 (or other digital networks, not shown) may interconnect the central processing system 140 to a plurality of included central processing systems 140 and hundreds of pharmacies 112. According to the disclosed example, this configuration may provide several advantages, such as, for example, enabling near real-time uploads and downloads of information as well as periodic uploads and downloads of information. This provides for a primary backup of all the information generated in the automated pharmacy process. Alternatively, some of the pharmacies 112 may store data locally on the facility server 126 and/or the workstations 128.

FIG. 1 also depicts one possible embodiment of the central processing system 140. The central processing system 140 may have a controller 155 operatively connected to the database 146 via a link 156 connected to an input/output (I/O) circuit 166. It should be noted that, while not shown, additional databases may be linked to the controller 155 in a known manner. The controller 155 includes a program memory 160, the processor 162 (may be called a microcontroller or a microprocessor), a random-access memory (RAM) 164, and the input/output (I/O) circuit 166, all of which are interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example. A link 135 may operatively connect the controller 155 to the digital network 130 through the I/O circuit 166.

The program memory 160 may also contain machine-readable instructions (i.e., software) 171, for execution by the processor 162. The software 171 may perform the various tasks associated with operation of the pharmacy or pharmacies, and may be a single module 171 or a plurality of modules 171A, 171B. While the software 171 is depicted in FIG. 1 as including two modules, 171A and 171B, the software 171 may include any number of modules accomplishing tasks related to pharmacy operation including, for example, receiving prescription orders, managing prescription workflow, etc. In some embodiments, the software 171 may include instructions for implementing the exemplary systems, methods, drug utilization rules, and drug utilization engines described herein. The central processing system 140 implements a server application 113 for providing data to a user interface application 111 operating on the workstations 128.

As described above, the database 146, illustrated in FIG. 1, includes various information about the pharmacy's customers, prescribing physicians, and prescription medications. Customer records are among the exemplary data that the automated pharmacy processing system 100 may store on the database 146. A customer record contains important information about the customer and the various pharmacy services that have been invoked by, or on behalf of, the customer in a customer profile. The customer profile includes basic biographical information about the customer, such as a customer name, a customer social security number, a customer address, a customer phone number, a customer birth date, customer prescription history, customer allergies, customer insurance information etc. Prescribing physician records may also be stored on the database 146. Prescribing physician records may include a prescriber name, a practice name, a prescriber DEA number, a prescriber phone number, a prescriber office address, etc. The database 146 may also store a list of predetermined prescriber instruction components. Moreover, prescription medication records may include a medication name, a quantity of the medication, a generic equivalent, whether the medication is a controlled substance, a Dispense as Written (DAW) code, a National Drug Code (NDC), etc.

Figure 2:
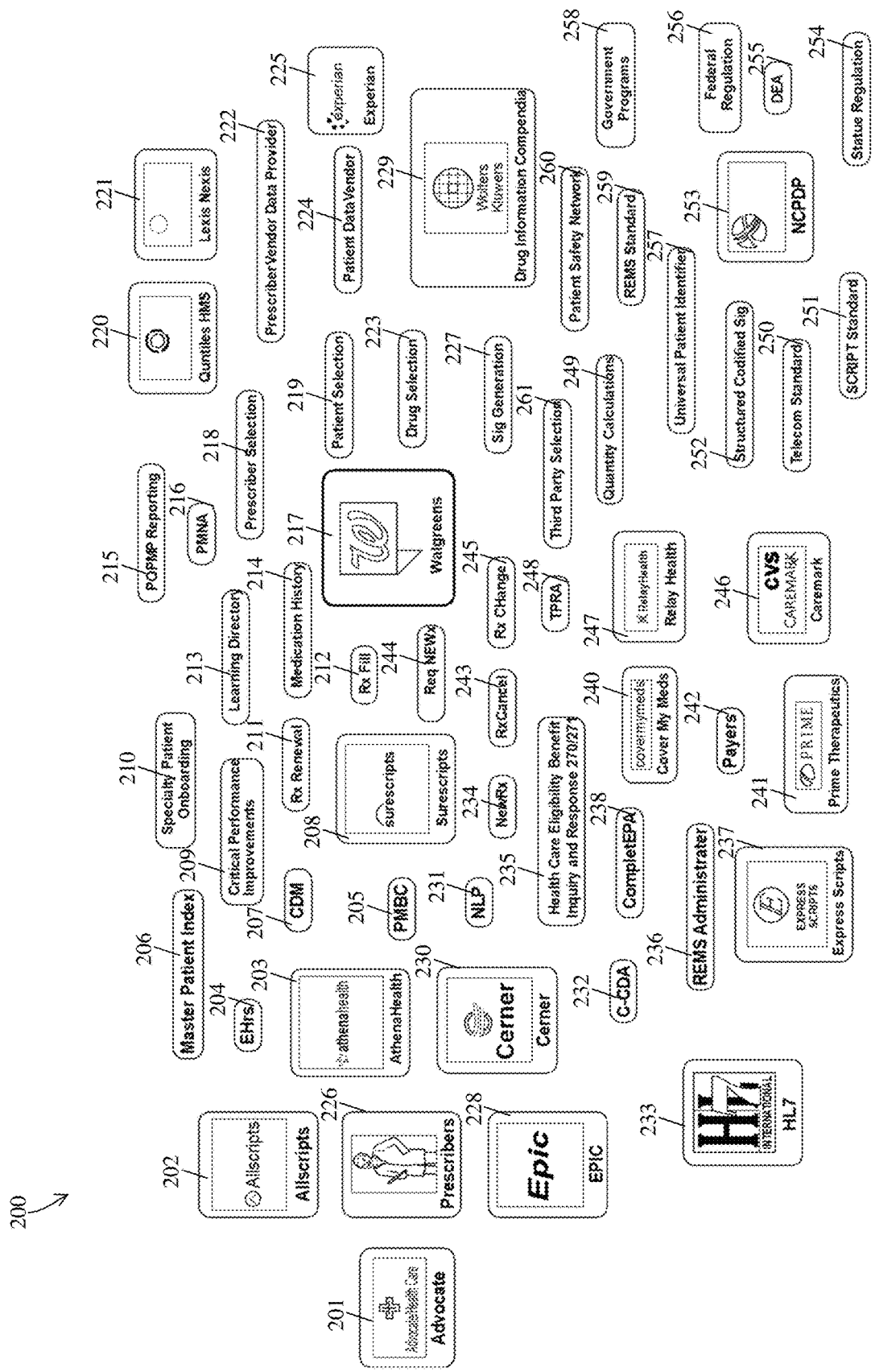
FIG. 2 depicts a high-level block diagram of an example healthcare data source, data transmission, and data reception structure.

With reference to FIG. 2, a high-level block diagram of a healthcare data source, data transmission, and data reception structure 200 may include at least one of: a prescriber (e.g., Advocate) healthcare system 201, an EMR (e.g., Allscripts) data source 202, an EMR (e.g., Athena Health) data source 203, an electronic health records (EHRs) data source 204, a patient medication benefit check (PMBC) data source 205, a master patient index data source 206, a customer data management (CDM) data source 207, a Surescripts data source 208, a critical performance improvements data source 209, a special patient onboarding (SPO) data source 210, a pharmacy dispensing system (Rx renewal) data source 211, a Rx fill method of interchanging electronic information 212, a learning directory data source 213, a medication history data source 214, a prescription drug prescription monitoring program (PDPMP) reporting data source 215, a primary medication non-adherence (PMNA) data source 216, a pharmacy (e.g., Walgreens) data source 217, a prescriber selection data source 218, a patient selection data source 219, a prescriber (e.g., Quintiles IMS (or IQVIA)) data source 220, a prescriber (e.g., Lexis Nexis) data source 221, a prescriber vendor data provider data source 222, a drug selection (e.g., orange book) data source 223, a patient data vendor data source 224, a patient data vendor (e.g., Experian) data source 225, a Prescribers data source 226, a prescriber's instruction (e.g., a Sig) generation data source 227, an EHR (e.g., Epic) data source 228, a drug information compendia (e.g., Wolters Kluwer) data source 229, an EHR (e.g., Cerner) data source 230, a natural language processor (NLP) (e.g., a Stanford University NLP, a Walgreens NLP, etc.) data source 231, a consolidated clinical document architecture (C-CDA) data source 232, a HL7 International data source 233, a NewRx method of exchanging electronic health information 234, a healthcare eligibility benefit inquiry and response 270/271 data source 235, a risk evaluation and mitigation strategy (REMS) data source 236, an Pharmacy Prescription Benefit Manager (PBM) (e.g., Express Scripts, Cigna) data source 237, a patient insurance formulary tool (e.g., CompletEPA) data source 238, a method to electronically obtain prior authorizations (e.g., cover my meds) data source 240, a PBM (e.g., Prime Therapeutics) data source 241, a payers (e.g., a prescription insurance company) data source 242, a Rx Cancel method of electronic health information exchange 243, a request new Rx method of electronic health information exchange 244, a Rx change method of electronic health information exchange 245, a PBM (e.g., CareMark CVS) data source 246, a RelayHealth data source 247, a third party rejection automation (TPRA) data source 248, a quality calculations data source 249, an industry-wide standard for communicating electronic prescription claims (Telecom) data source 250, an industry-wide standard for communicating electronic prescription (SCRIPT) data source 251, a structure codified Sig (e.g., a Walgreens) data source 252, a national council for prescription drug programs (NCPDP) source of pharmacy industry technology standards 253, a state regulation data source 254, a drug enforcement agency (e.g., DEA) data source 255, a federal regulation data source 256, a universal patient identifier data source 257, a government programs (e.g., Medicare, Medicaid, WIC, etc.) data source 258, a REMS standard data source 259, a patient safety network data source 260, a third party selection data source 261, any sub-combination thereof, or a combination thereof. The healthcare data source, data transmission, and data reception structure 200 may also include a prescription drug monitoring program (PDMP) data source, a clinical document architecture (CDA) data source, a fast healthcare interoperability resources (FHIR) data source, a national record locator service (e.g., NRLS) data source, a specialty patient onboarding (SPO) data source, and/or a healthcare accounts receivable (HAR) data source. Any of the data sources 201-261 of FIG. 2 may be, for example, stored in a database (e.g., database 146 of a central processing system 140 of FIG. 1).

A "special patient" may be determined based on, for example, a prescribed medication. For example, with respect to Bupropion (Zyban), special patient groups may include: children and adolescents, elderly individuals, hepatically impaired individuals, renally impaired individuals, psychiatric individuals, pregnant or lactating women, individuals that are predisposed towards seizure, and individuals with eating disorders. Drug utilization rules for Bupropion (Zyban) may include: children and adolescents, not recommended in patients under 18 yrs of age; elderly, use with caution, increased sensitivity may be an issue (more likely to have decreased renal function), 150 mg once daily is recommended; hepatically impaired individuals, contraindicated in patients with severe hepatic cirrhosis (reduced clearance leading to high plasma levels), use with caution in mild-to-moderate hepatic impairment, which may lead to higher levels, 150 mg daily is recommended, monitor closely for possible undesirable effects (e.g., insomnia, dry mouth, seizures) indicating high drug metabolite levels; renally impaired individuals, use with caution, 150 mg once daily recommended, monitor closely for possible undesirable effects (e.g., insomnia, dry mouth, seizures) indicating high drug metabolite levels; psychiatric individuals, contraindicated in patients with a history of bipolar disorder, may precipitate psychotic episodes in susceptible patients, use with caution; pregnant or lactating women, Zyban must not be used in pregnancy/lactation, if pharmacotherapy is required consider NRT, which is also contraindicated in some products, but safer than smoking in pregnancy; individuals that are predisposed towards seizure, contraindicated in patients with current or previous seizure disorder, use with extreme caution in patients with certain conditions including: a history of brain trauma, brain injury, concomitant administration of medicines known to lower the seizure threshold (e.g., antipsychotics, antidepressants such as SSRIs, theophylline, systemic steroids, etc.), also use with caution in circumstances of: alcohol abuse, abrupt withdrawal from alcohol/benzodiazepines, diabetes treated with hypoglycaemics/insulin (reduce dose to 150 mg per day), use of stimulants/anorectic products; and individuals with eating disorders, contraindicated in patients with current or previous diagnosis of bulimia or anorexia nervosa. Sensitivity may require the medication to be contraindicated in patients with current hypersensitivity to Zyban or excipients in the tablets (excipients do not include lactose). Discontinue if patient experiences hypersensitivity or anaphylactic reactions (e.g., rash, pruritus, urticaria, chest pain, oedema or dyspnea).

Turning to FIG. 3, an exemplary electronic prescription (eRx) 300 for a particular patient 102 is illustrated. This is merely an example and electronic prescriptions may be formatted in any suitable number of ways. Electronic prescribing (e-prescribing or eRx) is the computer-based electronic generation, transmission, and filling of a medical prescription, taking the place of paper, verbal and faxed prescriptions. E-prescribing allows a physician, nurse practitioner, or physician assistant (prescribers) to use digital prescription software to electronically transmit a new prescription or renewal authorization to a community or mail-order pharmacy. It outlines the ability to send error-free, accurate, and understandable prescriptions electronically from the healthcare provider to the pharmacy. E-prescribing is meant to reduce the risks associated with traditional prescription script writing. It is also one of the major reasons for the push for electronic medical records. By sharing medical prescription information, c-prescribing seeks to connect the patient's team of healthcare providers to facilitate knowledgeable decision making. According to NCPDP Electronic Prescribing Standards, a "qualified" e-prescribing system must be capable of performing all of the following functions: patient identification; generating a complete active medication list, possibly incorporating electronic data received from an insurance provider; access to patient historical data; prescribe or add new medication and select the pharmacy where the prescription will be filled; work with an existing medication within the practice, this can involve viewing details of a medication, remove a medication from the active medication list, change dose, etc., for a medication or renew one or more medications; printing prescriptions; electronically transmitting prescriptions to a transaction hub; conducting all safety checks using an integrated decision support system (often known as a Drug Utilization Review); safety checks (i.e., automated prompts that offer information on the drug being prescribed, potential inappropriate dose or route of administration, drug-drug interactions, allergy concerns, or warnings of caution, etc.); flagging availability of lower cost, therapeutically appropriate alternatives (if any); providing information on formulary or tiered formulary medications, patient eligibility, and authorization requirements received electronically from the patient's insurance provider; system integration capabilities (e.g., connection with various databases, connection with pharmacy and pharmacy benefit manager systems); and educational capabilities (e.g., patient education, provider feedback).

Although the automated pharmacy processing system 100 may receive electronic prescriptions via a digital network, the format in which the information or data is stored in an electronic prescription is often different from the format in which pharmacy prescription data or records are stored. Therefore, it may be necessary to convert the data in an electronic prescription into a pharmacy prescription record format. In the example of FIG. 3, the electronic prescription 100 includes several data fields which may be grouped into multiple prescription components for the automated pharmacy processing system. The prescription components include patient information, prescriber information, medication name information, quantity and days' supply and prescriber instructions.

For example, a patient name field 302, a patient age field 304, and a patient address field 308 may fit within the patient information component. On the other hand, a prescriber name field 316, a DEA registration field 318, a prescriber license number field 320, a prescriber phone number field 322, and a prescriber facility field 324 may fit within the prescriber information component. Electronic prescription data which may fit within the medication name information component includes a medication name 310, a medication quantity 330 and a dispense as written (DAW) field 326 which is used to determine whether a generic substitute is permitted. Additionally, a number of days field 328 and a dispense (DISP) field 314 may fit within the days' supply and quantity components, respectively, while a prescriber directions (Sig) field 312 may fit within the prescriber instructions component. The electronic prescription 300 may also include an indication of a pharmacy location for the patient to pick up the prescription. Alternatively, the pharmacy location may default to the closest location to the patient address 308.

An automated pharmacy processing system 100 may detect data by parsing the electronic prescription 300 to find field identifiers and XML tags corresponding to data fields. For example, the electronic prescription 300 may follow the SCRIPT 251 standard defined and maintained by the National Council for Prescription Drug Programs (NCPDP) 253, which defines field identifiers and XML tags for each data field. For example, the system may parse the electronic prescription 300 for an XML tag or field identifier indicating a DEA 255 registration field. However, this is merely one example of how data within an electronic prescription may be detected and categorized by the automated pharmacy processing system. Alternatively, data may be detected and categorized in any suitable number of ways and in some implementations data from the electronic prescription may not be categorized. For ease of illustration only, this application will continue to describe detecting data from an electronic prescription in the manner described above.

With reference to FIG. 4, drug utilization review data 400 may include a plurality of medications 405. Each medication 405 may be correlated with a respective rule 415 and a respective message 410. For example, the medication AURO 405 is intended for ear wax removal. Accordingly, if an eRx (e.g., prescription 300 of FIG. 3) includes, for example, a Sig 112 that indicates anything to do with administering the medication in a patient's eye 415, implementation of the respective rule 400 may, for example, result in a message "Ear Wax Removal Drops cannot be use in the eye! Check route of administration." Accordingly, implementation of the rule 400 for the medication AURO 405 may identify that the eRx 300 includes an inappropriate route of administration within a respective prescriber instructions 112. Similar quality alert rules and drug comments may be included. Audit rules may be slightly more complicated and may, for example, involve medication dosing, patient age ranges, health conditions, drug-drug interactions, drug-genotype interactions etc.

Figure 5A:
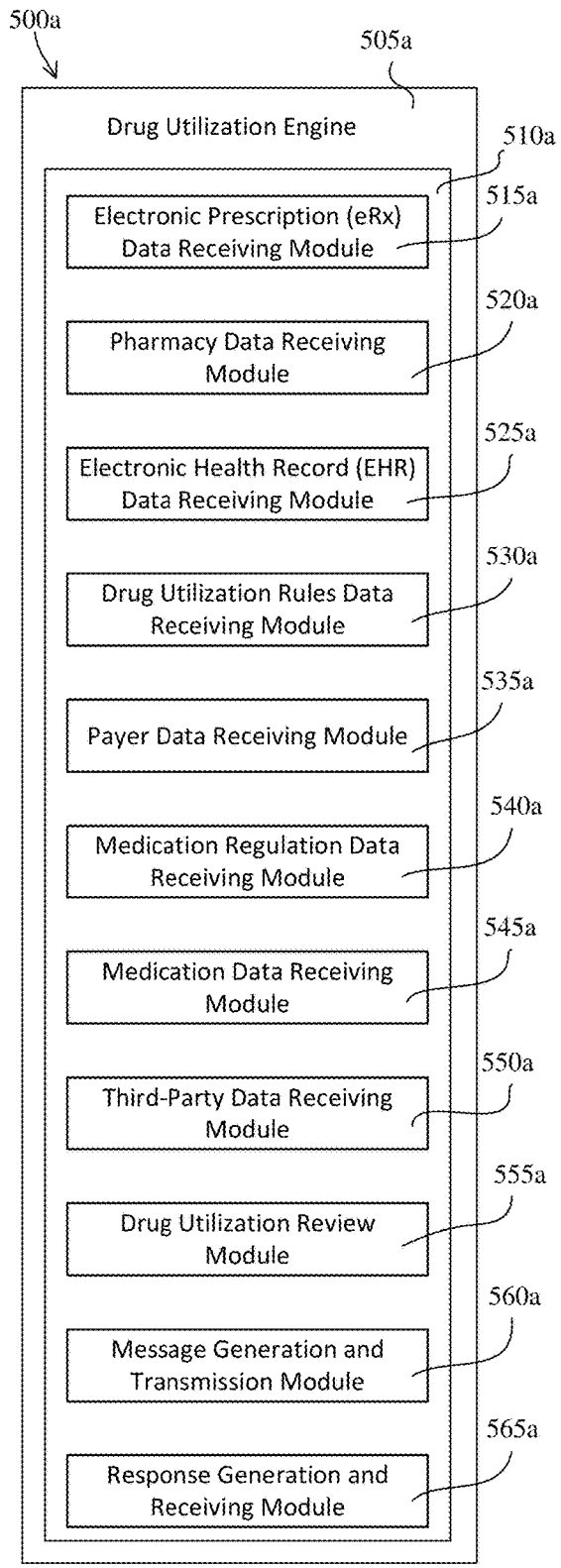
FIG. 5A depicts an example computer system for implementing a prescription processing system.

Turning to FIG. 5A, computer system for implementing a prescription processing system 500a may include a drug utilization engine 505a. The drug utilization engine 505a may be similar to, for example, any one of a controller (e.g., controller 155 of FIG. 1), a workstation (e.g., workstation 128 of FIG. 1), or a combination thereof. In any event, the drug utilization engine 505a may include an electronic prescription (eRx) data receiving module 515a, a pharmacy data receiving module 520a, an electronic health record (EHR) data receiving module 525a, a drug utilization review (DUR) data receiving module 530a, a payer data receiving module 535a, a medication regulation data receiving module 540a, a medication data receiving module 545a, a third-party data receiving module 550a, a drug utilization review module 555a, a message generation and transmission module 560a, and a response generation and receiving module 565a, for example, stored on a memory 510a as a set of computer-readable instructions. The memory 510a may be similar to, for example, the memory 160 of FIG. 1. Alternatively, any one of the modules 515a-565a may be configured as a dedicated hardware device (e.g., an application specific integrated circuit (ASIC), a logic circuit, an electrical circuit made up of discrete components, a field programmable gate array (FPGA), a sub-combination thereof, or a combination thereof, etc.).

Figure 5B:
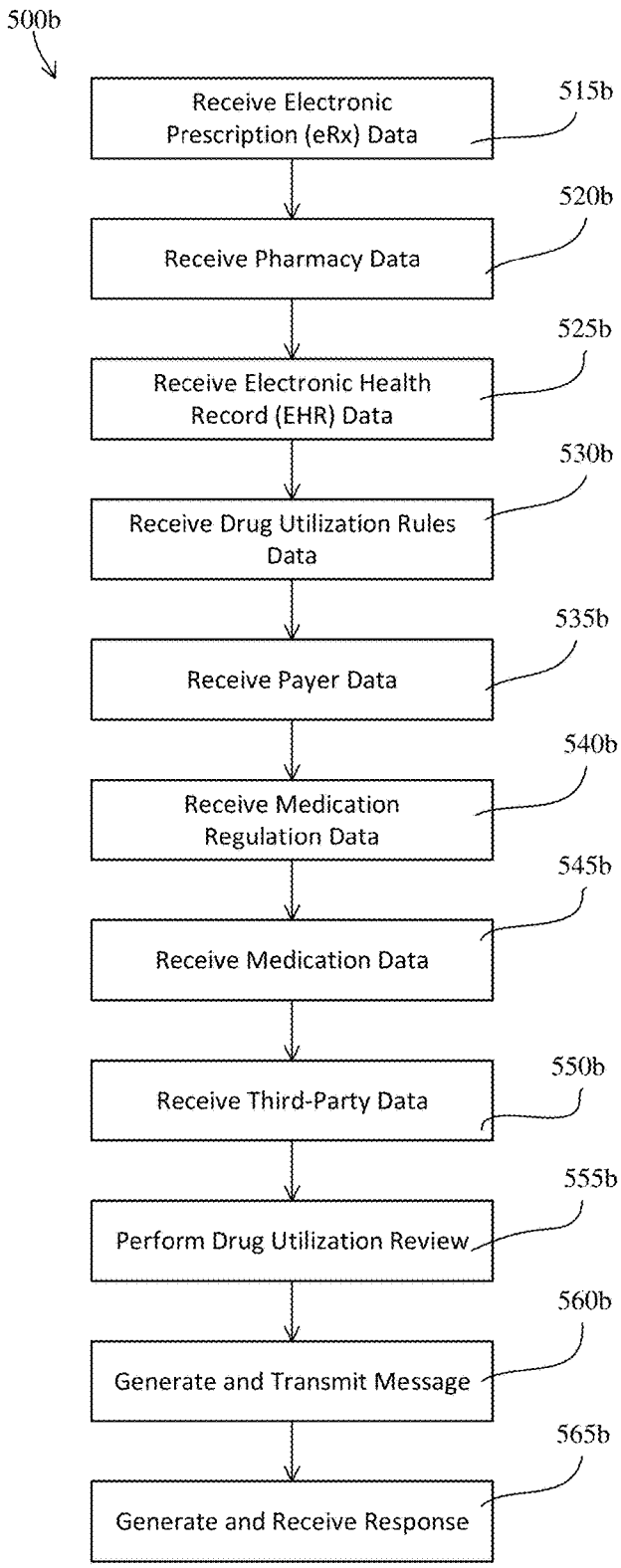
FIG. 5B depicts an example computer implemented method for performing a drug utilization review.

With reference to FIG. 5B, a computer implemented method for performing a drug utilization review 500b may be implemented by, for example, the drug utilization engine 505a. In particular, a processor (e.g., processor 162 of FIG. 1) may execute the electronic prescription (cRx) data receiving module 515a to, for example, cause the processor 162 to receive eRx data (block 515b). For example, the processor 162 may receive eRx data from a prescriber (e.g., a doctor, a dentist, a medical professional, etc.) via an electronic health records system (e.g., EHRs 204, prescribers 226 of FIG. 2, a prescriber vendor data provider 224 of FIG. 2, etc.). The eRx data may include, for example, a healthcare patient name 102, a healthcare patient age 104, a healthcare patient address 108, a medication 110, a prescriber direction (Sig) 112 (e.g., a route of administration, a dosage of the medication, a frequency for taking the medication, etc.), a time frame for which the prescription is valid 114, a prescriber name 116, a prescriber DEA registration 118, a prescriber license #120, a prescriber telephone number 122, a prescriber facility 124, a dispense as written (DAW) indication 126, a prescription coverage period 128, and a medication dosage 130.

The processor 162 may execute the pharmacy data receiving module 520a to, for example, cause the processor 162 to receive pharmacy data (block 520b). For example, the processor 162 may receive pharmacy data from a pharmacy (e.g., Walgreens 217 of FIG. 2). The pharmacy data may include, for example, a name of the pharmacy, a pharmacy address, a pharmacy telephone number, a name of a pharmacist, a recommendation for an alternate medication, an indication of whether a medication is covered by a formulary of a patient, a message to a prescriber generated by a drug utilization review, a message to a patient, etc.

The processor 162 may execute the electronic health record (EHR) data receiving module 525a to, for example, cause the processor 162 to receive EHR data (block 525b). For example, the processor 162 may receive EHR data from EHRs 204 of FIG. 2. Surescripts 208 of FIG. 2, etc. The EHR data may, for example, include healthcare patient personal information (e.g., a name, an age, a gender), a patient physical health history, patient allergies, a patient mental health history, a patient medication history 214 of FIG. 2, whether the patient is a "special" patient, whether the patient is pregnant, a list of medications for which a patient has a current prescription, etc.

Alternatively, or additionally, the EHR data may include data related to a group of healthcare patients. For example, the EHR data may be representative of a group of healthcare patients similar to a healthcare patient for which a drug utilization review is being performed. The EHR data may be, for example, representative of a bell-shaped curve for a given medication (i.e., a given prescription) for the group of similar patients (e.g., is the prescribed dosage for the given healthcare patient similar to a prescribed dosage for the group, is the frequency of administration for the given healthcare patient similar to a frequency for the group, etc.).

The processor 162 may execute the drug utilization review (DUR) data receiving module 530a to, for example, cause the processor 162 to receive DUR data (block 530b). For example, the processor 162 may receive DUR data from a pharmacy (e.g., Walgreens 217 of FIG. 2, etc.), a drug information compendia 229 of FIG. 2, a learning directory 213 of FIG. 2, a DUR rule set 400 of FIG. 4, etc. Additionally, or alternatively, the drug utilization rules may be received from a prescriber (e.g., Advocate healthcare) data source 201, an EMR (e.g., Allscripts) data source 202, an EMR (e.g., Athena Health) data source 203, an electronic health records (EHRs) data source 204, a patient medication benefit check (PMBC) data source 205, a master patient index data source 206, a customer data management (CDM) data source 207, a Surescripts data source 208, a critical performance improvements data source 209, a special patient onboarding (SPO) data source 210, a pharmacy dispensing system (e.g., Rx renewal) data source 211, a Rx fill method of exchanging electronic health information 212, a learning directory prescriber data source 213, a medication history data source 214, a prescription drug prescription monitoring program (PDPMP) reporting data source 215, a primary medication non-adherence (PMNA) data source 216, a pharmacy (e.g., Walgreens) data source 217, a prescriber selection data source 218, a patient selection data source 219, a (e.g., Quintiles IMS (or IQVIA)) data source 220, a prescriber (e.g., Lexis Nexis) data source 221, a prescriber vendor data provider data source 222, a drug selection (e.g., orange book) data source 223, a patient data vendor data source 224, a patient (e.g., Experian) data source 225, a Prescribers data source 226, a prescriber's direction (e.g., a Sig) generation data source 227, an EHR (e.g., Epic) data source 228, a drug information compendia (e.g., Wolters Kluwer) data source 229, an EHR (e.g., Cerner) data source 230, a natural language processing (NLP) (e.g., a Stanford University NLP, a Walgreens NLP, etc.) data source 231, a consolidated clinical document architecture (C-CDA) data source 232, a HL7 International data source 233, a NewRx method of exchanging electronic health information 234, a healthcare eligibility benefit inquiry and response 270/271 data source 235, a risk evaluation and mitigation strategy (REMS) data source 236, a payer (e.g., Express Scripts (Cigna)) data source 237, a method of requesting prior authorization approval (e.g., CompletEPA) data source 238, method of requesting prior authorization approval (e.g., CoverMyMeds) data source 240, a payer (e.g., Prime Therapeutics data source 241, a payers (e.g., a prescription insurance company) data source 242, a Rx Cancel method of exchanging electronic health information 243, a request new Rx method of exchanging electronic health information 244, a Rx change method of exchanging electronic health information 245, a payer (e.g., CareMark CVS) data source 246, a RelayHealth data source 247, a third party risk assessment (TPRA) data source 248, a quality calculations data source 249, a telecom standard data source 250, a SCRIPT standard data source 251, a structure codified Sig (e.g., a Walgreens) data source 252, a national council for prescription drug programs (NCPDP) data source 253, a state regulation data source 254, a drug enforcement agency (DEA) data source 255, a federal regulation data source 256, a universal patient identifier data source 257, a government programs (e.g., Medicare, Medicaid, WIC, etc.) data source 258, a REMS standard data source 259, a patient safety network data source 260, a third party selection data source 261 a prescription drug monitoring program (PDMP) data source, a clinical document architecture (CDA) data source, a fast healthcare interoperability resources (FHIR) data source, a source of patient-prescriber electronic health records (e.g., national record locator system (NRLS)) data source, a method of exchanging specialty patient information (e.g., Specialty Patient Onboarding) (SPO) data source, a healthcare accounts receivable (HAR) data source, any sub-combination thereof, or a combination thereof.

The processor 162 may execute the payer data receiving module 535a to, for example, cause the processor 162 to receive payer data (block 535b). For example, the processor 162 may receive payer data from payers 242 of FIG. 2, etc. The payer data may be, for example, representative of a formulary from an insurance company, a deductible for a patient, a maximum amount that will be paid to a pharmacy, a maximum amount that will be paid for a particular medication, etc.

The processor 162 may execute the medication regulation data receiving module 540a to, for example, cause the processor 162 to receive medication regulation data (block 540b). For example, the processor 162 may receive medication regulation data from a federal regulation data source 256 of FIG. 2, a drug enforcement regulation data source 255 of FIG. 2, a state regulation data source 254 of FIG. 2, etc. The medication regulation data may be, for example, representative of Approved Drug Products with Therapeutic Equivalence Evaluations (i.e., commonly known as the orange book), drug distribution regulations (e.g., regulations related to schedule 1 drugs, regulations related to opioids, etc.).

The processor 162 may execute the medication data receiving module 545a to, for example, cause the processor 162 to receive medication data (block 545b). For example, the processor 162 may receive medication data from learning directory 213 of FIG. 2, a drug information compendia 229 of FIG. 2, a patient safety network 260 of FIG. 2, etc. The medication data may be, for example, representative of therapeutic equivalency (TE) codes (e.g., TE codes in the orange book that signify pharmaceutical equivalents that are bioequivalent), pharmaceutical equivalents drug products which contain the same active ingredients in the same strength and dosage form delivered by the same route of administration, bioequivalent drug products that have shown comparable bioavailability when studied under similar conditions (e.g., the rate and extent of absorption of a test drug does not significantly differ from that of the reference drug), etc.

The processor 162 may execute the third-party data receiving module 550a to, for example, cause the processor 162 to receive third-party data (block 550b). The processor 162 may, for example, receive third-party data from a prescriber system (e.g., Advocate healthcare) data source 201, an EMR (e.g., Allscripts) data source 202, an EMR (e.g., Athena Health) data source 203, an electronic health records (EHRs) data source 204, a patient medication benefit check (PMBC) data source 205, a master patient index data source 206, a Customer Data Management (CDM) data source 207, a Surescripts data source 208, a critical performance improvements data source 209, a special patient onboarding (SPO) data source 210, a pharmacy dispensing system (e.g., Rx renewal) data source 211, a Rx fill method of exchanging health information 212, a learning directory data source 213, a medication history data source 214, a prescription drug prescription monitoring program (PDPMP) reporting data source 215, a primary medication non-adherence (PMNA) data source 216, a pharmacy (e.g., Walgreens) data source 217, a prescriber selection data source 218, a patient selection data source 219, a prescriber (e.g., Quintiles IMS (or IQVIA)) data source 220, a prescriber (e.g., Lexis Nexis) data source 221, a prescriber vendor data provider data source 222, a drug selection (e.g., orange book) data source 223, a patient data vendor data source 224, (e.g., Experian) data source 225, a Prescribers data source 226, a prescriber's directions for use (e.g., a Sig) generation data source 227, an EHR (e.g., Epic) data source 228, a drug information compendia (e.g., Wolters Kluwer) data source 229, an EHR (e.g., Cerner) data source 230, a natural language processing (NLP) (e.g., a Stanford University NLP, a Walgreens NLP, etc.) data source 231, a consolidated clinical document architecture (C-CDA) data source 232, a HL7 International data source 233, a NewRx method of exchanging electronic health information 234, a healthcare eligibility benefit inquiry and response 270/271 data source 235, a risk evaluation and mitigation strategy (REMS) data source 236, a payer (e.g., Express Scripts (Cigna)) data source 237, a prior authorization request tool (e.g., CompletEPA) data source 238, a a prior authorization request tool (e.g., CoverMyMeds) data source 240, a payer (e.g., Prime Therapeutics) data source 241, a payers (e.g., a prescription insurance company) data source 242, a Rx Cancel method of exchanging electronic health information 243, a request new Rx method of exchanging electronic health information 244, a Rx change method of exchanging electronic health information 245, a payer (e.g., CareMark CVS) data source 246, a RelayHealth data source 247, a third party risk assessment (TPRA) data source 248, a quality calculations data source 249, a telecom standard data source 250, a SCRIPT standard data source 251, a structure codified Sig (e.g., a Walgreens) data source 252, a national council for prescription drug programs (NCPDP) data source 253, a state regulation data source 254, a drug enforcement agency (DEA) data source 255, a federal regulation data source 256, a universal patient identifier data source 257, a government programs (e.g., Medicare, Medicaid, WIC, etc.) data source 258, a REMS standard data source 259, a patient safety network data source 260, a third party selection data source 261 a prescription drug monitoring program (PDMP) data source, a clinical document architecture (CDA) data source, a fast healthcare interoperability resources (FHIR) data source, a national reporting and learning system (NRLS) data source, a method of exchanging electronic health information (e.g., Specialty Patient Onboarding (SPO)) data source, a healthcare accounts receivable (HAR) data source, any sub-combination thereof, or a combination thereof.

The processor 162 may execute the drug utilization review module 555a to, for example, cause the processor 162 to determine whether a prescription complies with drug utilization rules (block 555b). For example, the processor 162 may compare an electronic prescription data and/or electronic health record data to drug utilization data. The processor 162 may, for example, execute the drug utilization review module 55a to identify an inappropriate route of administration, an inappropriate unit of measure, an inappropriate prescriber instruction (with correct dose (DOS)), a duplicate therapy, a maximum medication dosage exceeded, a health condition contraindication, an inappropriate drug cocktail, additive toxicity, undesirable outcomes, an undesirable impact on adherence, any sub-combination thereof, or a combination thereof. A drug utilization engine 505a may implement the drug utilization rules to, for example, automatically perform a drug utilization review 500b for a given patient. As a particular example, a drug utilization engine 505b may distinguish a "total daily dosage" from a product of an "individual dosage" and a "dosage frequency."

The processor 162 may, for example, generate an output of a drug utilization review that is binary (i.e., the comparison produces either a "positive" or a "negative" result). Alternatively, the processor 162 may implement, for example, a probability function to generate an output of a drug utilization review that is representative of a probability of whether the comparison is "positive" or "negative.

The processor 162 may execute the message generation and transmission module 560a to, for example, cause the processor 162 to generate and/or transmit a message (block 560b). For example, the processor 162 may generate and transmit a message to a prescriber and/or a patient. The processor 162 may generate and transmit a message according to an electronic health records format (e.g., a F1 key of electronic health records, etc.). The processor 162 may, for example, generate a message based upon an output of a drug utilization review module 555a.

The processor 162 may execute the response generation and receiving module 565a to, for example, cause the processor 162 to generate and/or receive a response (block 565b). For example, the processor 162 may generate and/or transmit a response based on a message that was generated based upon an output of a drug utilization review module 555a.

Figure 6:
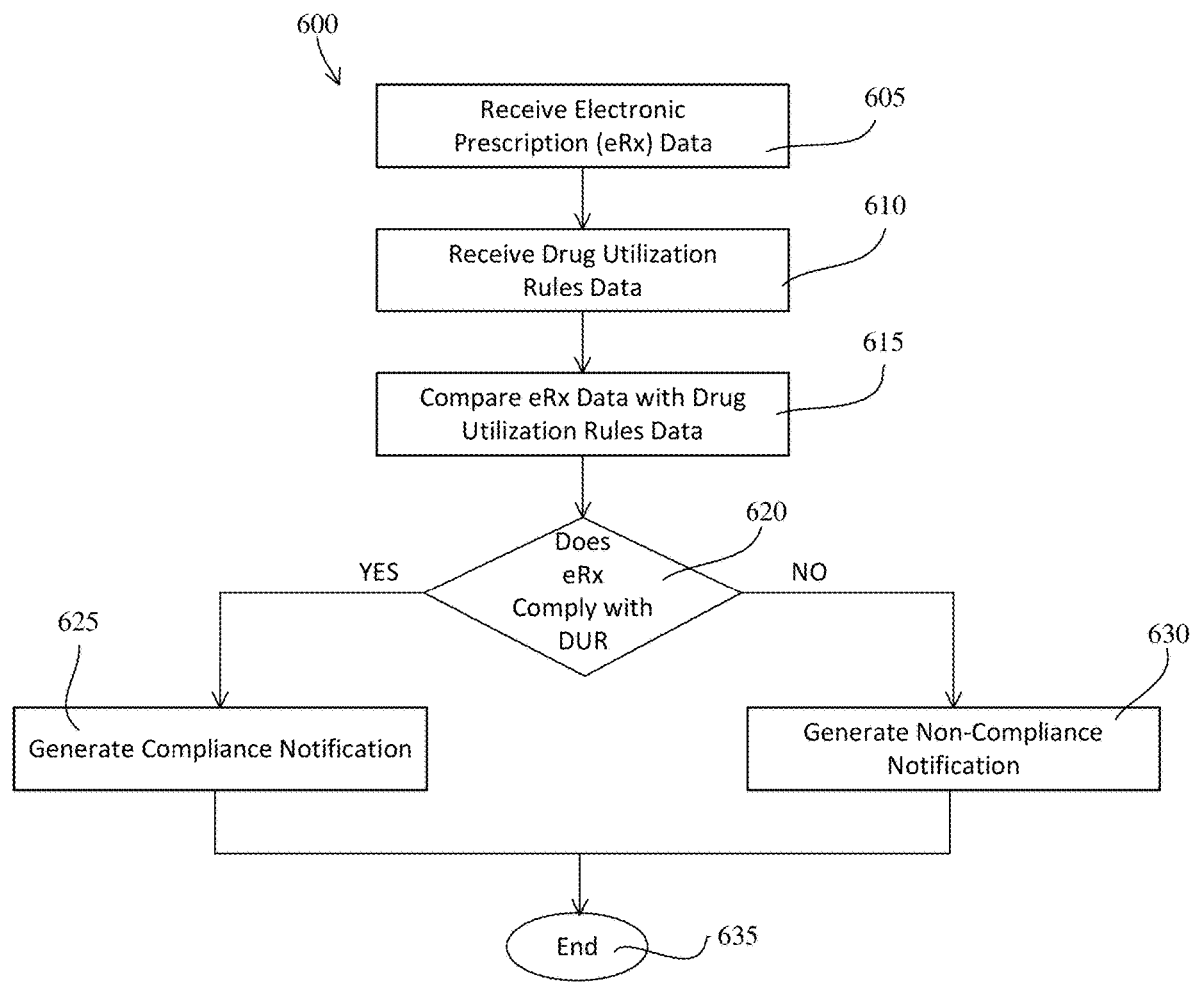
FIG. 6 depicts an example computer implemented method of performing a drug utilization review.

Turning to FIG. 6, a computer implemented method of performing a drug utilization review 600 may be implemented by, for example, the drug utilization engine 505a. In particular, a processor (e.g., processor 162 of FIG. 1) may execute the electronic prescription (eRx) data receiving module 515a to, for example, cause the processor 162 to receive eRx data (block 605). The processor 162 may execute the drug utilization review (DUR) data receiving module 530a to, for example, cause the processor 162 to receive DUR data (block 610). The processor 162 may execute the drug utilization review module 555a to, for example, cause the processor 162 to compare the electronic prescription data with drug utilization rules data (block 615). If the processor 162 determines that the prescription complies with the drug utilization rules (block 620), the processor 162 may execute the message generation and transmission module 560a to, for example, cause the processor 162 to generate a compliance notification (block 625). If the processor 162 determines that the prescription does not comply with the drug utilization rules (block 620), the processor 162 may execute the message generation and transmission module 560a to, for example, cause the processor 162 to generate a non-compliance notification (block 630). The processor 162 may end the method 600 (block 635).

Figure 7:
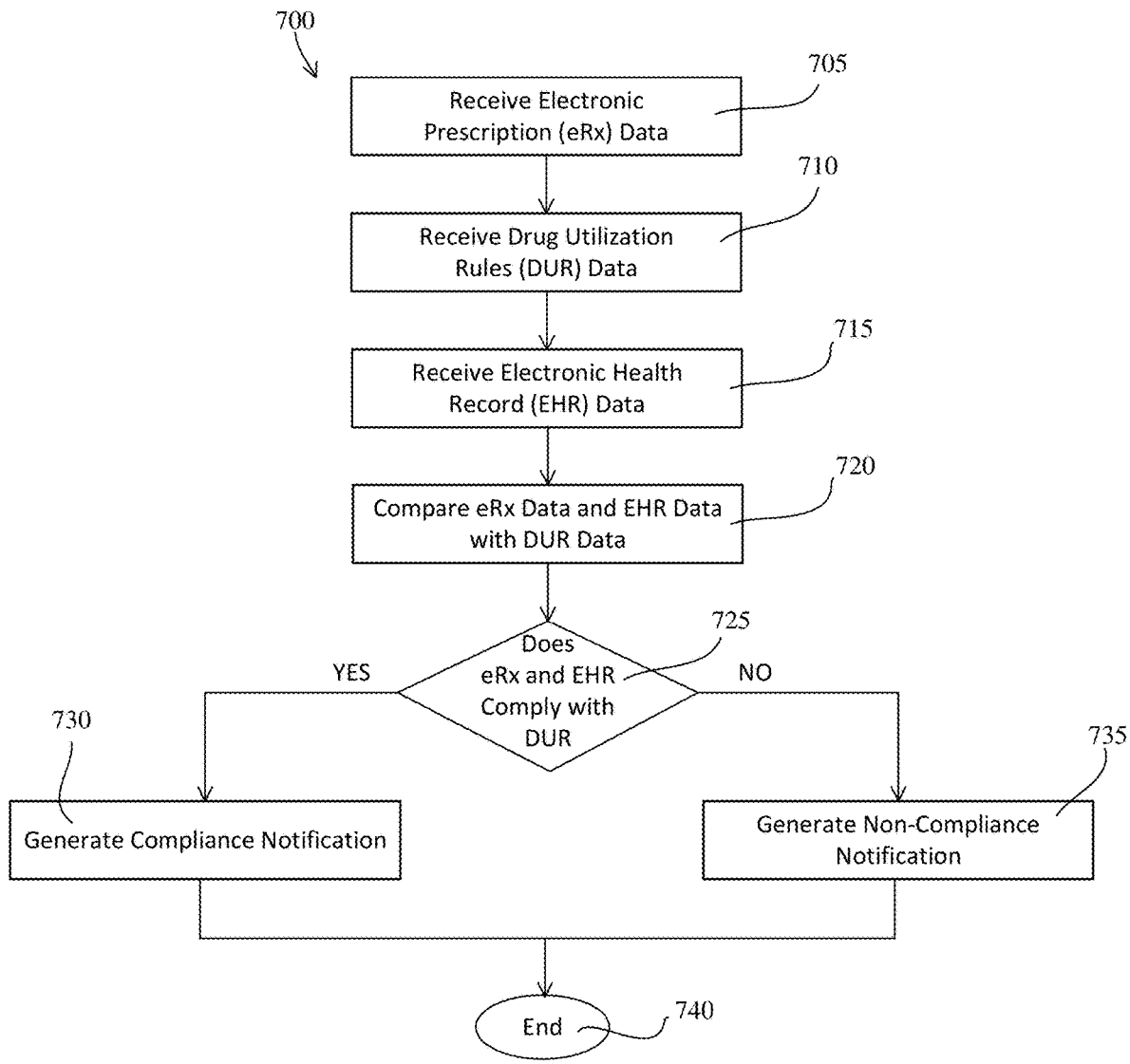
FIG. 7 depicts an example computer implemented method of performing a drug utilization review.

With reference to FIG. 7, a computer implemented method of performing a drug utilization review 700 may be implemented by, for example, the drug utilization engine 505a. In particular, a processor (e.g., processor 162 of FIG. 1) may execute the electronic prescription (cRx) data receiving module 515a to, for example, cause the processor 162 to receive eRx data (block 705). The processor 162 may execute the drug utilization review (DUR) data receiving module 530a to, for example, cause the processor 162 to receive DUR data (block 710). The processor 162 may execute the electronic health record (EHR) data receiving module 525a to, for example, cause the processor 162 to receive EHR data (block 715). The processor 162 may execute the drug utilization review module 555a to, for example, cause the processor 162 to compare the electronic prescription data and the electronic health record data with the drug utilization rules data (block 720). If the processor 162 determines that the electronic prescription data and the electronics health data complies with the drug utilization rules (block 725), the processor 162 may execute the message generation and transmission module 560a to, for example, cause the processor 162 to generate a compliance notification (block 730). If the processor 162 determines that the electronic prescription data and/or the electronic health records data does not comply with the drug utilization rules (block 725), the processor 162 may execute the message generation and transmission module 560a to, for example, cause the processor 162 to generate a non-compliance notification (block 735). The processor 162 may end the method 700 (block 740).

Figure 8:
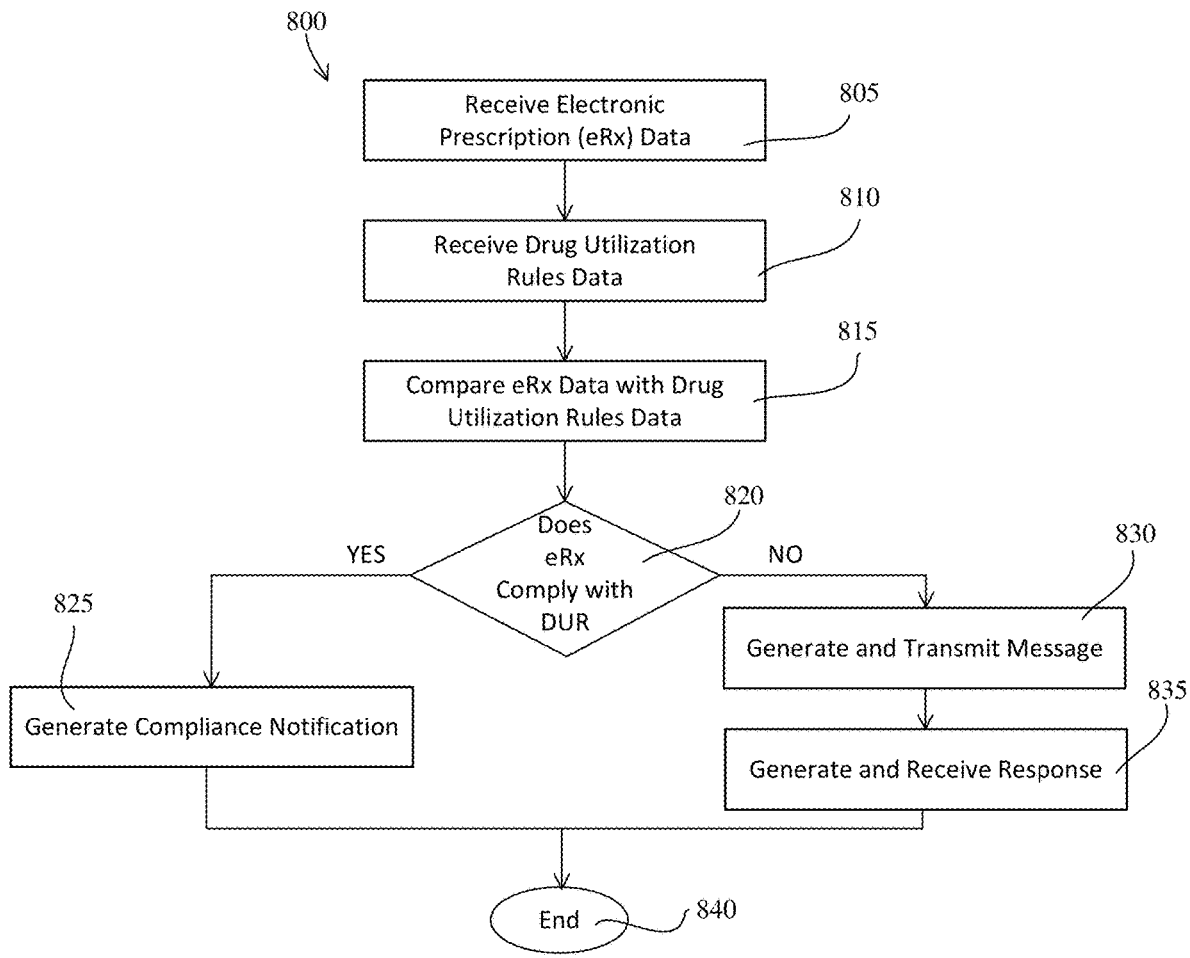
FIG. 8 depicts an example computer implemented method of performing a drug utilization review and correcting a prescription.

Turning to FIG. 8, a computer implemented method of performing a drug utilization review and correcting a prescription 800 may be implemented by, for example, the drug utilization engine 505a. In particular, a processor (e.g., processor 162 of FIG. 1) may execute the electronic prescription (eRx) data receiving module 515a to, for example, cause the processor 162 to receive eRx data (block 805). The processor 162 may execute the drug utilization review rules (DUR) data receiving module 530a to, for example, cause the processor 162 to receive DUR data (block 810). The processor 162 may execute the drug utilization review module 555a to, for example, cause the processor 162 to compare the electronic prescription data with drug utilization rules data (block 815). If the processor 162 determines that the prescription complies with the drug utilization rules (block 820), the processor 162 may execute the message generation and transmission module 560a to, for example, cause the processor 162 to generate a compliance notification (block 825). If the processor 162 determines that the prescription does not comply with the drug utilization rules (block 820), the processor 162 may execute the message generation and transmission module 560a to, for example, cause the processor 162 to generate and transmit a non-compliance notification (block 830) to, for example, a prescriber. The processor 162 may execute the response generation and receiving module 565a to, for example, cause the processor 162 to receive a response (block 835) from, for example, the prescriber. As a particular example, the processor 162 may generate and transmit a message to a prescriber requesting the prescriber to verify a prescription 300. In response to receiving the message, the prescriber may, for example, either verify the prescription 300 or modify the prescription 300. The processor 162 may end the method 800 (block 840).

Figure 9:
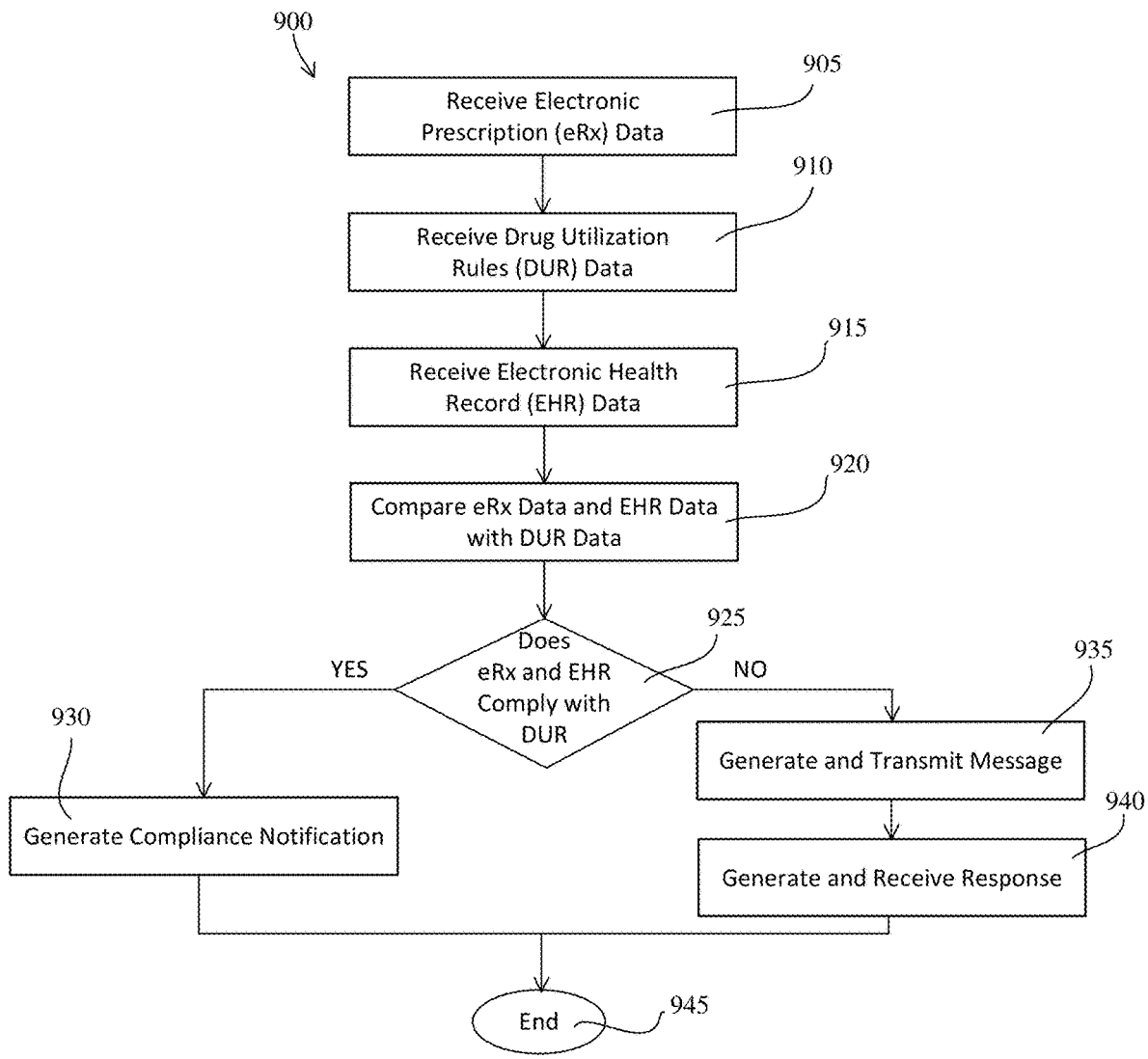
FIG. 9 depicts an example computer implemented method of performing a drug utilization review and correcting a prescription.

With reference to FIG. 9, a computer implemented method of performing a drug utilization review and correcting a prescription 900 may be implemented by, for example, the drug utilization engine 505a. In particular, a processor (e.g., processor 162 of FIG. 1) may execute the electronic prescription (eRx) data receiving module 515a to, for example, cause the processor 162 to receive eRx data (block 905). The processor 162 may execute the drug utilization rules (DUR) data receiving module 530a to, for example, cause the processor 162 to receive DUR data (block 910). The processor 162 may execute the electronic health record (EHR) data receiving module 525a to, for example, cause the processor 162 to receive EHR data (block 915). The processor 162 may execute the drug utilization review module 555a to, for example, cause the processor 162 to compare the electronic prescription data and the electronic health record data with the drug utilization rules data (block 920). If the processor 162 determines that the electronic prescription data and the electronics health data complies with the drug utilization rules (block 925), the processor 162 may execute the message generation and transmission module 560a to, for example, cause the processor 162 to generate a compliance notification (block 930). If the processor 162 determines that the electronic prescription data and/or the electronic health records data does not comply with the drug utilization rules (block 925), the processor 162 may execute the message generation and transmission module 560a to, for example, cause the processor 162 to generate and transmit a non-compliance notification (block 935) to, for example, a prescriber. The processor 162 may execute the response generation and receiving module 565a to, for example, cause the processor 162 to receive a response (block 940) from, for example, the prescriber. As a particular example, the processor 162 may generate and transmit a message to a prescriber requesting the prescriber to verify a prescription 300. In response to receiving the message, the prescriber may, for example, either verify the prescription 300 or modify the prescription 300. The processor 162 may end the method 900 (block 945).

Figure 10:
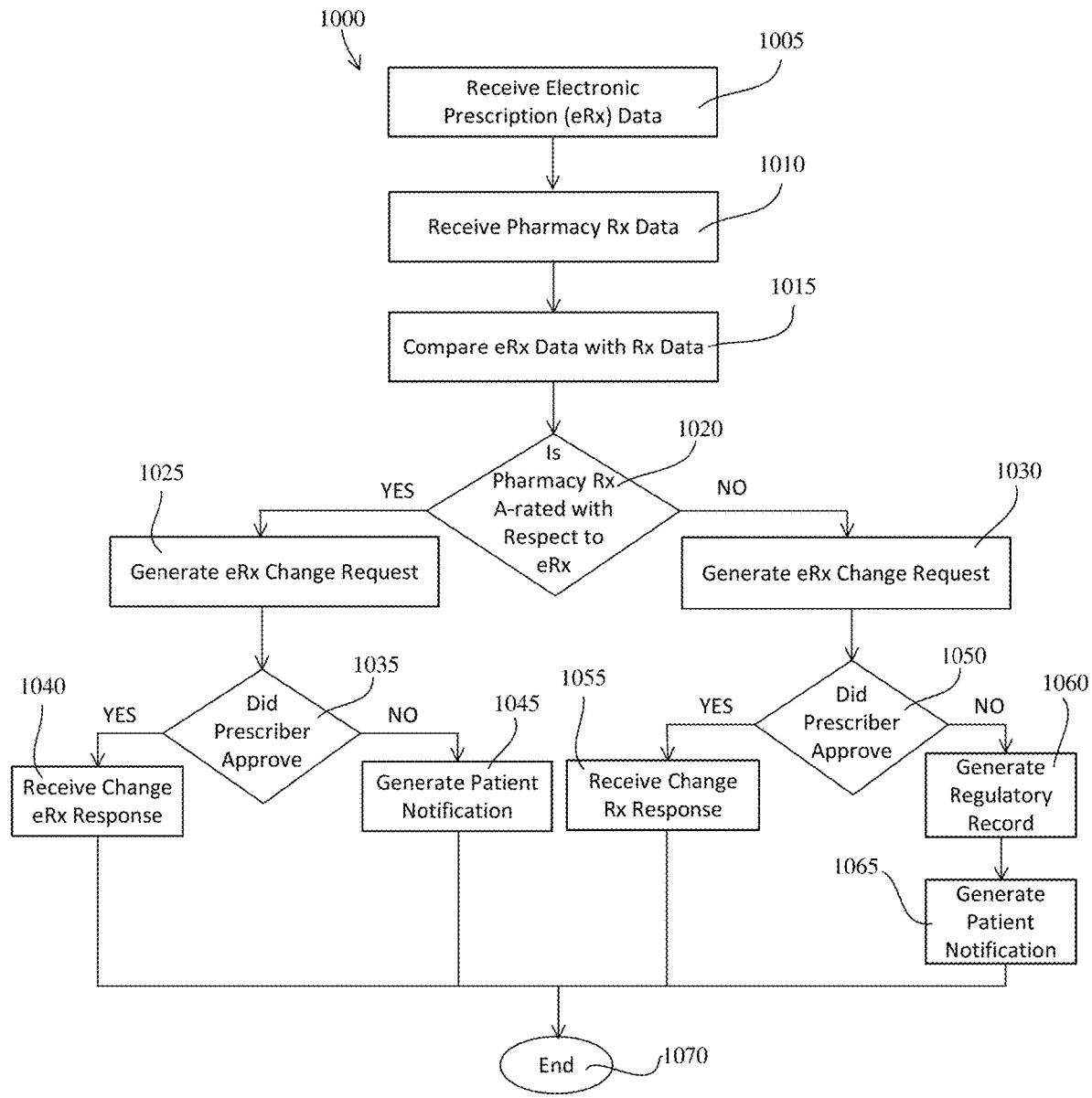
FIG. 10 depicts an example computer implemented method of substituting one medication for another medication.

Turning to FIG. 10, a computer implemented method of substituting one medication for another medication 1000 may be implemented by, for example, the drug utilization engine 505a. In particular, a processor (e.g., processor 162 of FIG. 1) may execute the electronic prescription (eRx) data receiving module 515a to, for example, cause the processor 162 to receive eRx data (block 1005). The processor 162 may execute the pharmacy data receiving module 530a to, for example, cause the processor 162 to receive pharmacy Rx data (block 1010). The processor 162 may execute the drug utilization review module 555a to, for example, cause the processor 162 to compare the electronic prescription data with the pharmacy Rx data (block 1015). If the processor 162 determines that the pharmacy Rx is A-rated with respect to the eRx (block 1020), the processor 162 may execute the message generation and transmission module 560a to, for example, cause the processor 162 to generate an eRx change request (block 1025) to, for example, a prescriber. If the processor 162 determines that the prescriber approved the eRx change request (block 1035), the processor 162 may, for example, execute the response generation and receiving module 565a to receive a changed eRx response (block 1040). If the processor 162 determines that the prescriber did not approve the eRx change request (block 1035), the processor 162 may, for example, execute the response generation and receiving module 565a to notify a patient of the change from the eRx medication to a pharmacy Rx medication (block 1045). The processor 162 may end the method 1000 (block 1070).

If the processor 162 determines that the preferred pharmacy drug is not A-rated with respect to the eRx (block 1020), the processor 162 may execute the message generation and transmission module 560a to, for example, cause the processor 162 to generate and transmit an eRx change request (block 1030) to, for example, a prescriber. If the processor 162 determines that the prescriber approved the eRx change request (block 1050), the processor 162 may, for example, execute the response generation and receiving module 565a to receive a changed eRx response (block 1055). If the processor 162 determines that the prescriber did not approve the eRx change request (block 1050), the processor 162 may, for example, execute the response generation and receiving module 565a to generate a regulatory required record of the change from the eRx medication to a pharmacy Rx medication (block 1060). The processor 162 may, for example, further execute the response generation and receiving module 565a to notify a patient of the change from the eRx medication to the pharmacy Rx medication (block 1065). The processor 162 may end the method 1000 (block 1070).

Figure 11:
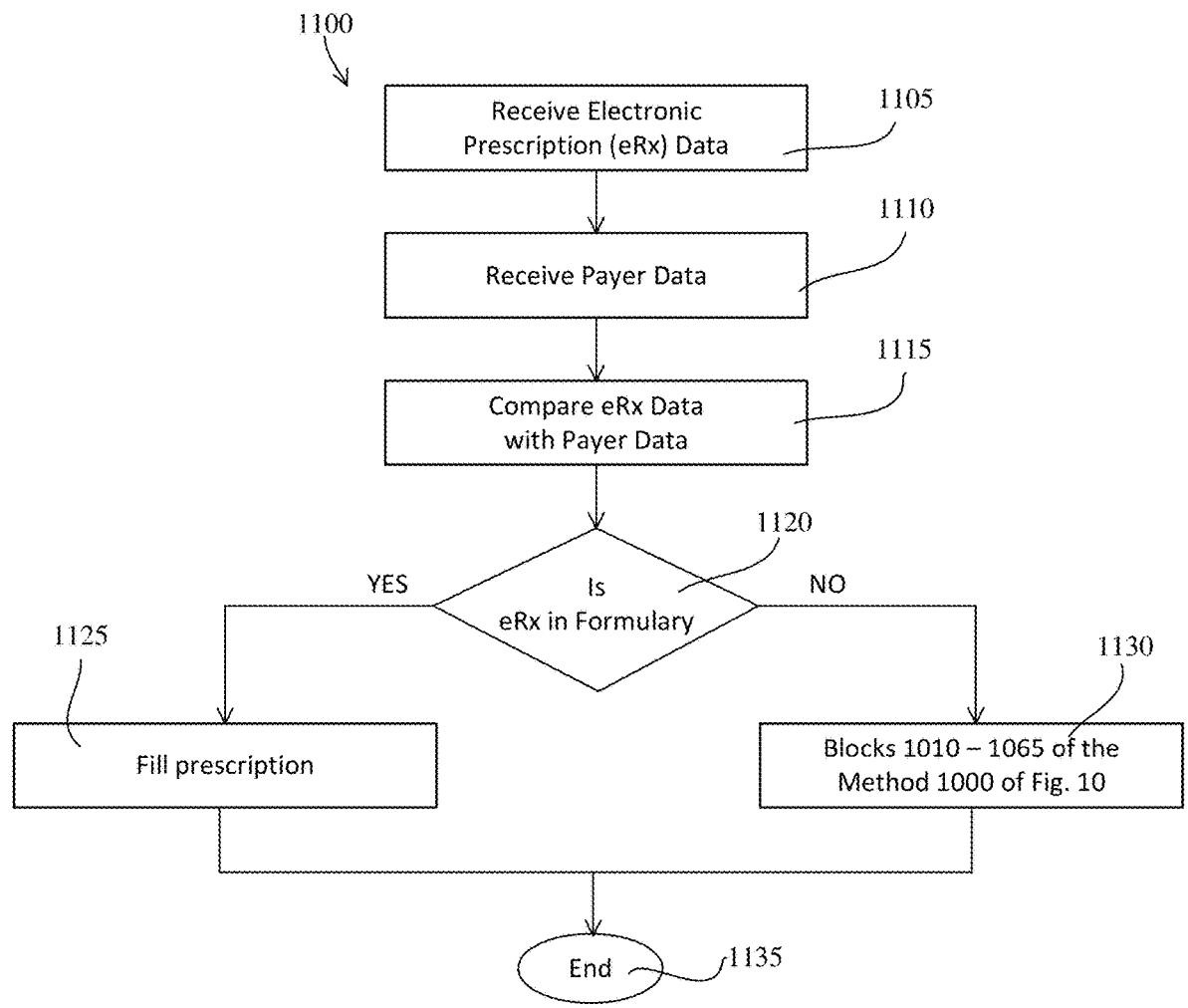
FIG. 11 depicts an example computer implemented method of determining whether a medication is within a formulary.

With reference to FIG. 11, a computer implemented method of determining whether a medication is within a formulary 1100 may be implemented by, for example, the drug utilization engine 505*a*. In particular, a processor (e.g., processor 162 of FIG. 1) may execute the electronic prescription (eRx) data receiving module 515*a* to, for example, cause the processor 162 to receive eRx data (block 1105). The processor 162 may execute the payer data receiving module 535*a* to, for example, cause the processor 162 to receive payer data (block 1110). The processor 162 may execute the drug utilization review module 555*a* to, for example, cause the processor 162 to compare the electronic prescription data with the payer data (block 1115). If the processor 162 determines that the eRx medication is covered by the payer formulary (block 1120), the processor 162 may execute the message generation and transmission module 560*a* to, for example, cause the processor 162 to generate a notification (block 1125) to, for example, a pharmacist to fill the eRx. If the processor 162 determines that the eRx medication is not covered by the payer formulary (block 1020), the processor 162 may, for example, implement blocks 1010-1065 of method 1000 of FIG. 10 (block 1040) to, for example, replace the eRx medication with a pharmacy Rx medication. The processor 162 may end the method 1100 (block 1135).

Electronic prescribing (eRx) and related products have the capability to, for example, redefine a future state of electronic prescribing ecosystem components and pharmacy workflow. Electronic prescription processing systems 100 may enable automated end-to-end prescription processing including, for example, exception cases (e.g., a prescription that is routed through alternate workflow due to presence of barriers that need to be addressed, such as, medication that is out of stock, confirm allergies with a prescriber, DUR screening results need consultation with patient or prescriber, or a case where a prescribed medication is not included within an associated formulary of a payer). Electronic prescription processing may include an interconnected ecosystem 200 capable of handoffs in between a prescriber and a pharmacist. Electronic prescription processing may accelerate patient safety improvements.

Electronic prescribing ecosystem components 200 may include an eRx having a drug name and dosage regimen. A full dosage regimen may include a dose, a frequency, a duration, and a route of administration of the drug to be administered. A pharmacy (e.g., Walgreens) may implement a prescriber directions (Sig) conversion process that may, for example, convert from free text to a proprietary or abbreviated format. An intermediate output may include a codified format that deviates from National Council for Prescription Drug Programs (NCPDP) standards to, for example, enable greater data extraction success rates or foster interoperability. A codified format, however, may not be transmitted on outbound messages without additional information technology (IT) development to align to standard format. A converted prescriber Sig may be used for quality validations and quantity, days of supply (DOS) calculations. A prescriber Sig may not be in a patient-friendly format able to be displayed directly to customers. A converted SIG may be used to enable additional benefits. For example, a prescriber SIG may include "TK 1 T PO QD." A pharmacy conversion of the prescriber Sig may result in "one tablet, oral route, daily" by recognizing a verb as "Take," a dose as "1," a dosage for as "Tablet," a route of administration as "By Mouth," and a frequency as "Every Day." Accordingly, a more granular drug utilization review may result in quality improvements based on, for example, a dosing frequency rather than daily dose (e.g., 2 tablets every morning is not the same as 1 Tablet twice daily in terms of bioavailability or clinical outcomes, but may be commonly presented to DUR engines in a format that is indistinguishable to the engine since the total daily dose (2 tablets) and Days supply are the same). Thereby, a drug utilization review may identify a dose or frequency change, and may provide a clinical alert to pharmacist (e.g., a drug utilization review may trigger an automated eRx change request to a prescriber for confirmation).

Alternatively, or additionally, a drug utilization review may provide consultations for a patient (e.g., a personalized conversation-"Your dose has increased-you may notice greater side effects" or "This medication has increased to twice daily"). A drug utilization review may reduce false positives and/or focus counseling on new and changed therapy prescriptions. A drug utilization review may automatically calculate opioid dosing information. Additionally, or alternatively, a drug utilization review may automatically determine a "New to Therapy" status of a prescription. If new to therapy, the drug utilization review may, for example, automatically reduce opioid days of therapy to meet payer and/or regulatory requirements and/or clinical best practices.

Figure 12:
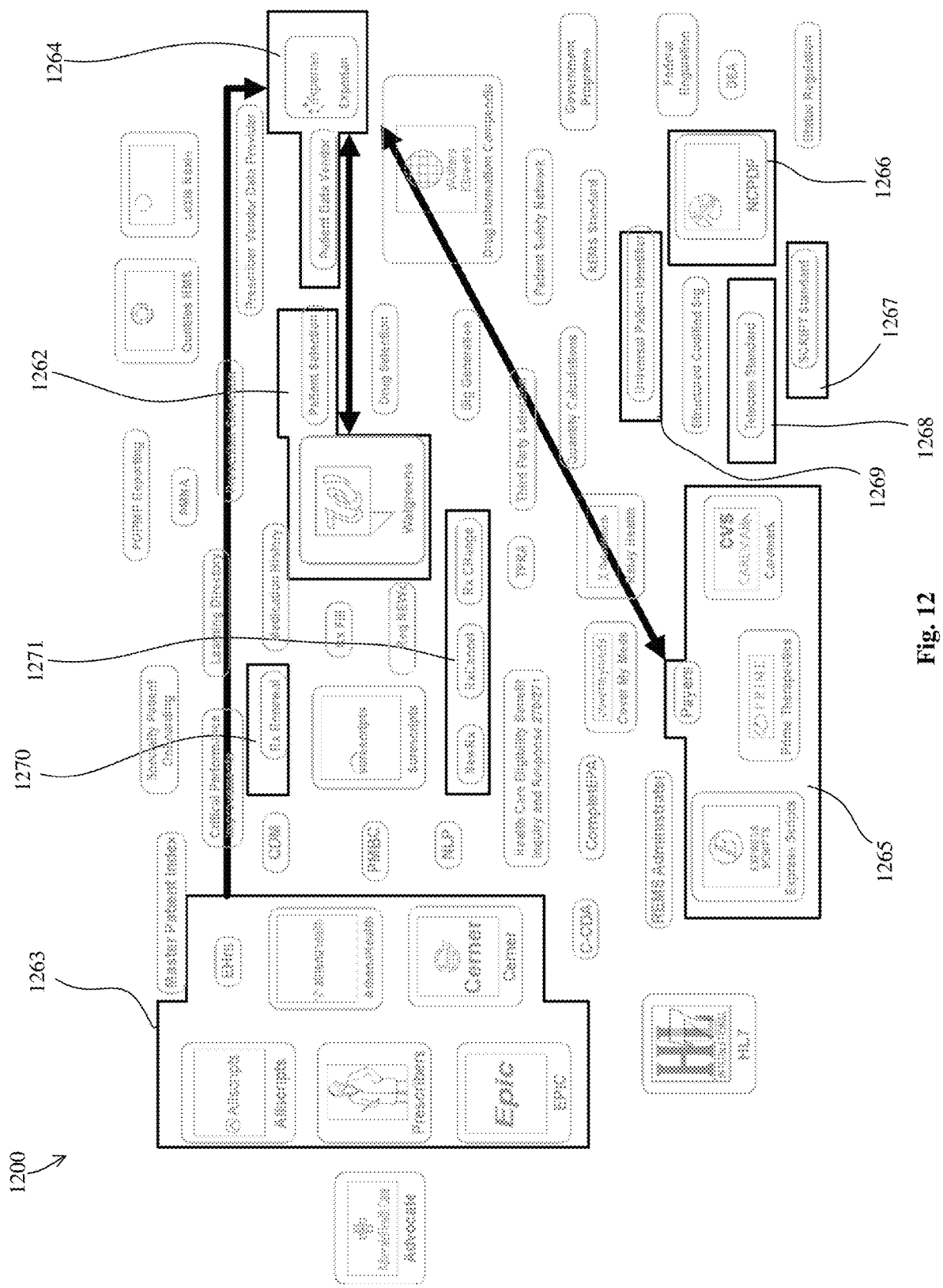
FIG. 12 depicts an example healthcare data source, data transmission, and data reception structure including an automated patient selection.

Turning to FIG. 12, a healthcare data source, data transmission 1268, and data reception structure 1200 may include an automated patient selection 1262 based on, for example, information extracted from an electronic prescription 300, 1270, 1271 (e.g., a patient name, a patient age, an address, etc.). Automated patient selection 1262 may alternatively, or additionally based on National Council for Prescription Drug Programs (NCPDP) data 1266 combined with patient demographic (e.g. Experian) data 1264 to create a Universal Patient Identifier (UPI) 1269. A UPI 1269 may coordinate with electronic health records (EHRs) 1263, pharmacies 1262 and payers 1265 to allow patient identification (e.g., a SCRIPT standard 1267) recognized across the healthcare industry. Patient selection 1262 may be a first step in an automated data entry process. Patient selection 1262 may be handled completely internally within an internal (e.g One-Walgreens) customer database. Despite very high accuracy estimate, an improvement impact score is high for this component due to nearly 10% failure rate in previous attempts to automate patient selection. A UPI 1269 may be intended to improve safety by preventing incorrect patient selection. A UPI 1269 may enable more certainty when matching incoming transactions with internal pharmacy 1262 patient databases. A UPI 1269 may provide a common patient identification format that may be consistent throughout a pharmacy network 110 including electronic prescriptions (eRx) 300 and insurance billing claim transactions. A UPI 1269 may automate patient profile updates with information sourced from, for example, Experian 1264. A UPI 1269 may result in a reduction in duplicate profiles.

Figure 13:
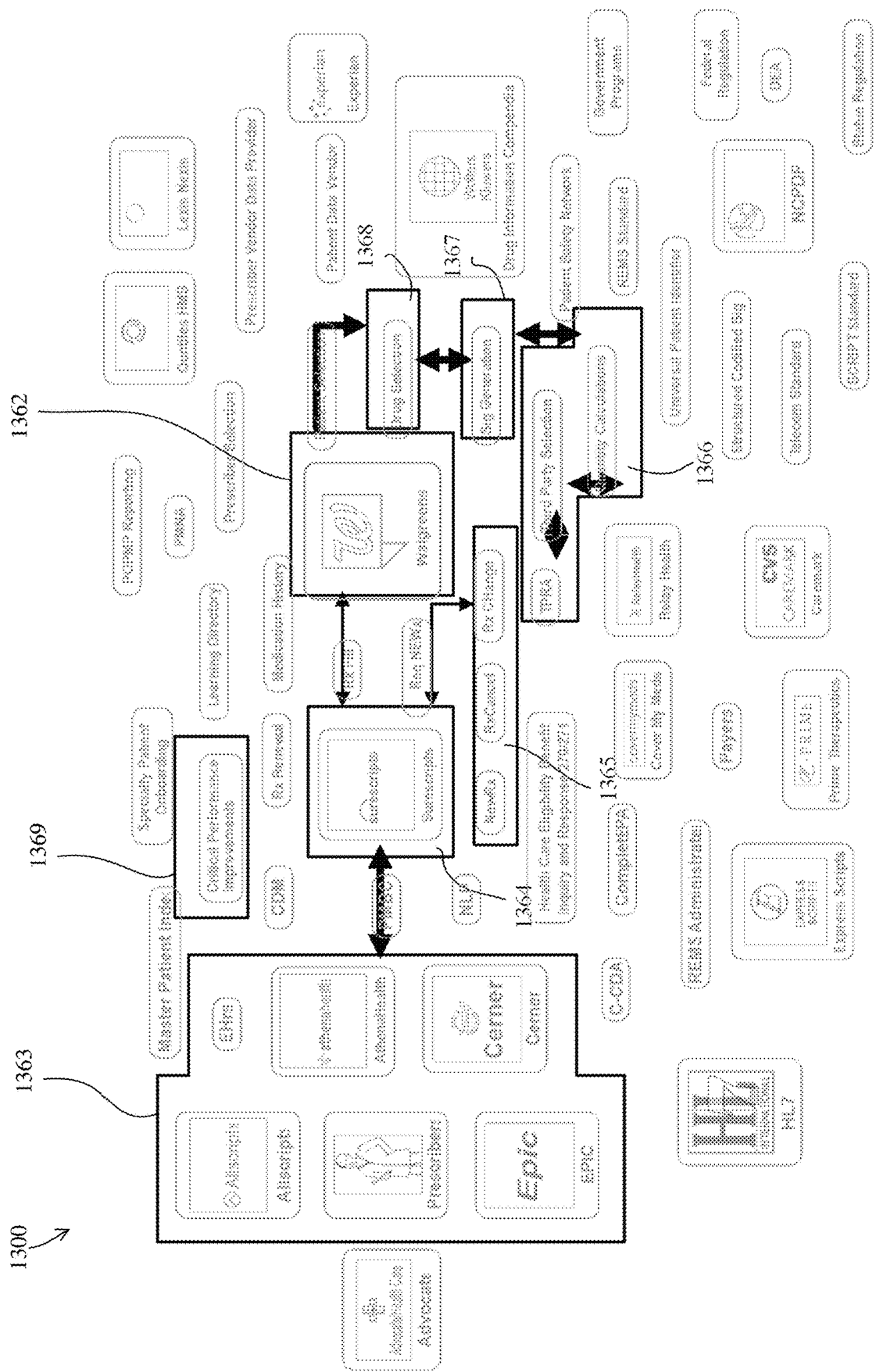
FIG. 13 depicts an example healthcare data source, data transmission, and data reception structure including a drug utilization review for automatic medication changes.

Turning to FIG. 13, a healthcare data source, data transmission, and data reception structure 1300 may include a drug utilization review for automatic medication 1365 changes. Automation may pause while prescription change requests are adjudicated and resume after a response is received. Prescription change requests can be triggered from multiple points in the workflow. Automation workflow may allow for automated change requests to be triggered as, for example, in the methods 1000 of FIG. 10 and 1100 of FIG. 11. Once a response is received, automation can continue. A prescription change request may be, for example, transmitted through Surescripts 1364 then routed to a pharmacy 1362. An automated prescription change may be based on electronics health records data sources 1363, critical performance improvements 1369, a third party risk assessment 1366, prescriber instructions 1367, and/or a drug selection 1368. A response may be, for example, returned electronically. An electronic response may replace a manual phone call and/or a facsimile. Documentation of a prescription change may also be electronic. The electronic documentation may be automatic, thereby, reducing compliance and documentation concerns.

Figure 14:
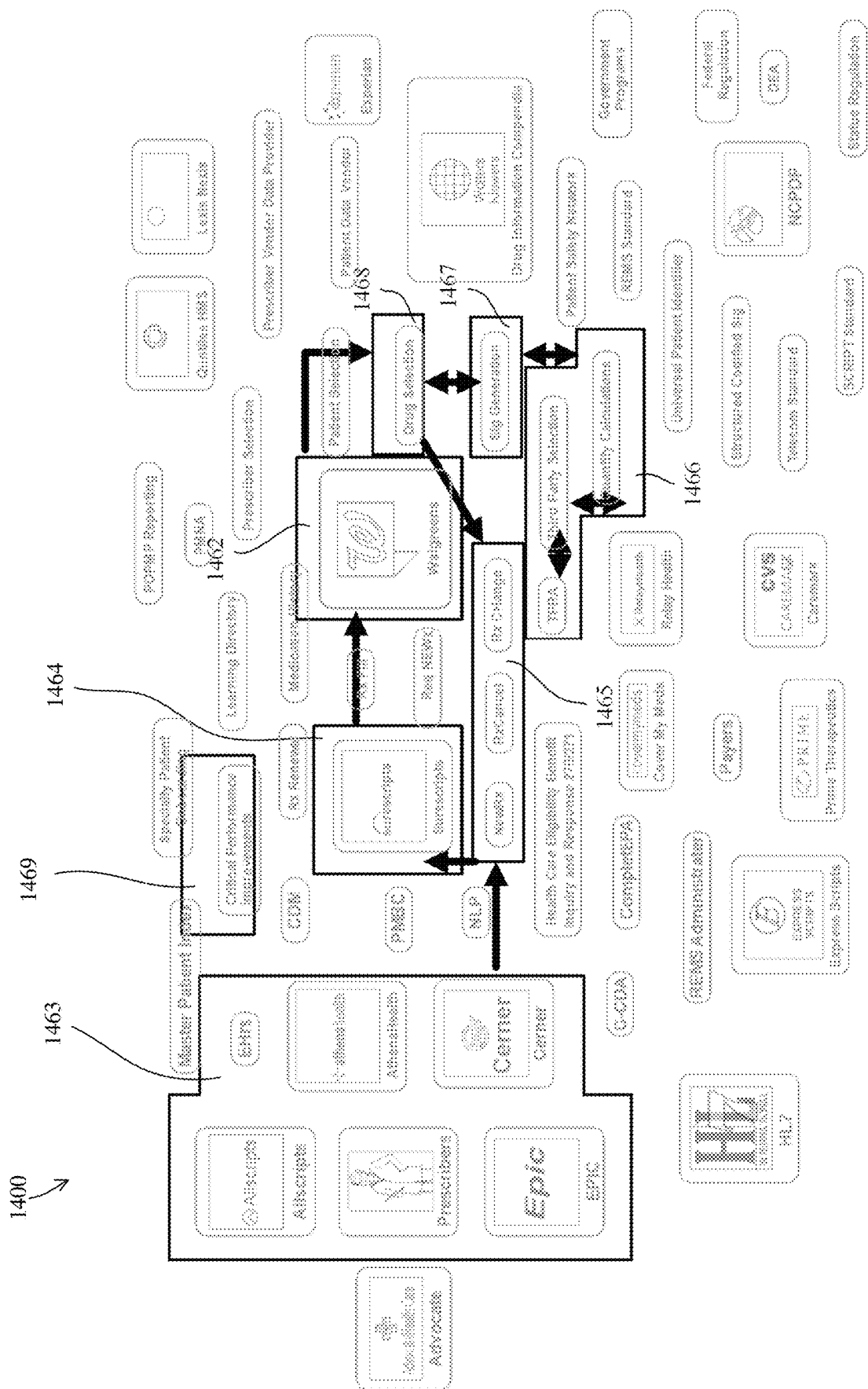
FIG. 14 depicts an example healthcare data source, data transmission, and data reception structure including a drug utilization review for automatic medication changes.

With reference to FIG. 14, a healthcare data source, data transmission, and data reception structure 1400 may include a drug utilization review for automatic medication 1465 changes. Automation workflow may allow for automated change requests to be triggered as, for example, in the methods 1000 of FIG. 10 and 1100 of FIG. 11. A prescription change request may be, for example, transmitted through Surescripts 1464 then routed to an ordering prescriber or their agents (e.g., a pharmacy 1462). An automated prescription change may be based on electronics health records data sources 1463, critical performance improvements 1469, a third party risk assessment 1466, prescriber instructions 1467, and/or a drug selection 1468. A drug utilization review may include an approval to substitute on B-rated drugs in Orange Book states. A drug utilization review may enable brand/generic drug substitution. Similarly, a drug utilization review may enable biosimilar dispensing approval. As a specific example, if a B-rated medication is prescribed, a processor 162 may implement drug utilization rules (e.g., business rules) and the processor 162 may determine when to request approval to substitute preferred products in Orange Book states. A national drug code (NDC) nine-digit product code (Core9 NDC) may be maintained. A conservative process designed may be implemented to ensure no inappropriate dispensing. However, a conservative process may lead to non-optimal product selection driving operational change manufacturer events which may lead to customer disruption or confusion. A prescription change request may, for example, obtain explicit approval to dispense a drug of a preferred manufacturer in states where approval is required. As another example, if a prescription indicates dispense as written (DAW), a change request may be triggered to allow for generic substitution. Changing to a generic substitution may increase generic utilization, and lower costs for the patient and overall healthcare system. As a further example, instead of a pharmacist making a decision to substitute a biosimilar drug (which triggers reporting requirements), a change request may be sent to an associated prescriber to explicitly authorize dispensing of the biosimilar product. The explicit authorization from the prescriber exceeds reporting requirements. An associated electronic response to the request may automatically document therapeutic interchange approval. A prescription change request may be initiated due to, for example, pharmacy inventory conditions.

Figure 15:
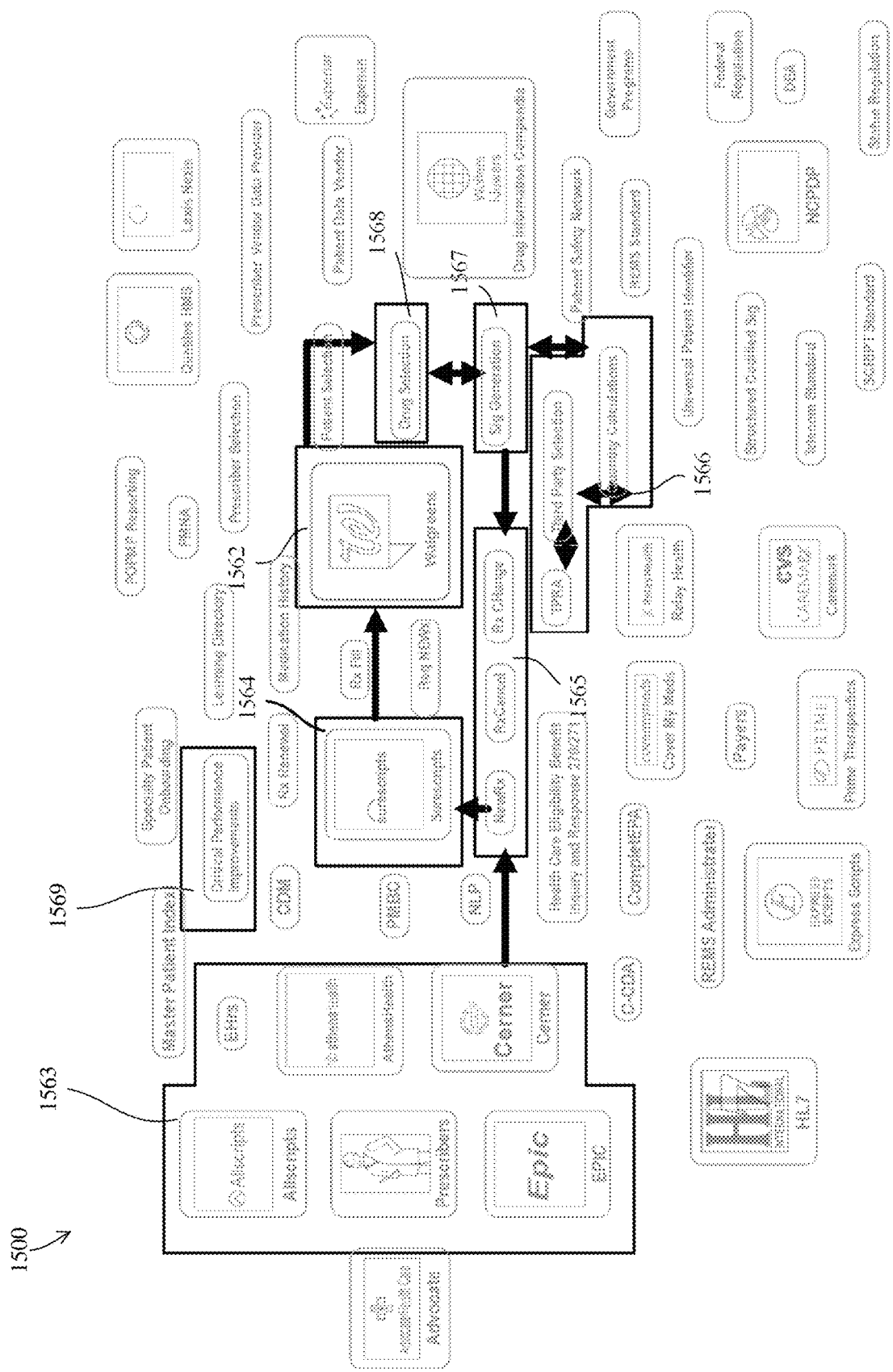
FIG. 15 depicts an example healthcare data source, data transmission, and data reception structure including a drug utilization review for automatic medication changes.

Turning to FIG. 15, a healthcare data source, data transmission, and data reception structure 1500 may include a drug utilization review for automatic medication 1565 changes. Automation workflow may allow for automated change requests to be triggered as, for example, in the methods 1000 of FIG. 10 and 1100 of FIG. 11. A prescription change request may be, for example, transmitted through Surescripts 1564 then routed to a pharmacy 1562. An automated prescription change may be based on electronic health records data sources 1563, critical performance improvements 1569, a third party risk assessment 1566, prescriber instructions 1567, and/or a drug selection 1568. An associated drug utilization review may enable medication changes and/or drug selection along with prescriber instruction generation Rx change use cases and directions clarification, and dose confirmation when different than previous therapy. Likewise, a drug utilization review may generate pharmacy medication related directions that may be clarified automatically. For example, a drug utilization review may generate outbound messages to a prescriber describing an issue that needs to be clarified (e.g., missing and/or required Rx elements, medication dose/strength mismatch, conflicting information, etc.). Non-specific directions, such as USE AS DIRECTED, can trigger a request for more precise directions. Thereby, a pharmacist may reduce comprehensive loss by preventing chargebacks; this may be particularly impactful for controlled substances and to Med B and specialty patients. Additionally, or alternatively, changes in dose from previous therapy can be detected and confirmed or corrected to prevent quality events.

Figure 16:
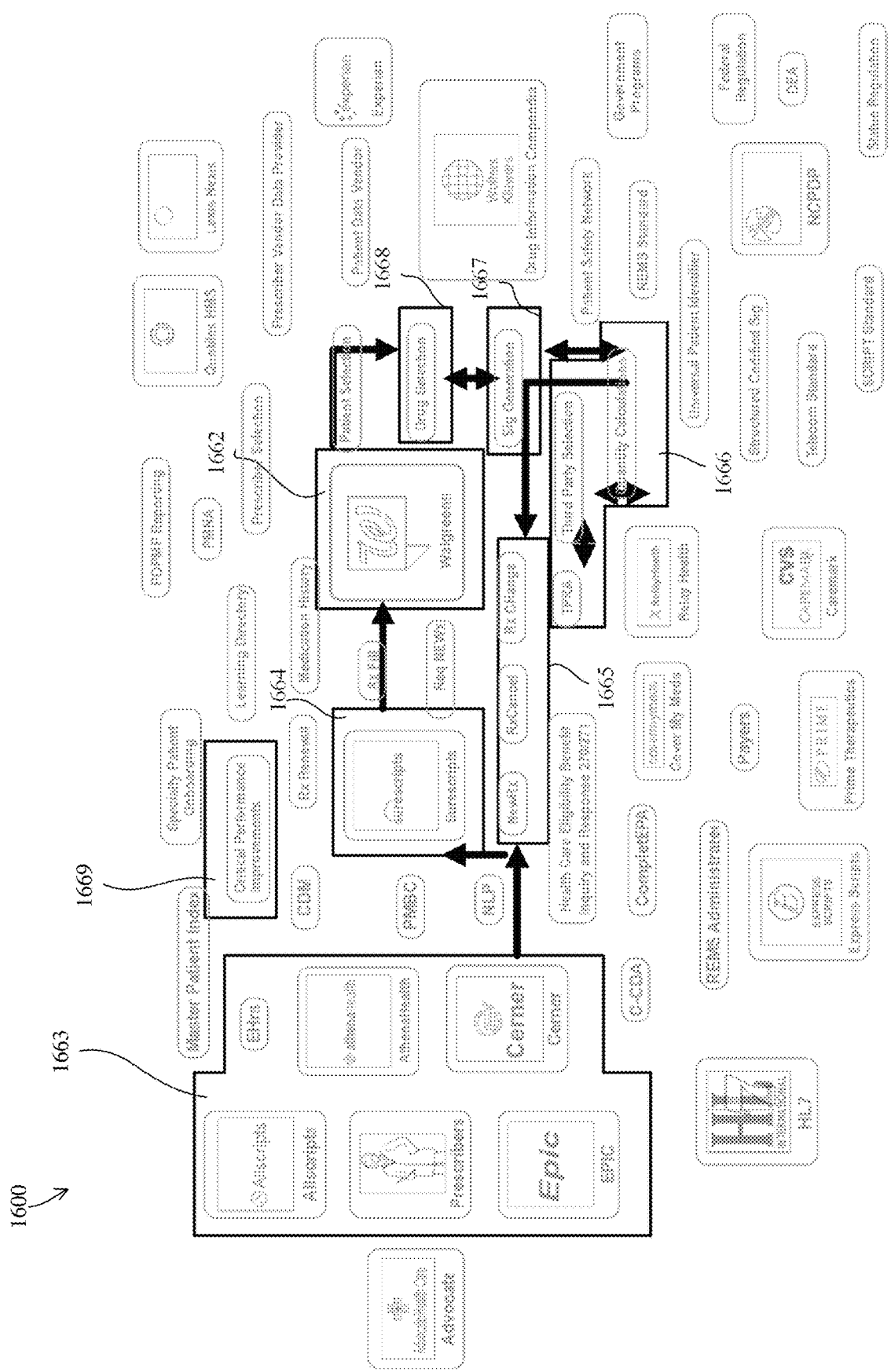
FIG. 16 depicts an example healthcare data source, data transmission, and data reception structure including a drug utilization review for automatic medication changes.

With reference to FIG. 16, a healthcare data source, data transmission, and data reception structure 1600 may include a drug utilization review for automatic medication 1665 changes. Automation workflow may allow for automated change requests to be triggered as, for example, in the methods 1000 of FIG. 10 and 1100 of FIG. 11. A prescription change request may be, for example, transmitted through Surescripts 1664 then routed to a pharmacy 1662. An automated prescription change may be based on electronics health records data sources 1463, critical performance improvements 1669, a third party risk assessment 1666, prescriber instructions 1667, and/or a drug selection 1668. A drug utilization review may enable medication changes with quantity calculations. Quantity calculations for Rx change use cases may include, for example, a quantity conversion (e.g., a 90 day conversion) approval and/or a confirm quantity calculation if an eRx medication quantity is outside of pre-determined parameters. During quantity calculations, automatic requests (e.g., 90 day requests) can be generated to align to patient preferences, reducing costs, and to improve adherence and patient outcomes; this may replace telephonic, facsimile or other interim workarounds using modified refill requests which have been identified by the industry as a pain point. Calculated quantity that does not meet clinical quality algorithms may automatically trigger a Rx change request to clarify. Similarly, a days of supply (DOS) greater than 100 days may automatically trigger a Rx change request to clarify since this quantity is not typically dispensed. A suboptimal treatment length may automatically trigger a Rx change request to clarify. An incorrect or unspecified quantify qualifiers may automatically trigger a Rx change request to clarify (e.g., transmitted quantity of "6" for enoxaparin 60 mg (0.6 mL/syringe). 6 syringes or 6 mL (10 syringes) could both be reasonably inferred from quantity of "6" if it does not contain a qualifier. A change in quantity due to stock conditions or patient request may automatically trigger a Rx change request to modify.

Figure 17:
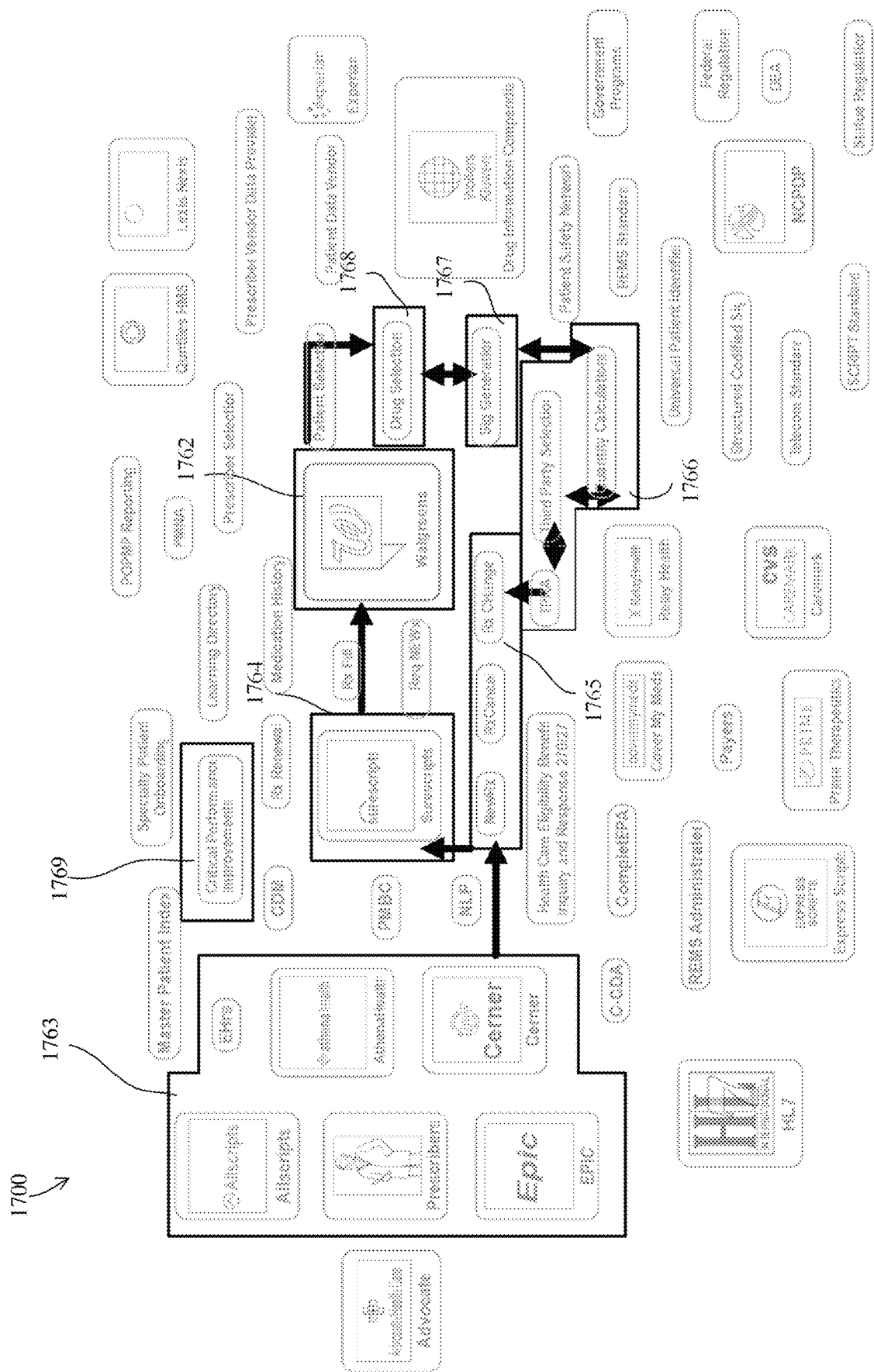
FIG. 17 depicts an example healthcare data source, data transmission, and data reception structure including a drug utilization review for automatic medication changes.

Turning to FIG. 17, a healthcare data source, data transmission, and data reception structure 1700 may include a drug utilization review for automatic medication 1765 changes. Automation workflow may allow for automated change requests to be triggered as, for example, in the methods 1000 of FIG. 10 and 1100 of FIG. 11. A prescription change request may be, for example, transmitted through Surescripts 1764 then routed to an ordering prescriber or their agents (e.g., a pharmacy 1762). An automated prescription change may be based on electronic health records data sources 1763, critical performance improvements 1769, a third party risk assessment 1766, prescriber instructions 1767, and/or a drug selection 1768. A drug utilization review may include medication changes with third party and a third party risk assessment 1766. Third party Rx change use cases may include therapeutic interchange and/or prior authorization notification. Integrating third party selection with prescription claims processing automation and Rx Change has ability to dramatically simplify processes for team members especially for therapeutic interchange. This has been designed and attempted numerous ways previously-but the pieces are finally ready for a comprehensive, automated solution. To meet the consistent requests from payers, for example, discussions with a value creation team and prime therapeutics may be centered around formulary compliance. After a rejected claim indicating a prior authorization. Next step may be typically to request a prior authorization from the prescriber. Pharmacy dispensing systems may integrate with products like Cover My Meds 240 that may streamline prior authorization approvals. Rx change has the capability to notify prescribers of the need for a prior authorization, and this may be an associated workflow. Instead of prior authorization (PA), a pharmacy 1762 (e.g., Walgreens) system may help partner payers achieve greater formulary compliance. For example, formulary alternatives may be returned in a billing response and/or inserted into a Rx change request sent to the prescriber. If the therapeutic interchange is approved, the entire network benefits. Patients may receive a medication that is a lower copay and overall healthcare costs are reduced.

For example, a pharmacy 1762 (e.g., Walgreens) may end up dispensing a generic medication instead of a branded one. A pharmacy 1762 (e.g., Walgreens) may also benefit by meeting contractual obligations with payers. Payers may benefit through greater formulary compliance and lower drug costs.

Figure 18:
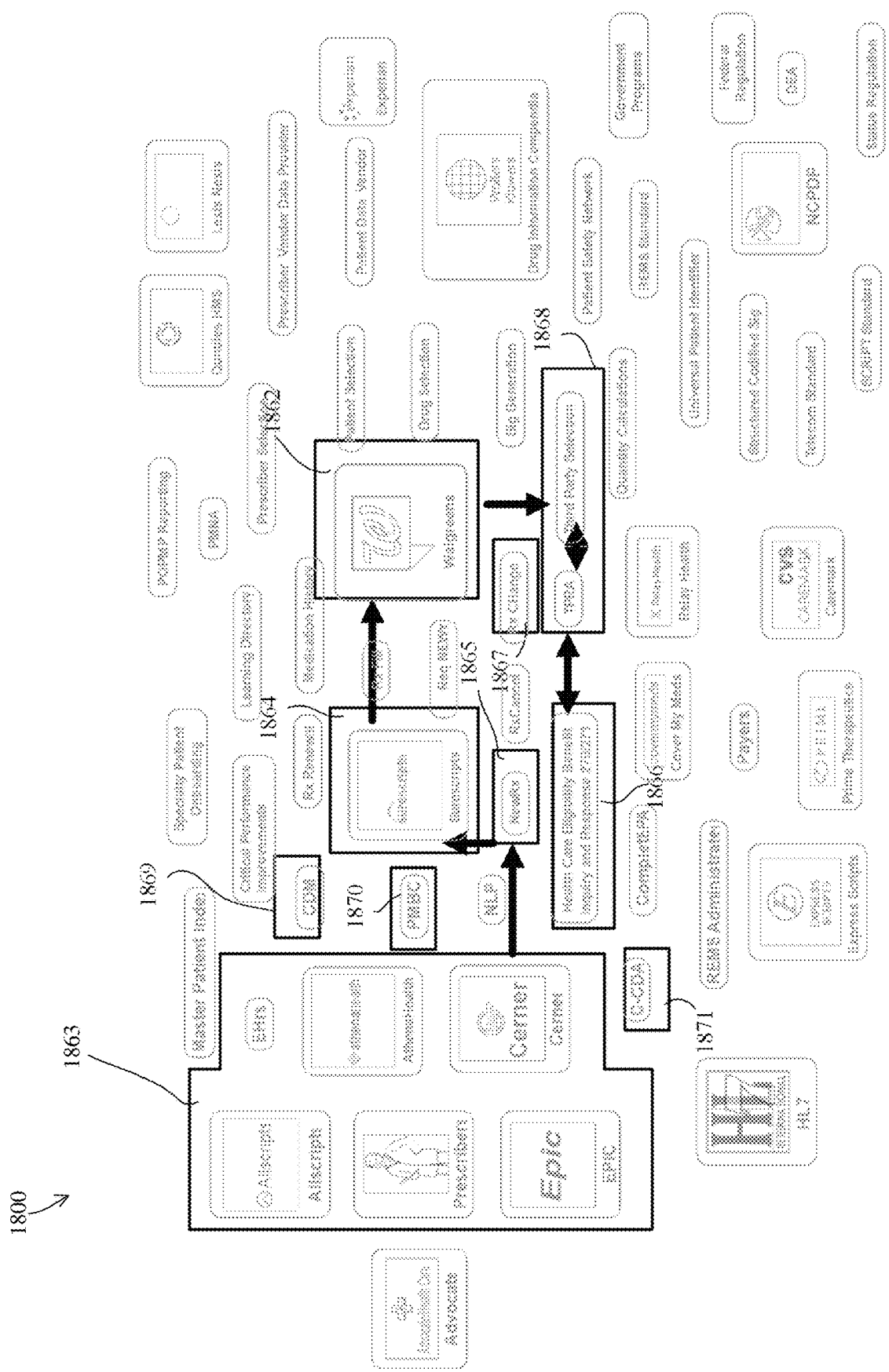
FIG. 18 depicts an example healthcare data source, data transmission, and data reception structure including a third party adjudication to determine medication eligibility.

With reference to FIG. 18, a healthcare data source, data transmission, and data reception structure 1800 may include a third party adjudication to, for example, determine medication eligibility. A new prescription 1865 or a prescription change request 1867 may be, for example, transmitted through Surescripts 1864 then routed to a pharmacy 1762. An associated drug utilization review may include a pharmacy 1862 (e.g., Walgreens), electronics health records data sources 1863, a third party risk assessment 1868, a health care eligibility benefit inquiry and response 270/271 1866, a customer data management (CDM) data source 1821, a consolidated clinical document architecture (C-CDA) data source 1869, and/or a patient medication benefit check (PMBC) data source 1870. Eligibility lookup use cases may include new patient registration, expired plan rejection, and/or other coverage exists rejection. Continuing with Insurance examples, a third party claims process engine may manage a plan selection for automated data entry process in addition to handling rejections. For new patients, or those without any registered plans, an eligibility lookup may be triggered automatically. Alternatively, or additionally, a transaction (e.g. Find Insurance Coverage (FINDINS)) may get routed through Relay Health 247. Although a direct connection, may be lower fees. A gap with non-commercial payers may return results that may enable automatic registration of plans to a patient profile. Certain reject types may trigger automatic eligibility request (e.g., coverage expired, other coverage exists, after all existing plans have been tried, and no paid claim-run eligibility, etc.).

Figure 19:
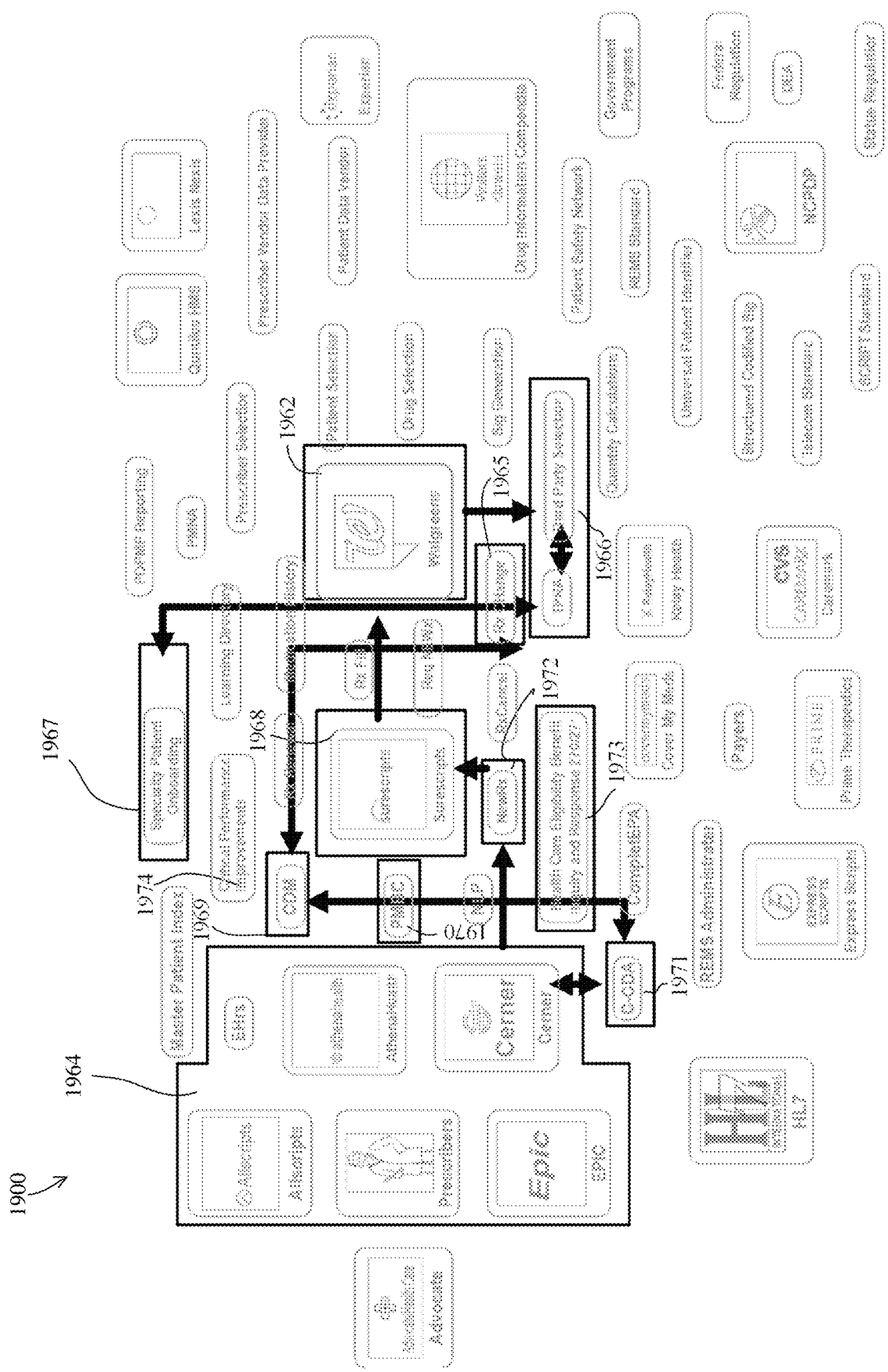
FIG. 19 depicts an example healthcare data source, data transmission, and data reception structure including a third party adjudication with structure-process-outcome (SPO) and/or a clinical information request.

Turning to FIG. 19, a healthcare data source, data transmission, and data reception structure 1900 may include a third party adjudication with specialty patient onboarding (SPO) and/or a clinical information request. An associated drug utilization review may include a pharmacy 1962 (e.g., Walgreens), electronics health records data sources 1964, a third party risk assessment 1966, a health care eligibility benefit inquiry and response 270/271 1973, a customer data management (CDM) data source 1974, a consolidated clinical document architecture (C-CDA) data source 1971, a method to identify electronic prescriber health records (national health record locating and reporting system (NLRS) 1969 (e.g., from SureScripts)), a specialty patient onboarding 1967 and/or a patient (real-time) medication benefit check (PMBC) data source 1970. For example, an automated request and receipt of missing information may be needed for billing and may reduce workload on team members and healthcare accounts receivable team. This may be beneficial for Medicare B and specialty products. Additionally, enhanced integration can enable automated collection of missing billing elements-reducing workload of stores and Healthcare Accounts Receivable (HAR). If billing is unable to be completed due to missing clinical information, automated requests may be routed through different products (e.g., specialty patient onboarding (SPO), a customer data management (CDM), a National health record location system (NRLS), etc.) transaction to look up endpoint and, for example, send consolidated clinical document architecture (C-CDA) request directly. Information potentially needed for billing (e.g., a date of admission/discharge, a date of transplant surgery, diagnosis codes, a Certificate of Medical Necessity for Diabetic Testing Supplies, a Medicare Detailed Work Order (DWO), etc.) may be provided. Automated request and response for billing information may, for example, lower comprehensive loss due to chargebacks from claims for not having sufficient information required for documentation.

Figure 20:
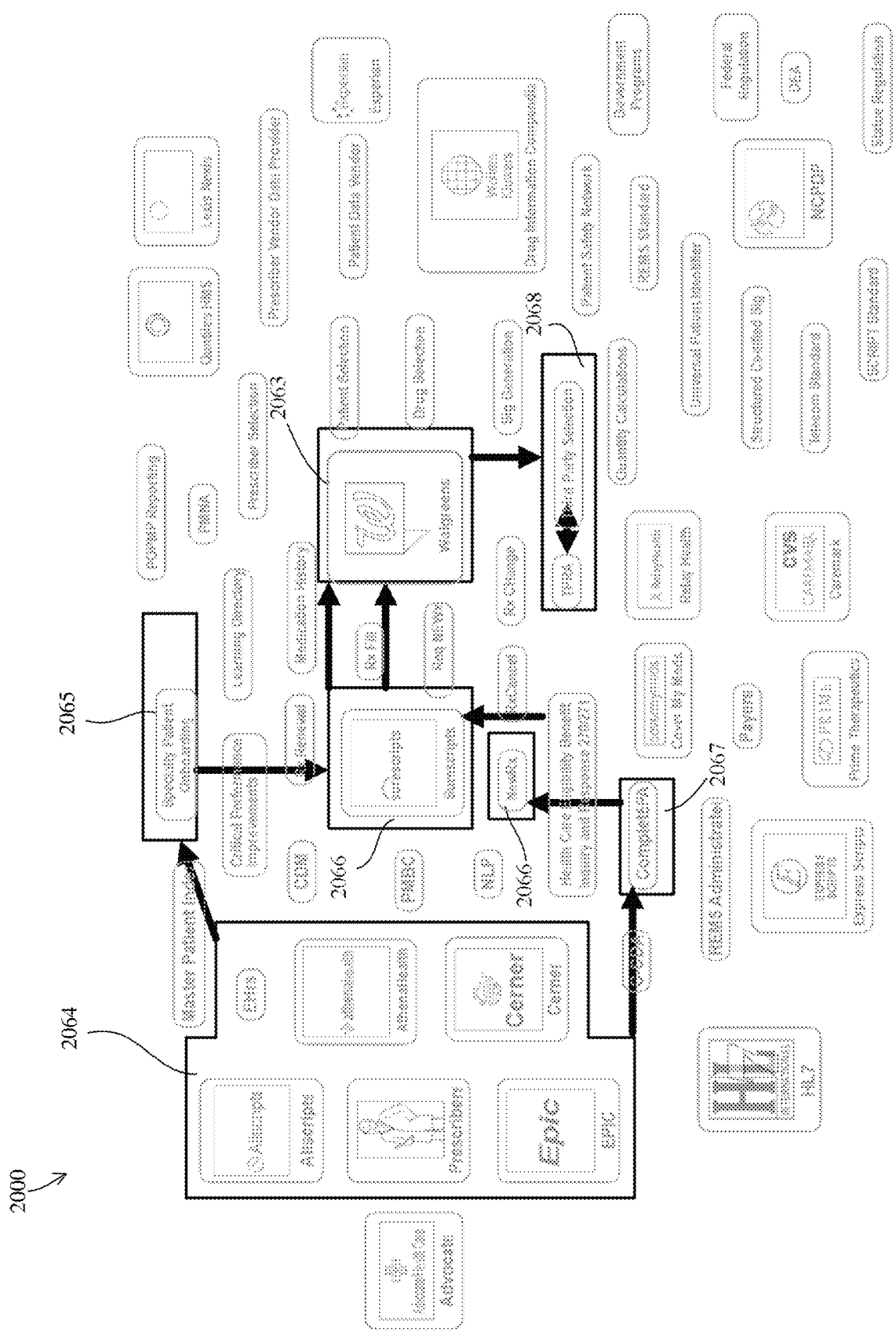
FIG. 20 depicts an example healthcare data source, data transmission, and data reception structure including specialty prescriptions and/or specialty patient onboarding (SPO)

With reference to FIG. 20, a healthcare data source, data transmission, and data reception structure 2000 may include specialty prescriptions and/or specialty patient onboarding (SPO). An associated drug utilization review may include a pharmacy 2063 (e.g., Walgreens), electronics health records data sources 2064, a third party risk assessment 2068, a CompletEPA data source 2067, a SureScripts data source 2066, a newRx 2069 and/or a specialty patient onboarding 2065. A specialty patient onboarding product may increase eRx efficiency for pharmacies and prescribers by transmitting needed information electronically instead of via fax. For specialty medications, a Surescripts SPO product may send additional clinical information about a prescription that can be electronically connected to the Rx and provide supplemental info needed for billing and dispensing. Prospective prior authorization approval, similar to CompletEPA 2067, may be included. For limited distribution drugs (LDD) drugs, only particular pharmacies may be able to dispense. Electronic Intake forms may replace faxed versions. Electronic lab results, needed for billing or FDA-mandated Risk Evaluation and Mitigation Strategy (REMS) approvals, may replace faxes. Biosimilar dispensing may be accommodated; instead of a pharmacist deciding to substitute which then triggers reporting requirements, a change request could be sent to prescriber to explicitly authorize dispensing of the biosimilar product. The changed Rx exceeds reporting requirements, and may automatically document therapeutic interchange approval.

A drug change request may be due to inventory conditions. A drug utilization engine 500*a* may implement major drug utilization reviews that require comments to override (e.g., a major drug/allergy, drug/genotype, drug/drug interaction, pregnancy contraindication, etc.). Additionally, a drug utilization engine 500a may implement moderate drug utilization reviews that do not require comments to override (e.g., moderate drug/drug interaction, etc.). A drug utilization engine 500a may implement minor drug reviews with no severity code and that do not require comments to override (e.g., Health conditions excluding pregnancy (even contraindications), a duplicate therapy, an inappropriate dose, an inappropriate length of therapy, etc.). Enhanced drug utilization reviews may be implemented when, for example, a clinical rationale does not exist (e.g., a duplicate therapy allowance-will be Major DUR, maximum dose exceeded-will be Major DUR, Health condition contraindication-will be Major DUR for pediatrics, etc.). Drug utilization rules may identify, for example, an inappropriate route of administration, an inappropriate unit of measure, an inappropriate prescriber directions for use (with correct DOS), a duplicate therapy, a maximum medication dosage exceeded, health condition contraindication, an inappropriate drug cocktail, additive toxicity, undesirable outcomes, an undesirable impact on adherence, any sub-combination thereof, or a combination thereof. A drug utilization engine may implement the drug utilization rules to, for example, automatically perform a drug utilization review for a given patient. Initial drug utilization rules may be based on quality alerts and audits (e.g., a specificity of >90% may be required to initiate new drug utilization review; rules with >10% false positives in sample data may be excluded; monthly/quarterly governance committee led by patient safety, clinical, labor, legal, regulatory, legal, tort, operations, etc.)

Figure 21A:
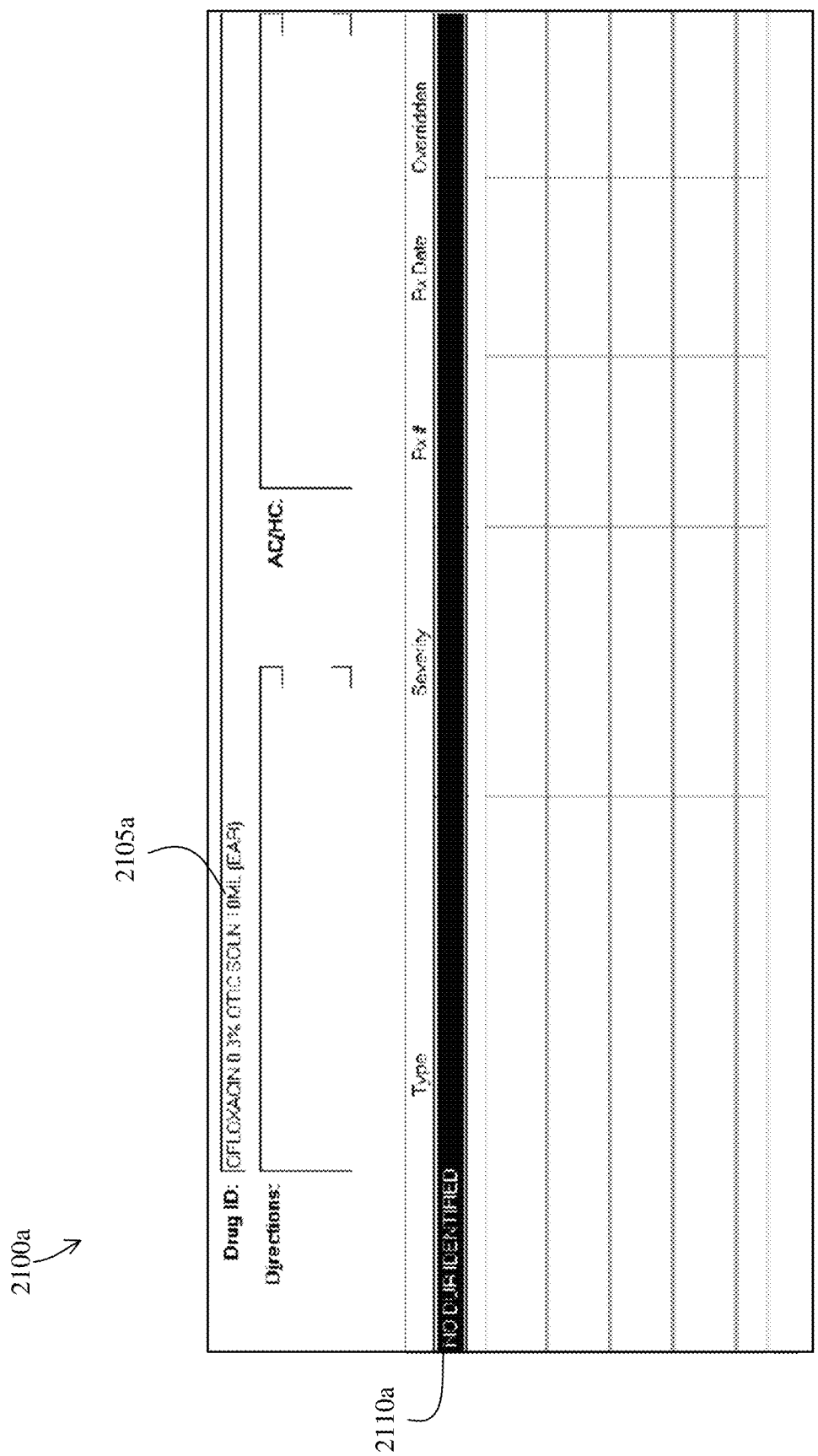
FIGS. 21A and B depict an example drug utilization review including a route of administration drug utilization rule.

Turning to FIGS. 21A and B, a drug utilization review 2100a,b may include a route of administration drug utilization rule. This drug utilization review may replace quality alerts at a point in an eRx data review. For example, a prescription 300 may include an entered drug 310 Ofloxacin Otic Solution. Ofloxacin Otic Solution may be used, for example, to treat outer ear infections (e.g., swimmer's ear, ear canal infections, etc.) and/or middle ear infections. Ofloxacin Otic Solution may, for example, stop the growth of bacteria. Ofloxacin Otic Solution belongs to a class of drugs called quinolone antibiotics. The prescription 300 may include entered directions 312 including "place one drop in each eye BID." When included in a prescription, b.i.d. means twice (two times) a day. BID is an abbreviation for "bis in die" which in Latin means twice a day. The abbreviation b.i.d. is sometimes written without a period either in lower-case letters as "bid" or in capital letters as "BID". In any event, because Ofloxacin Otic Solution is intended for use in treating ear related ailments, an associated drug utilization rule may identify an erroneous route of administration (i.e., "place one drop in each eye"). FIG. 21A illustrates a drug utilization review 2100a for a medication 2105a with no associated drug utilization rule 2110a. FIG. 21B illustrates a drug utilization review 2100b for a medication 2105b with a drug utilization rule 2110b and a drug utilization review summary 2115b.

Figure 22A:
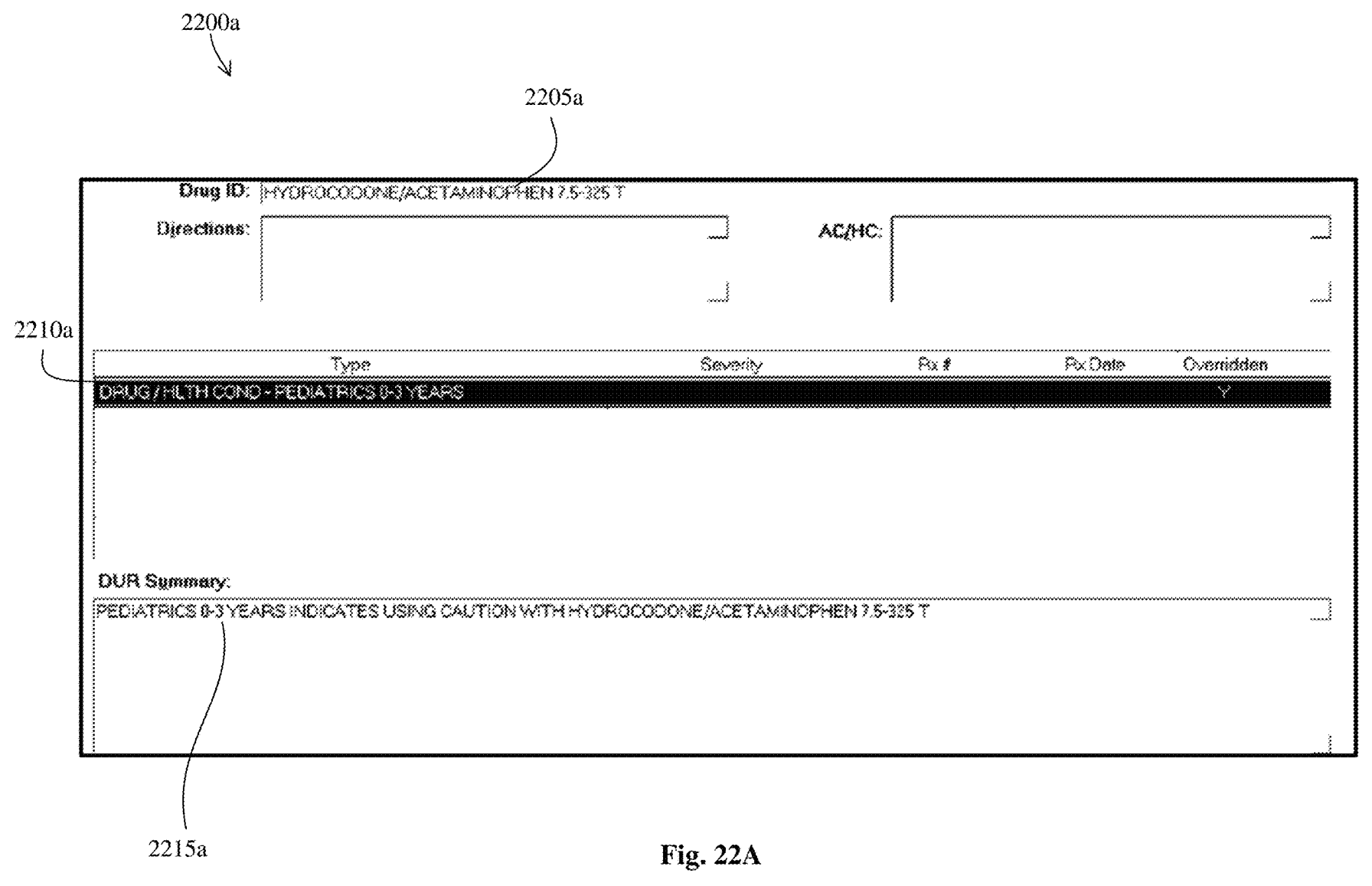
Figure 22B:
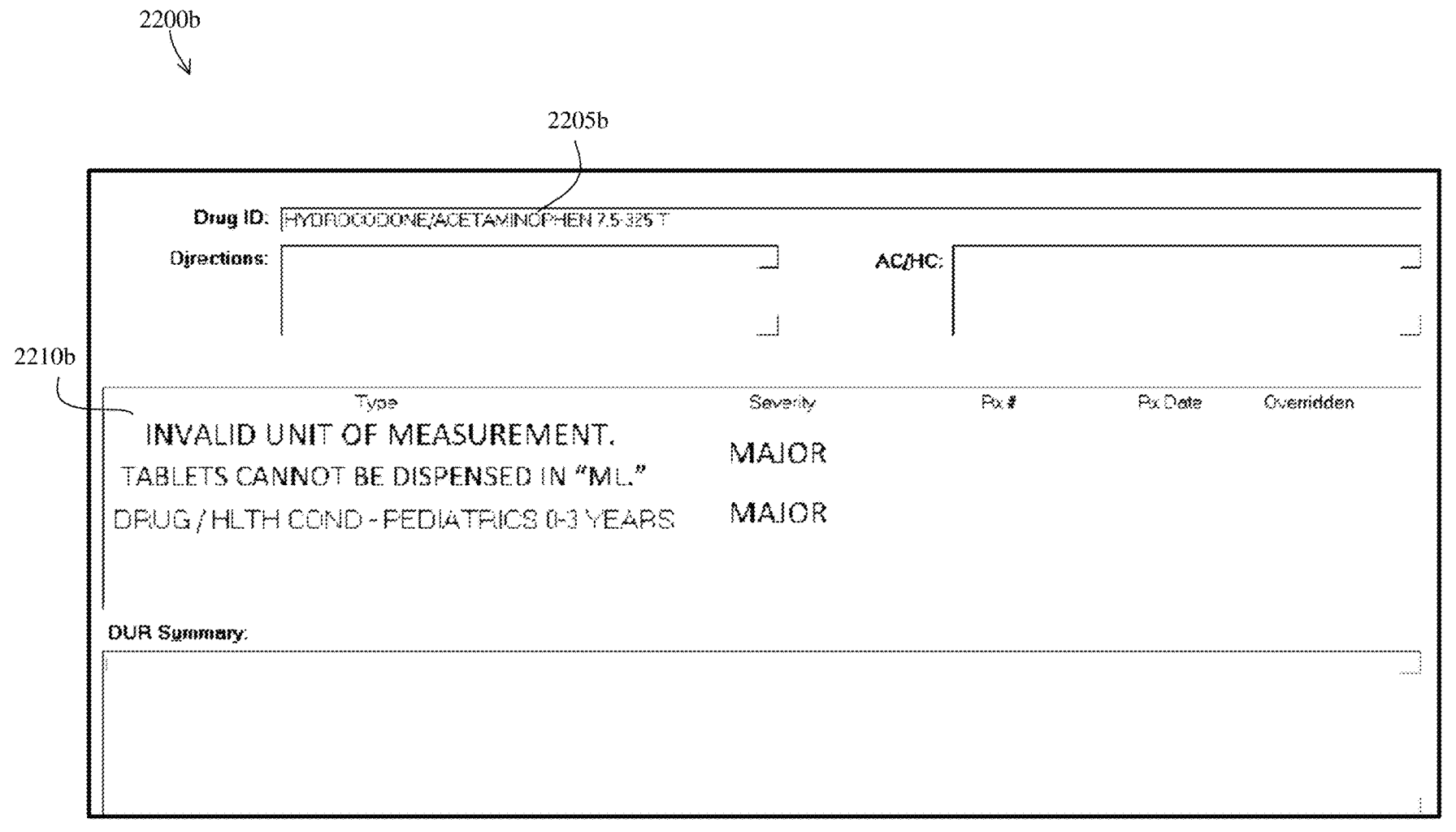

With reference to FIGS. 22A and B, a drug utilization review 2200a,b pediatric contraindicated health condition and/or an invalid measurement. For example, a prescription 300 may include an entered drug 310 Hydrocodone and a medication size 330 of 7.5/325/5 ml. Hydrocodone belongs to a group of medicines called narcotic analgesics (i.e., opioid pain medicines). Hydrocodone may act on the central nervous system (CNS) to relieve pain, and may stop or prevent cough. Hydrocodone is available only under a restricted distribution program called the Opioid Analgesic REMS (Risk Evaluation and Mitigation Strategy) program. The prescription 300 may also include prescriber instructions 312 that include "Take 2 ml po q 4 h." "PO" means the medication is to be taken by mouth. If a medicine is to be taken every so-many hours, it is written "q_h"; the "q" standing for "quaque" and the "h" indicating the number of hours. So, for example, "2 ml po q4h" means "Take 2 ml by mouth every 4 hours." An associated drug utilization rule may identify a pediatric contraindicated health condition and/or an invalid measurement. FIG. 22A illustrates a drug utilization review 2200a for a medication 2205a with a drug utilization rule 2210a and a drug utilization review summary 2215a. FIG. 22B illustrates a drug utilization review 2200b for a medication 2205b with a drug utilization rule 2210b and a drug utilization review summary 2215b.

Figure 23A:
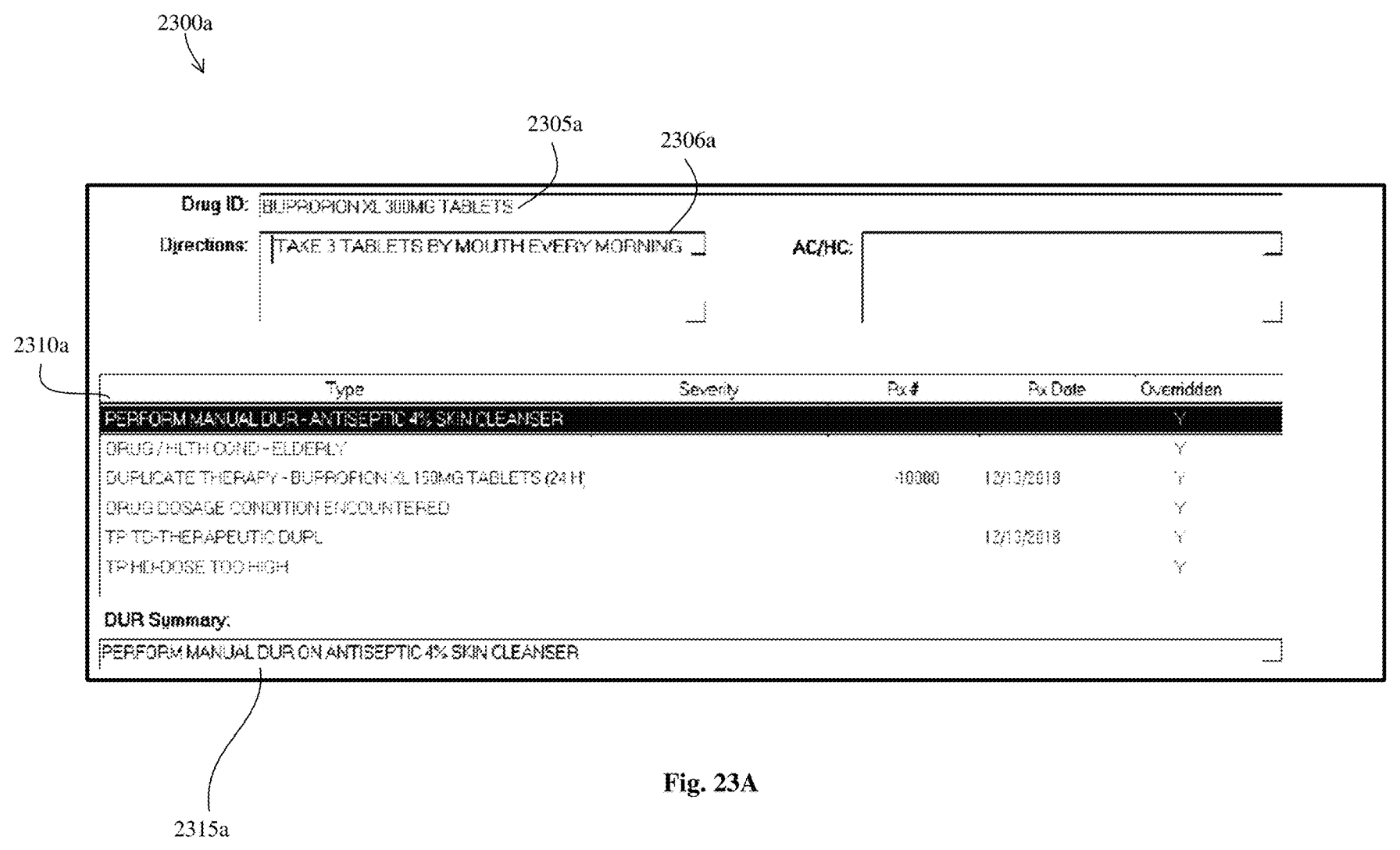

With reference to FIGS. 23A and B, a drug utilization review 2300a,b may identify an inappropriate dose. These drug utilization rules may be reserved for dosages well outside a normal therapeutic range that will likely result in patient harm. For example, a prescription 300 may include an entered drug 310 Wellbutrin XL with a medication size 330 of 300 mg. WELLBUTRIN XL® (bupropion hydrochloride) is an antidepressant of the aminoketone class. WELLBUTRIN XL tablets are supplied for oral administration as 150 mg and 300 mg creamy-white to pale yellow extended-release tablets. Each tablet may contain the labeled amount of bupropion hydrochloride and the inactive ingredients: ethylcellulose, glyceryl behenate, methacrylic acid copolymer dispersion, polyvinyl alcohol, polyethylene glycol, povidone, silicon dioxide, and triethyl citrate. The prescription 300 may include prescriber instructions 312 that includes "1 tablet TID." "TID" means three times a day, and is an abbreviation for "ter in die" which in Latin means three times a day. The prescriber instructions 312 may also include "Maximum daily dose 450 mg/daily max." An associated drug utilization rule may identify an inappropriate dosage (i.e., 300 mg at three times/day=900 mg, and maximum daily dose is 450 mg/day). FIG. 23A illustrates a drug utilization review 2300a for a medication 2305a with a drug utilization rule 2310a. FIG. 23B illustrates a drug utilization review 2300b for a medication 2305b having an associated prescriber instruction 2306b with a drug utilization rule 2310b and a drug utilization review summary 2315b.

Figure 24A:
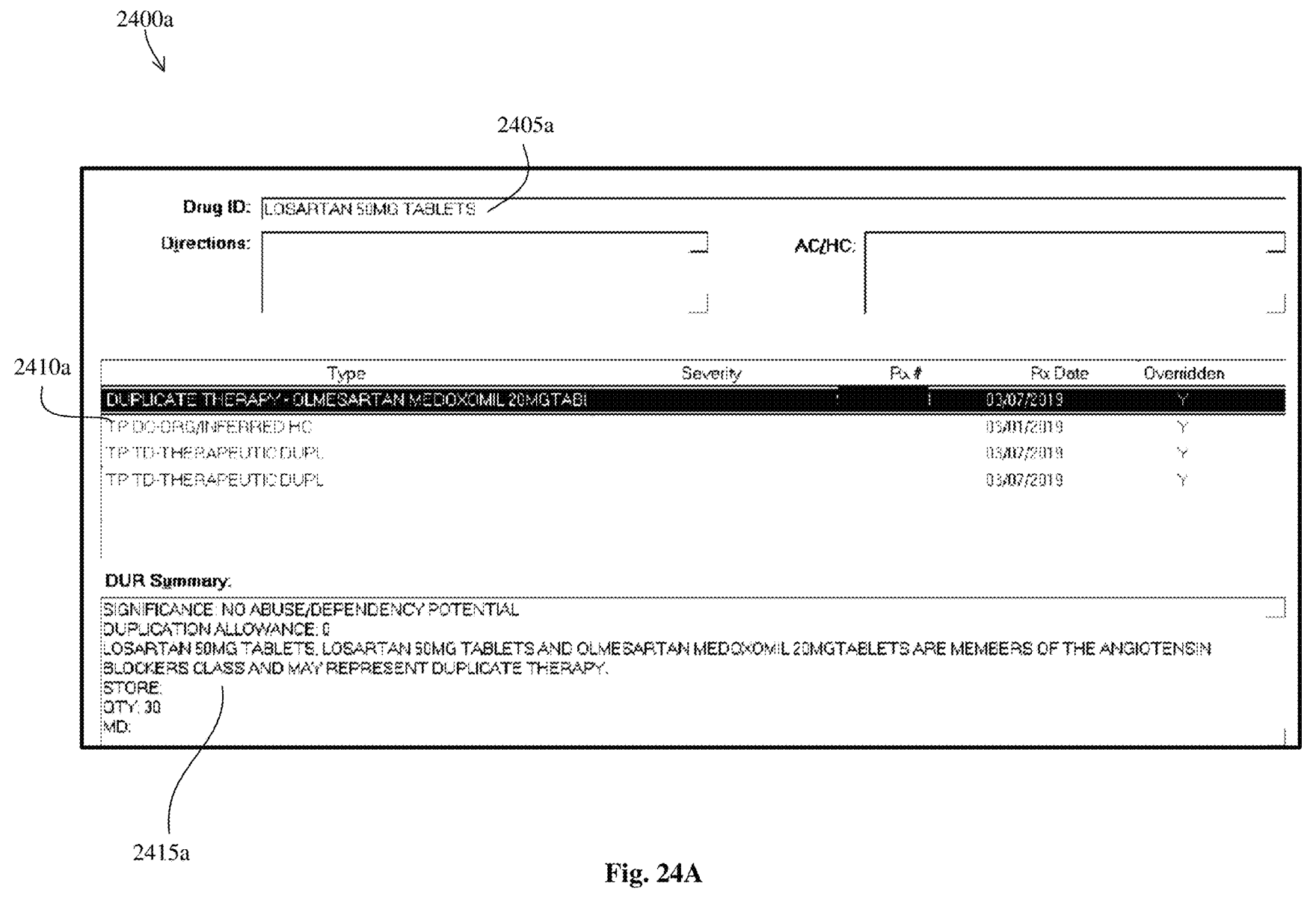
Figure 24B:
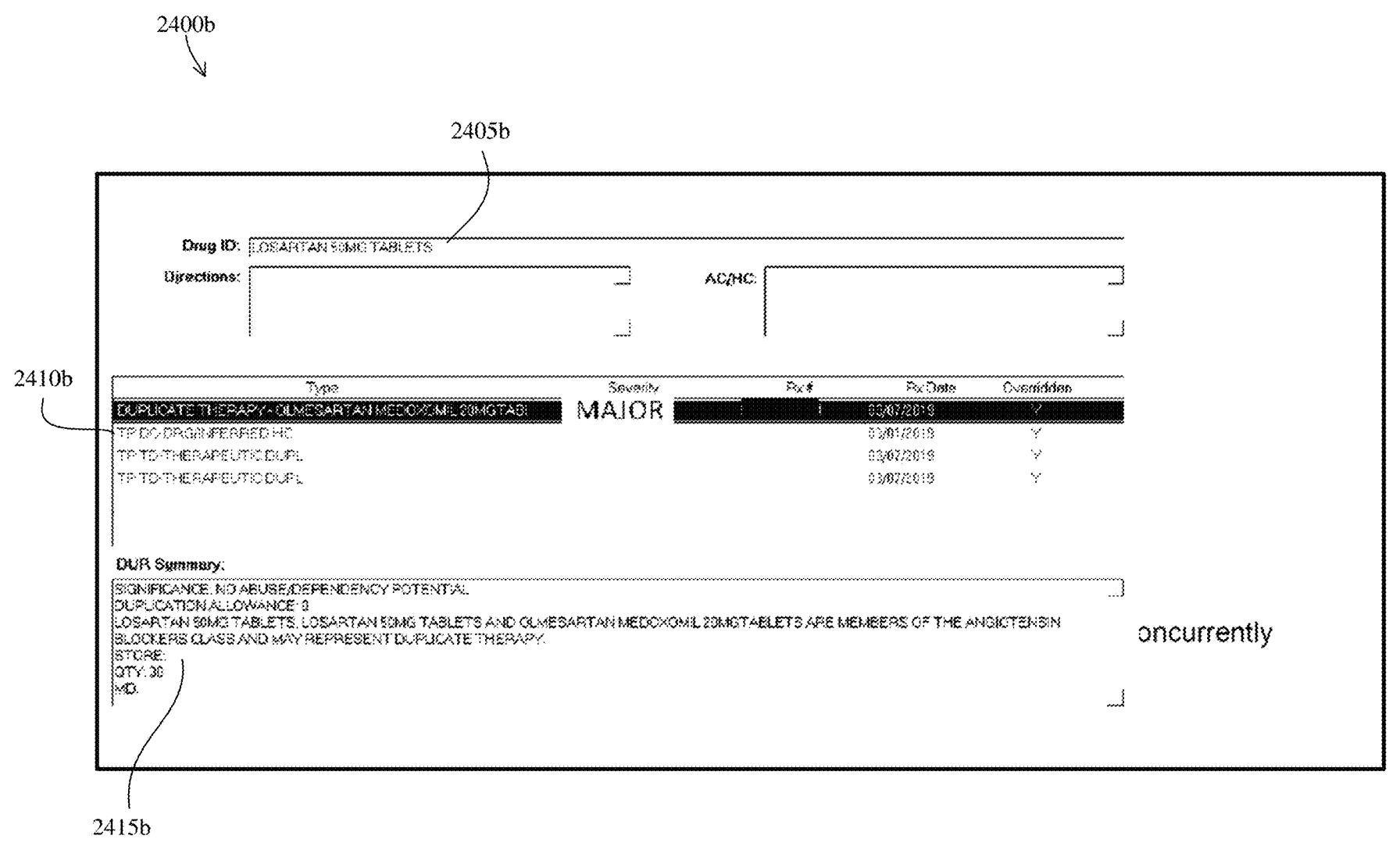

Turning to FIGS. 24A and B, a drug utilization review 2400a,b may identify a therapeutic duplication. This drug utilization review may be reserved for drugs that have no clinical rationale for therapeutic duplication that will likely result in patient harm. For example, a prescription 300 may include an entered drug 310 Olmesartan. Electronic healthcare records data for the patient 302 may indicate that the patient was recently prescribed Losartan. Olmesartan was prescribed after Losartan was recalled. Losartan prescription is not closed at time of Olmesartan dispensing and is requested via an automatic fill. Olmesartan may be used to treat high blood pressure (e.g., hypertension). Lowering high blood pressure helps prevent strokes, heart attacks, and kidney problems. Olmesartan belongs to a class of drugs called angiotensin receptor blockers (ARBs). Olmesartan works by relaxing blood vessels so that blood can flow more easily. Losartan may be used to treat high blood pressure (e.g., hypertension) and to help protect the kidneys from damage due to diabetes. Losartan is also used to lower the risk of strokes in patients with high blood pressure and an enlarged heart. Lowering high blood pressure helps prevent strokes, heart attacks, and kidney problems. Losartan belongs to a class of drugs called angiotensin receptor blockers (ARBs). Losartan works by relaxing blood vessels so that blood can flow more easily. An associated drug utilization rule may identify a therapeutic duplication (i.e., Olmesartan may be determined to be a therapeutic duplication with respect to Losartan). FIG. 24A illustrates a drug utilization review 2400a for a medication 2405a with a drug utilization rule 2410a and a drug utilization review summary 2415a. FIG. 24B illustrates a drug utilization review 2400b for a medication 2405b with a drug utilization rule 2410b and a drug utilization review summary 2415b.

Figure 25A:
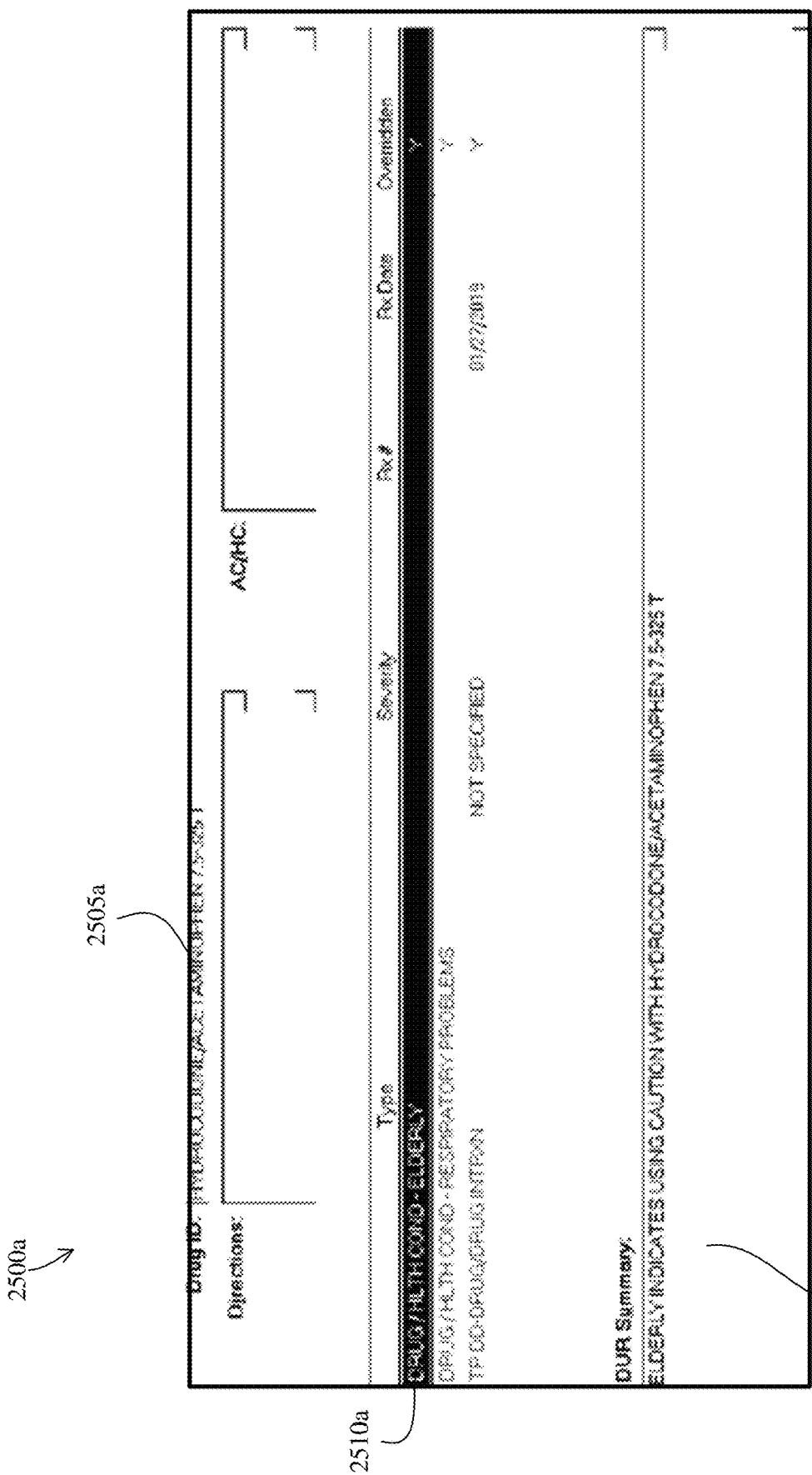
Figure 25B:
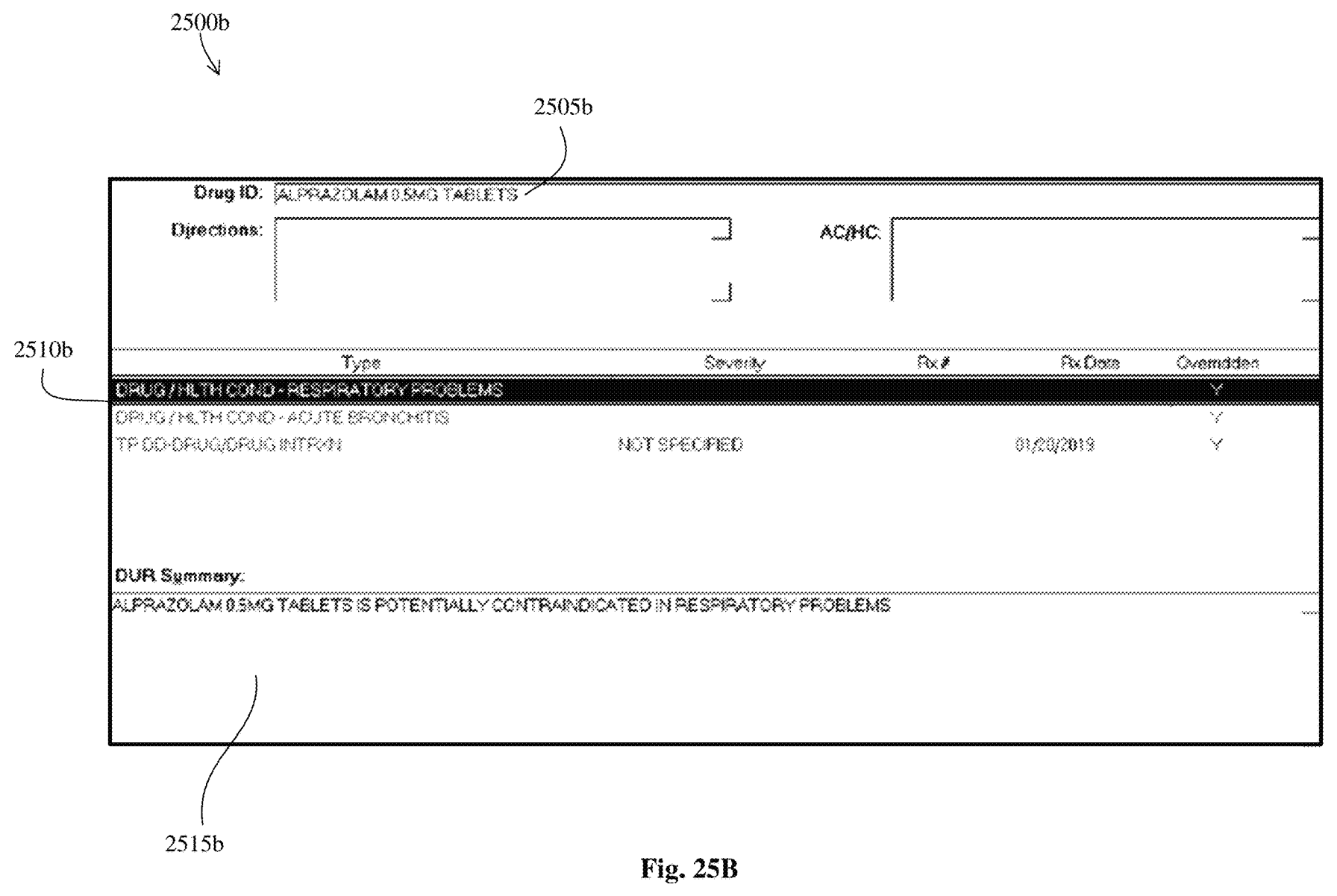
Figure 25C:
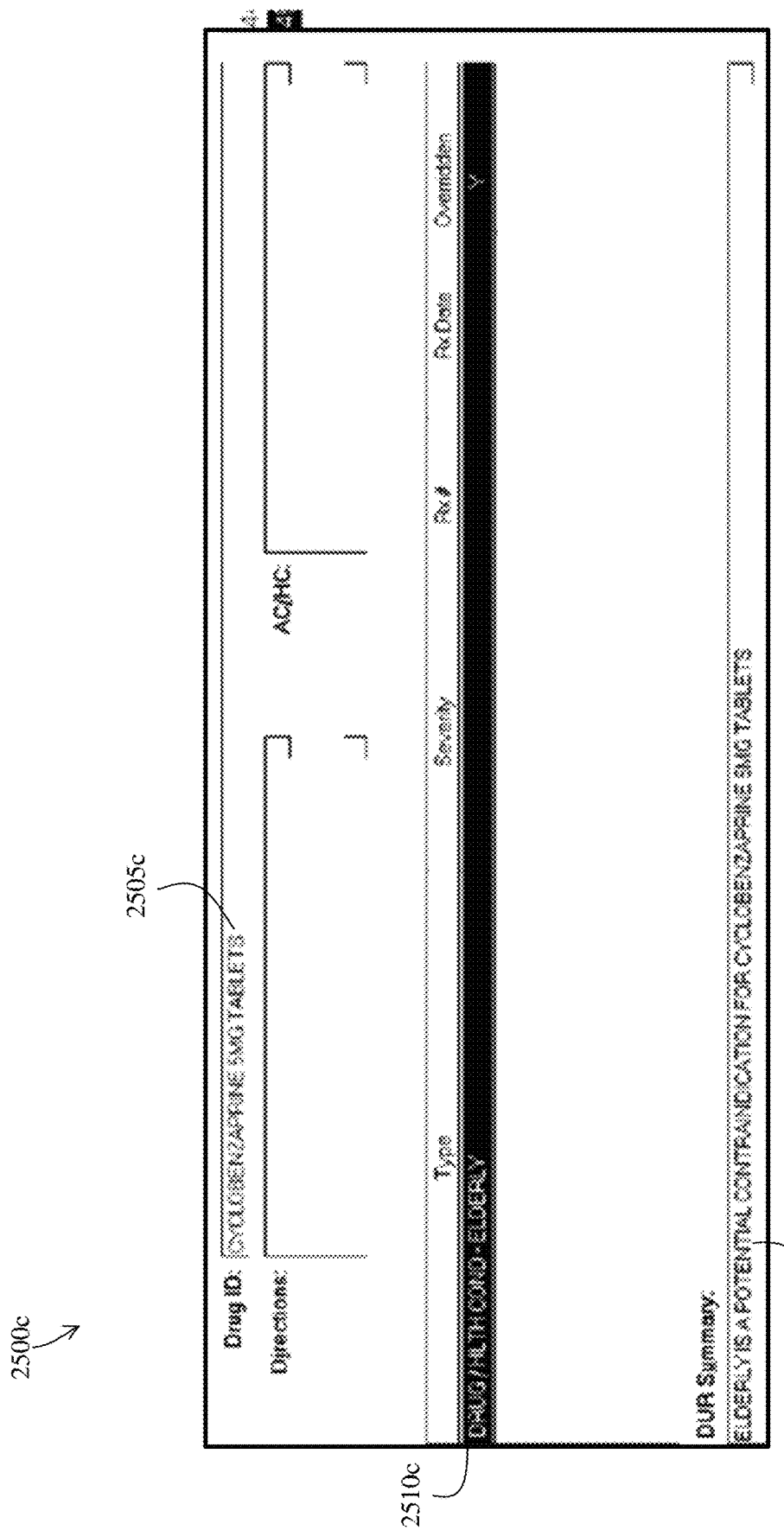

With reference to FIGS. 25A-D, a drug utilization review 2500a-d may identify a medication therapy to improve a patient outcome. For example, a prescription for Alprazolam, Hydrocodone and Cyclobenzaprine are all filled concurrently. Hydrocodone and acetaminophen combination may be used to relieve pain severe enough to require opioid treatment and when other pain medicines did not work well enough or cannot be tolerated. Acetaminophen may be used to relieve pain and reduce fever in patients. Acetaminophen may not become habit-forming when taken for a long time. But acetaminophen may cause other unwanted effects when taken in large doses, including liver damage. Hydrocodone belongs to the group of medicines called narcotic analgesics (opioid pain medicines). Hydrocodone may act on the central nervous system (CNS) to relieve pain, and stops or prevents cough. FIG. 25A illustrates a drug utilization review 2500a for a medication 2505a with a drug utilization rule 2510a and a drug utilization review summary 2515a. Alprazolam is used to treat anxiety and panic disorders. Alprazolam belongs to a class of medications called benzodiazepines which act on the brain and nerves (i.e., the central nervous system) to produce a calming effect. Alprazolam works by enhancing the effects of a certain natural chemical in the body (i.e., gamma-aminobutyric acid (GABA)). FIG. 25B illustrates a drug utilization review 2500b for a medication 2505b with a drug utilization rule 2510b and a drug utilization review summary 2515b. Cyclobenzaprine is a muscle relaxant. Cyclobenzaprine may work by blocking nerve impulses (or pain sensations) that are sent to a user's brain. Cyclobenzaprine may be used together with rest and physical therapy to treat skeletal muscle conditions such as pain or injury. FIG. 25C illustrates a drug utilization review 2500c for a medication 2505c with a drug utilization rule 2510c and a drug utilization review summary 2515c. Benzodiazepines are a type of medication known as tranquilizers. Familiar names include Valium and Xanax. They are some of the most commonly prescribed medications in the United States. When people without prescriptions obtain and take these drugs for their sedating effects, use may turn into abuse. FIG. 25D illustrates a drug utilization review 2500c for a medication 2505d with a drug utilization rule 2510d and a drug utilization review summary 2515d.

Turning to FIG. 26, a drug utilization rule 2600 may identify improved patient outcomes. This drug utilization review may pull forward a patient consultation to a more appropriate point in work flow (e.g., at a point where an eRx data from a prescriber is entered into pharmacy Rx data. For example, a healthcare patient is currently taking glimepiride monotherapy. Glimepiride monotherapy in achieving good blood glucose control in type-2 diabetes mellitus: a prospective observational study. This medication allows us to infer a health condition, even if not explicitly communicated by the prescriber. The patient has not received a prescription for statins or for blood glucose test strips in the last 120 days. Statins are a class of drugs often prescribed by doctors to help lower cholesterol levels in the blood. By lowering the levels, statins help prevent heart attacks and stroke. Statins, also known as HMG-COA reductase inhibitors, are a class of lipid-lowering medications that reduce illness and mortality in those who are at high risk of cardiovascular disease. Clinical guidelines suggest that all persons with diabetes should also be prescribed statins to improve health outcomes. Blood glucose test strips and blood glucose monitors, also known as diabetes monitors and blood glucose meters, may be used to monitor blood sugar levels and may also be used to infer a health condition of Diabetes in a patient. An associated drug utilization rule may identify a medication therapy to improve a patient outcome. FIG. 26 illustrates a drug utilization review 2600 for a medication 2605 with a drug utilization rule 2610 and a drug utilization review summary 2615.

Figure 27:
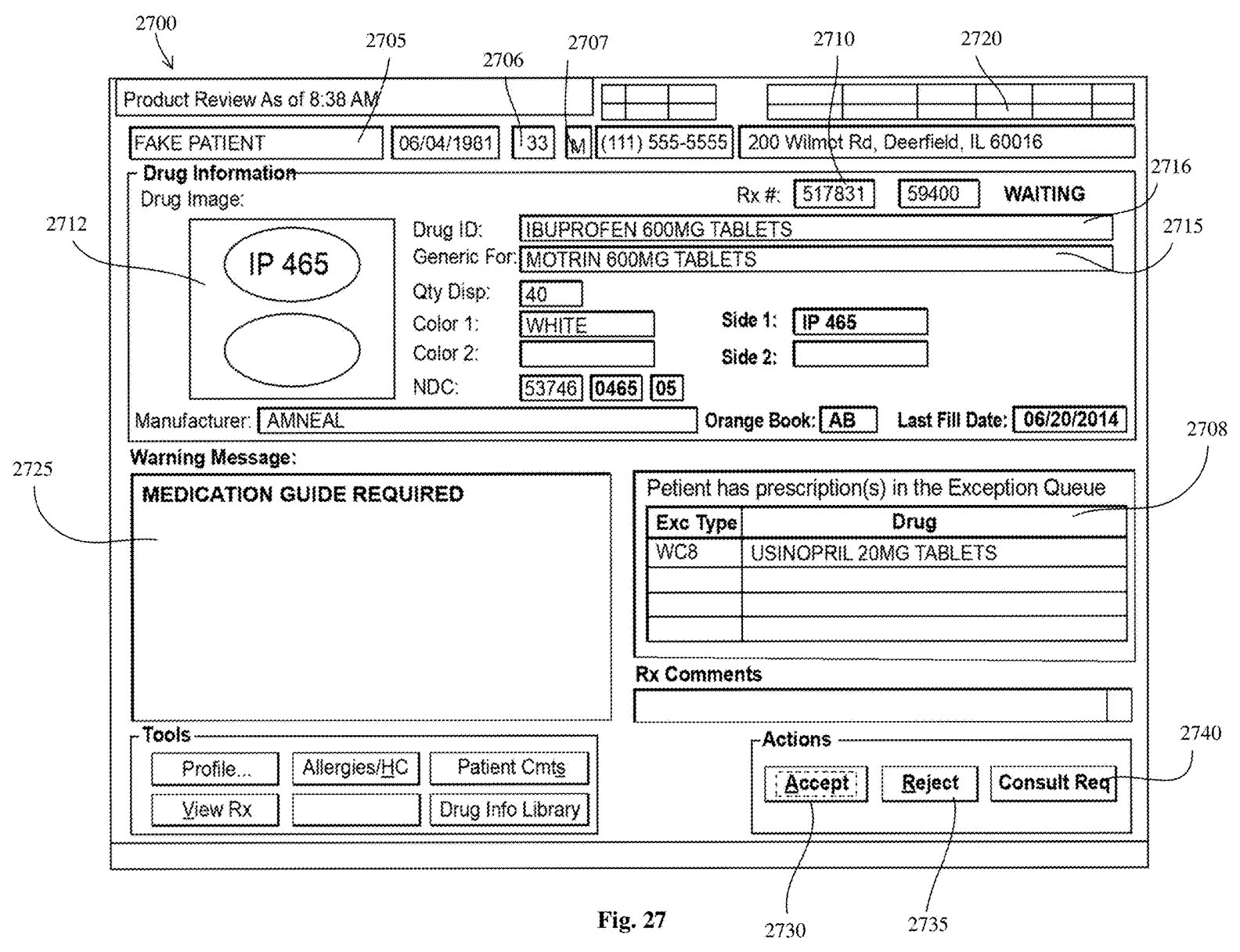

Turning to FIG. 27, drug related comments user interface 2700 may appear during data review. For example, quality alerts may appear during data review and data entry. Audits may be delivered during data entry and email, and may be delivered after a pharmacist has performed eRx data review. Preferably, this logic is moved as far left in the process flow as possible. The drug related comments user interface 2700 may include a patient name 2705, a patient age 2706, a patient sex 2707, patient prescription(s) in the exception queue 2708, an Rx #2710, a drug ID 2711, drug images 2712, a generic form 2715, a drug utilization review (DRU) selection icon 2720, a warning message 2725, an accept selection icon 2730, a reject selection icon 2735, and a consult request selection icon 2740. When a user selects the DUR icon 2720, a drug utilization review may be initiated for the respective medication 2711 and/or patient 2705. When a user (e.g., a pharmacist 2705) selects the consult request selection icon 2740, a consultation request may be transmitted to, for example, a patient 2705 and/or a prescriber. When a user (e.g., a patient 2705) selects the accept selection icon 2730, the user (e.g., a patient 2705) may be indicating an acceptance of, for example, a requested consultation. When a user (e.g., a patient 2705) selects the reject selection icon 2730, the user (e.g., a patient 2705) may be indicating a rejection of, for example, a requested consultation.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing." "computing," "calculating," "determining." "presenting." "displaying." or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

ASPECTS

A drug utilization engine may receive prescription information that may include at least one of: an identification of a type of medication, a dosage of the medication, a frequency of administration for the medication, a method of administration of the medication, or a quantity of the medication.

A drug utilization engine may receive medication benefits (formulary) information associated with the healthcare patient that may include list of prescription drugs and associated costs that are covered by a prescription drug plan or another insurance plan offering prescription drug benefits.

A drug utilization engine may include a message generation and transmission module stored on a memory that, when executed by a processor, may cause the processor to generate a pharmacy record including a medication when a medication of the prescription for the healthcare patient is determined to be within the medication formulary. The pharmacy record may be representative of a pharmacy prescription.

A drug utilization engine may include a pharmacy data receiving module stored on a memory that, when executed by a processor, cause the processor to receive pharmacy data. The pharmacy data may be representative of an alternate medication for the healthcare patient.

A drug utilization engine may receive alternate medication that may be a therapeutic equivalency with respect to a medication included within electronic prescription data.

A drug utilization engine may include a message generation and transmission module stored on a memory that, when executed by a processor, may cause the processor to generate a patient message, wherein the patient message may indicate that the medication included within an electronic prescription data has been replaced with an alternate medication.

A drug utilization engine may receive data representative of an alternate medication that may be a bioequivalent with respect to a medication included within electronic prescription data.

A drug utilization engine may include a message generation and transmission module stored on a memory that, when executed by a processor, may cause the processor to generate a prescriber message. The prescriber message may be representative of a request to have the prescriber replace the medication included within electronic prescription data with an alternate medication.

A computer-readable medium may include computer-readable instructions that, when executed by a processor, may cause the process to receive prescription information that may include at least one of: an identification of a type of medication, a dosage of the medication, a frequency of administration for the medication, a method of administration of the medication, or a quantity of the medication.

A computer-readable medium may include a pharmacy data receiving module that, when executed by a processor, may cause the processor to receive pharmacy data. The pharmacy data may be representative of an alternate medication for the healthcare patient.

A computer-readable medium may include computer-readable instructions that, when executed by a processor, may cause the process to receive data representative an alternate medication that may be a bioequivalent with respect to a medication included within electronic prescription data.

A computer-readable medium may include a message generation and transmission module that, when executed by a processor, may cause the processor to generate a prescriber message. The prescriber message may be representative of a request to have the prescriber replace a medication included within electronic prescription data with an alternate medication.

A computer-readable may include a response generation and transmission module that, when executed by a processor, may cause the processor to generate a prescriber response. The prescriber response may be representative of revised electronic prescription data. The revised electronic prescription data may be indicative of a medication included within electronic prescription data being replaced with an alternate medication.

A method of claim may include receiving prescription information that may include at least one of: an identification of a type of medication, a dosage of the medication, a frequency of administration for the medication, a method of administration of the medication, or a quantity of the medication.

A method may include receiving, at a processor, pharmacy data in response to the processor executing a pharmacy data receiving module. The pharmacy data may be representative of an alternate medication for a healthcare patient.

A method may include receiving data representative of an alternate medication that may be a bioequivalent with respect a medication included within electronic prescription data.

A method may include generating, using a processor, a prescriber message in response to the processor executing a message generation and transmission module. The prescriber message may be representative of a request to have a prescriber replace a medication included within electronic prescription data with an alternate medication.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A drug utilization engine, comprising:
   one or more processors;
   one or more network-based non-transitory storage devices configured to store pharmacy prescription records in a collection of medical records in a standardized pharmacy format; and
   a non-transitory computer-readable medium having computer-readable instructions stored thereon that, when executed by the one or more processors, cause the one or more processors to:
   provide remote access to one or more users over a network so the one or more users can upload one or more electronic prescriptions in real-time through a graphical user interface, wherein the one or more users upload the one or more electronic prescriptions in a non-standardized electronic prescription format dependent on hardware and software platform used by the one or more users;
   receive an electronic prescription from a user, wherein the electronic prescription includes one or more medications for a healthcare patient, and the one or more medications include a particular medication;
   receive pharmacy prescription data, wherein the pharmacy prescription data is representative of an alternate medication of the particular medication, of the one or more medications, for the healthcare patient;
   generate a prescriber message, wherein the prescriber message is representative of a change request to have a prescriber replace the particular medication included within the electronic prescription with the alternate medication;

determining that the prescriber did not approve the change request;

responsive to determining that the prescriber did not approve the change request, generate a patient message, wherein the patient message indicates that the medication included within the electronic prescription has been replaced with the alternate medication;

receive payer data from a payer device in response to receiving the electronic prescription, wherein the payer data is representative of medication formulary and benefit information associated with the healthcare patient, and wherein the benefit information is representative of at least one of: a deductible for the healthcare patient, a maximum amount that will be paid to a pharmacy, or a maximum amount that will be paid for the alternate medication;

compare the electronic prescription with the payer data in response to receiving the electronic prescription and the payer data;

verify that the alternate medication for the healthcare patient is included within the medication formulary, based on the comparison of the electronic prescription with the payer data, and wherein the verification is further based on at least one of: the deductible for the healthcare patient, the maximum amount that will be paid to the pharmacy, or the maximum amount that will be paid for the alternate medication;

convert, by the one or more processors, the electronic prescription to a pharmacy prescription record;

store the pharmacy prescription record in the collection of medical records in the standardized format in the one or more network-based non-transitory storage devices;

generate a pharmacy prescription based on the pharmacy prescription record; and transmit the pharmacy prescription to the one or more users such that the one or more users has immediate access to up-to-date information.

2. The drug utilization engine of claim 1, wherein the pharmacy prescription record includes at least one of: an identification of a type of at least one medication of the one or more medications, a dosage of the at least one medication, a frequency of administration for the at least one medication, a method of administration of the at least one medication, or a quantity of the at least one medication.

3. The drug utilization engine of claim 1, wherein the medication formulary information associated with the healthcare patient includes list of prescription drugs covered by a prescription drug plan or another insurance plan offering prescription drug benefits.

4. The drug utilization engine of claim 1, wherein the computer-readable instructions, when executed by the one or more processors, further cause the one or more processors to:

generate a pharmacy record including the alternate medication when the alternate medication for the healthcare patient is determined to be within the medication formulary, wherein the pharmacy record is representative of the pharmacy prescription.

5. The drug utilization engine of claim 1, wherein the alternate medication is a therapeutic equivalency with respect to the particular medication.

6. The drug utilization engine of claim 1, wherein the alternate medication is a bioequivalent with respect to the particular medication.

7. A non-transitory computer-readable medium storing a set of computer-readable instructions that, when executed by one or more processors, cause the one or more processors to:

provide remote access to one or more users over a network so the one or more users can upload one or more electronic prescriptions in real-time through a graphical user interface, wherein the one or more users upload the one or more electronic prescriptions in a non-standardized electronic prescription format dependent on hardware and software platform used by the one or more users;

receive an electronic prescription from a user, wherein the electronic prescription includes one or more medications for a healthcare patient, and the one or more medications include a particular medication;

receive pharmacy prescription data, wherein the pharmacy prescription data is representative of an alternate medication of the particular medication, of the one or more medications, for the healthcare patient;

generate a prescriber message, wherein the prescriber message is representative of a change request to have a prescriber replace the particular medication included within the electronic prescription with the alternate medication;

determine that the prescriber did not approve the change request;

responsive to determining that the prescriber did not approve the change request, generate a patient message, wherein the patient message indicates that the medication included within the electronic prescription has been replaced with the alternate medication;

receive payer data from a payer device in response to receiving the electronic prescription, wherein the payer data is representative of medication formulary information associated with the healthcare patient and at least one of: a deductible for the healthcare patient, a maximum amount that will be paid to a pharmacy, or a maximum amount that will be paid for the alternate medication;

compare the electronic prescription with the payer data in response to receiving the electronic prescription and the payer data;

verify that the alternate medication for the healthcare patient is included within the medication formulary, based on the comparison of the electronic prescription with the payer data, and wherein the verification is further based on at least one of: the deductible for the healthcare patient, the maximum amount that will be paid to the pharmacy, or the maximum amount that will be paid for the alternate medication;

convert, by the one or more processors, the electronic prescription data to pharmacy prescription record;

store the pharmacy prescription record in a collection of medical records in a standardized format in one or more network-based non-transitory storage devices, the one or more network-based non-transitory storage devices configured to store pharmacy prescription records in the collection of medical records in the standardized pharmacy format;

generate a pharmacy prescription based on the pharmacy prescription record; and transmit the pharmacy prescription to the one or more users such that the one or more users has immediate access to up-to-date information.

8. The computer-readable medium of claim 7, wherein the pharmacy prescription record includes at least one of: an identification of a type of at least one medication of the one or more medications, a dosage of the at least one medication, a frequency of administration for the at least one medication, a method of administration of the at least one medication, or a quantity of the at least one medication.

9. The computer-readable medium of claim 7, wherein the alternate medication is a bioequivalent with respect to a medication included within the electronic prescription.

10. A computer-implemented method to implement a drug utilization review, the method comprising:
providing remote access to one or more users over a network so the one or more users can upload one or more electronic prescriptions in real-time through a graphical user interface, wherein the one or more users upload the one or more electronic prescriptions in a non-standardized electronic prescription format dependent on hardware and software platform used by the one or more users;
receiving an electronic prescription from a user, wherein the electronic prescription includes one or more medications for a healthcare patient, and the one or more medications include a particular medication;
receiving pharmacy prescription data, wherein the pharmacy prescription data is representative of an alternate medication of the particular medication, of the one or more medications, for the healthcare patient;
generating a prescriber message, wherein the prescriber message is representative of a change request to have a prescriber replace the particular medication included within the electronic prescription with the alternate medication;
determining that the prescriber did not approve the change request;
responsive to determining that the prescriber did not approve the change request, generating a patient message, wherein the patient message indicates that the medication included within the electronic prescription has been replaced with the alternate medication;
receiving, from a payer device, payer data at a processor of a computing device in response to the processor executing a payer data receiving module in response to receiving the electronic prescription, wherein the payer data is representative of medication formulary information associated with the healthcare patient and at least one of: a deductible for the healthcare patient, a maximum amount that will be paid to a pharmacy, or a maximum amount that will be paid for the alternate medication;
comparing, using a processor of a computing device, the electronic prescription with the payer data;
verifying that the alternate medication for the healthcare patient is included within the medication formulary, based on the comparison of the electronic prescription with the payer data, and wherein the verification is further based on at least one of: the deductible for the healthcare patient, the maximum amount that will be paid to the pharmacy, or the maximum amount that will be paid for the alternate medication, in response to the processor executing a prescription verification module;
converting, using the one or more processors, the electronic prescription data to pharmacy prescription record;
storing the pharmacy prescription record in a collection of medical records in a standardized format in one or more network-based non-transitory storage devices, the one or more network-based non-transitory storage devices configured to store pharmacy prescription records in a collection of medical records in the standardized pharmacy format;
generating a pharmacy prescription based on the pharmacy prescription record; and
transmitting the pharmacy prescription to the one or more users such that the one or more users has immediate access to up-to-date information.

11. The method of claim 10, wherein the pharmacy prescription record includes at least one of: an identification of a type of at least one medication of the one or more medications, a dosage of the at least one medication, a frequency of administration for the at least one medication, a method of administration of the at least one medication, or a quantity of the at least one medication.

12. The method of claim 10, wherein the alternate medication is a bioequivalent with respect a medication included within the electronic prescription data.

* * * * *